US008501747B2

(12) United States Patent
de lera Ruiz et al.

(10) Patent No.: US 8,501,747 B2
(45) Date of Patent: Aug. 6, 2013

(54) FUNCTIONALLY SELECTIVE ALPHA2C ADRENORECEPTOR AGONISTS

(75) Inventors: Manuel de lera Ruiz, Branchburg, NJ (US); Kevin D. McCormick, Basking Ridge, NJ (US); Christopher W. Boyce, Flemington, NJ (US); Robert G. Aslanian, Rockaway, NJ (US); Younong Yu, East Brunswick, NJ (US); Pietro Mangiaracina, Monsey, NY (US); Junying Zheng, New Providence, NJ (US); Michael Y. Berlin, Flemington, NJ (US); Stephanie Louise Ciesla, Morristown, NJ (US); Chia-Yu Huang, Princeton Junction, NJ (US); Bo Liang, East Brunswick, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 713 days.

(21) Appl. No.: 12/525,641

(22) PCT Filed: Feb. 11, 2008

(86) PCT No.: PCT/US2008/001765
§ 371 (c)(1),
(2), (4) Date: Apr. 19, 2010

(87) PCT Pub. No.: WO2008/100456
PCT Pub. Date: Aug. 21, 2008

(65) Prior Publication Data
US 2010/0197562 A1 Aug. 5, 2010

Related U.S. Application Data

(60) Provisional application No. 60/901,045, filed on Feb. 13, 2007.

(51) Int. Cl.
| | |
|---|---|
| A61K 31/404 | (2006.01) |
| A61K 31/4025 | (2006.01) |
| A61K 31/4178 | (2006.01) |
| A61K 31/4439 | (2006.01) |
| A61K 31/4709 | (2006.01) |
| A61K 31/506 | (2006.01) |
| C07D 401/04 | (2006.01) |
| C07D 401/14 | (2006.01) |
| C07D 403/02 | (2006.01) |
| C07D 403/14 | (2006.01) |

(52) U.S. Cl.
USPC ........ 514/256; 544/333; 548/312.1; 546/167; 546/272.7; 514/314; 514/339; 514/397

(58) Field of Classification Search
None
See application file for complete search history.

(56) References Cited

U.S. PATENT DOCUMENTS

| | | | |
|---|---|---|---|
| 5,658,938 | A | 8/1997 | Geerts et al. |
| 6,841,684 | B2 | 1/2005 | Chow et al. |
| 2003/0023098 | A1 | 1/2003 | Chow et al. |
| 2007/0093477 | A1 | 4/2007 | McCormick et al. |
| 2007/0099872 | A1 | 5/2007 | McCormick et al. |
| 2008/0027100 | A1 | 1/2008 | McCormick et al. |

FOREIGN PATENT DOCUMENTS

| | | |
|---|---|---|
| WO | WO 97/12874 | 4/1997 |
| WO | WO 99/28300 | 6/1999 |
| WO | WO 2001/00586 | 1/2001 |
| WO | WO 02/068411 | 9/2002 |
| WO | WO 02/076950 | 10/2002 |
| WO | WO 2005/005781 | 11/2005 |
| WO | WO 2007/024944 | 3/2007 |
| WO | WO 2007024949 | 3/2007 |
| WO | WO 2007 084391 | 7/2007 |
| WO | WO 2007/085556 | 8/2007 |
| WO | WO 2008/100456 A2 | 8/2008 |
| WO | WO 2008/100459 A1 | 8/2008 |
| WO | WO 2008/100463 A1 | 8/2008 |
| WO | WO 2008/100480 A1 | 8/2008 |

OTHER PUBLICATIONS

Ahlquist RP, "A Study of the Adrenotropic Receptors," Am. J. Physiol., (1948), pp. 586-600, vol. 153.
Bagley et al., "Synthesis and Alpha.2-adrenergic Activities of Imidazole and Imidazolidine analogues, in Vivtro and in Vivo Selectivity", Medicinal Chemistry Research, Birkhauser, Boston, US, (1994), pp. 346-364, vol. 4 No. 5.
Bousquet et al., "Role of the Ventral Surface of the Brain Stem in the Hypotensive Action of Clonidine", European Journal of Pharmacology, (1975), pp. 151-156, vol. 34.
Bousquet, P. et al., "Imidazoline Receptors: From Basic Concepts to Recent Developments", Journal of Cardiovascular Pharmacology, (1995), pp. S1-S6, (Suppl. 2). vol. 26.
Hong et al., "A Structure-Activity Relationship Study of Benzylic Modification of 4-[1-(1-Naphtyl)ethyl]-1 H-imidazoles on α-2-Adrenergic Receptors", J. Med. Chem., (1994) pp. 2328-2333, vol. 37.
Lands et al., "Differentiation of Receptor Systems Activated by Sympathomimetic Amines", Nature, (1967), pp. 597-598, vol. 214.
MacDonald et al., "Gene Targeting—Homing in on Alpha2-Adrenoceptor-Subtype Function", TiPS, (1997), pp. 211-219, vol. 18.

(Continued)

Primary Examiner — Michael Barker
(74) Attorney, Agent, or Firm — H. Eric Fischer; Gerard M. Devlin

(57) ABSTRACT

In its many embodiments, the present invention provides a novel class of biaryl compounds as inhibitors of ÿ2C adrenergic receptor agonists, methods of preparing such compounds, pharmaceutical compositions containing one or more such compounds, methods of preparing pharmaceutical formulations comprising one or more such compounds, and methods of treatment, prevention, inhibition, or amelioration of one or more conditions associated with the ÿ2C adrenergic receptors using such compounds or pharmaceutical compositions.

7 Claims, No Drawings

OTHER PUBLICATIONS

Michel et al., "Classification of Alpha1-Adrenoceptor Subtypes", Naunyn-Schmiedeberg's Arch Pharmacol., (1995), pp. 1-10, vol. 352.

Reis et al., "The Imidazoline Receptor: Pharmacology, Functions, Ligands, and Relevance to Biology and Medicine", Annals of the New York Academy of Sciences, (1995), vol. 763, Table of Contents.

Yoo et al., "The Conformation and Activity of Benzofuran Derivatives as Angiotensin II Receptor Antagonists", Bioorganic & Medicinal Chemistry, (1997), pp. 445-459, vol. 5. No. 2.

Zhang et al., "Medetomidine Analogs as $\alpha 2$-Adrenergic Ligands. 2. Design, Synthesis, and Biological activity of Conformationally Restricted Naphthalene Derivatives of Medetomidine", J. Med. Chem., (1996), pp. 3001-3013, vol. 39.

Zhang et al., "Medetomidine Analogs as $\alpha 2$-Adrenergic Ligands. 3. Synthesis and Biological Evaluation of a New Series of Medetomidine Analogs and Their Potential Binding Interactions with $\alpha 2$-Adrenoceptors Involving a "Methyl Pocket"", J. Med. Chem., (1997), pp. 3014-3024, vol. 40.

Written Opinion of the International Searching Authority for PCT/US2008/001765—AL06619, 10 pages, (2008).

International Search Report (PCT/US2008/001765) for AL06619 mail date Dec. 9, 2008, 5 pages.

FUNCTIONALLY SELECTIVE ALPHA2C ADRENORECEPTOR AGONISTS

RELATED APPLICATIONS

This application claims priority to provisional application U.S. Ser. No. 60/901,045, filed on Feb. 13, 2007, herein incorporated by reference.

FIELD OF THE INVENTION

The present invention relates to biaryl compounds useful as α2C adrenergic receptor agonists, methods for making the compounds, pharmaceutical compositions containing the compounds, and methods of treatment and prevention using the compounds and compositions to treat disease states such as congestion (including nasal), migraine, congestive heart failure, cardiac ischemia, glaucoma, stress-induced urinary incontinence, attention deficit disorder, pain and psychotic disorders without substantial adverse side effects associated with α2A receptor agonist treatments.

BACKGROUND OF THE INVENTION

The initial classification of adrenergic receptors into α- and β-families was first described by Ahlquist in 1948 (Ahlquist R P, "A Study of the Adrenergic Receptors," Am. J. Physiol. 153:586-600 (1948)). Functionally, the α-adrenergic receptors were shown to be associated with most of the excitatory functions (vasoconstriction, stimulation of the uterus and pupil dilation). β-adrenergic receptors were implicated in vasodilation, bronchodilation and myocardial stimulation (Lands et al., "Differentiation of Receptor Systems Activated by Sympathomimetic amines," Nature 214:597-598 (1967)). Since this early work, α-adrenergic receptors have been subdivided into α1- and α2-adrenergic receptors. Cloning and expression of α-adrenergic receptors have confirmed the presence of multiple subtypes of both α1-(α1A, α1B, α1D) and α2-(α2A, α2B, α2C) adrenergic receptors (Michel et al., "Classification of $α_1$-Adrenoceptor Subtypes," Naunyn-Schmiedeberg's Arch. Pharmacol, 352:1-10 (1995); Macdonald et al., "Gene Targeting—Homing in on $α_2$-Adrenoceptor-Subtype Function," TIPS, 18:211-219 (1997)).

Current therapeutic uses of α-2 adrenergic receptor drugs involve the ability of those drugs to mediate many of the physiological actions of the endogenous catecholamines. There are many drugs that act on these receptors to control hypertension, intraocular pressure, eye reddening and nasal congestion and induce analgesia and anesthesia.

α2 adrenergic receptors can be found in the rostral ventrolateral medulla, and are known to respond to the neurotransmitter norepinephrine and the antihypertensive drug clonidine to decrease sympathetic outflow and reduce arterial blood pressure (Bousquet et al., "Role of the Ventral Surface of the Brain Stem in the Hypothesive Action of Clonidine," Eur. J. Pharmacol., 34:151-156 (1975); Bousquet et al., "Imidazoline Receptors: From Basic Concepts to Recent Developments," 26:S1-S6 (1995)). Clonidine and other imidazolines also bind to imidazoline receptors (formerly called imidazoline-guanidinium receptive sites or IGRS) (Bousquet et al., "Imidazoline Receptors: From Basic Concepts to Recent Developments," 26:S1-S6 (1995)). Some researchers have speculated that the central and peripheral effects of imidazolines as hypotensive agents may be related to imidazoline receptors (Bousquet et al., "Imidazoline Receptors: From Basic Concepts to Recent Developments," 26:S1-S6 (1995); Reis et al., "The Imidazoline Receptor: Pharmacology, Functions, Ligands, and Relevance to Biology and Medicine," Ann. N.Y. Acad. Sci., 763:1-703 (1995).

Compounds having adrenergic activity are well-known in the art, and are described in numerous patents and scientific publications. It is generally known that adrenergic activity is useful for treating animals of the mammalian species, including humans, for curing or alleviating the symptoms and conditions of numerous diseases and conditions. In other words, it is generally accepted in the art that pharmaceutical compositions having an adrenergic compound or compounds as the active ingredient are useful for treating, among other things, glaucoma, chronic pain, migraines, heart failure, and psychotic disorders.

For example, published PCT application WO 02/076950 discloses compounds having α2 agonist activity of the following general formula:

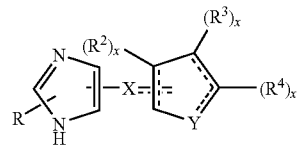

Other publications disclosing similar compounds include WO 01/00586, WO 99/28300, U.S. Pat. No. 6,841,684 B2 and US 2003/0023098 A1.

Another class of compounds having α2-agonist properties is disclosed in U.S. Pat. No. 5,658,938. This class of compounds has the following general formula:

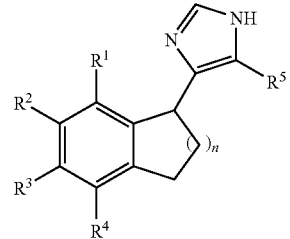

wherein na=1-2,
$R^1$-$R^3$ represent hydrogen, halogen hydroxy,
alkyl or alkoxy, and $R^5$ is hydrogen or alkyl.

Another class of compounds reported to have affinity for α2 receptors includes the following two compounds (Bagley et. al., Med. Chem. Res. 1994, 4:346-364):

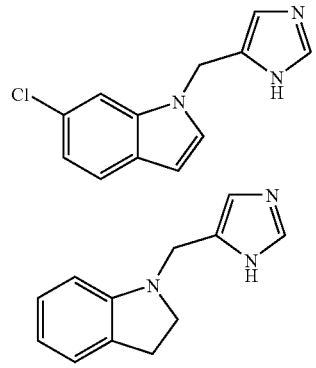

It is also known that compounds having adrenergic activity, such as α2A agonists, may be associated with undesirable side effects. Examples of such side effects include hyper- and hypotension, sedation, locomotor activity, and body temperature variations.

Another class of compounds reported to have affinity for α2 receptors includes the following two compounds (Miller et. al., *J. Med. Chem.* 1994, 37:2328-2333; *J. Med. Chem.* 1996, 39:3001-3013; *J. Med. Chem.* 1997, 37:3014-3024):

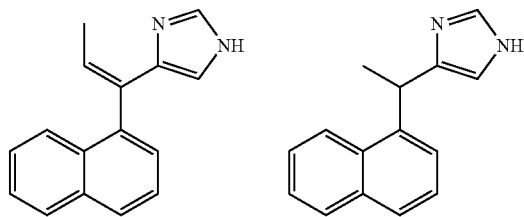 [SMILES: C/C=C(\c1c[nH]cn1)c1cccc2ccccc12 ; CC(c1c[nH]cn1)c1cccc2ccccc12]

Another class of indane and tetrahyrdonaphthalene type compounds having α2-agonist properties is disclosed in PCT application WO 97/12874 and WO20040506356 This class has the following general formula:

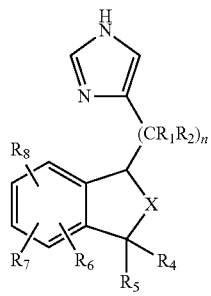

wherein n=0-1, X is 1 or 2 carbon units, $R_4$ is H, OH, alkyl, or alkoxy, $R_5$ may be taken together with $R^4$ to form a carbonyl, and $R^6$-$R^8$=H, OH, SH, alkyl, alkenyl, cycloalkyl, alkoxy, hydroxyalkyl, alkylthio, alkylthiol, halo, $CF_3$, $NO_2$, or alkylamino. This class specifically includes MPV-2426 (fadolmidine) and its prodrug esters:

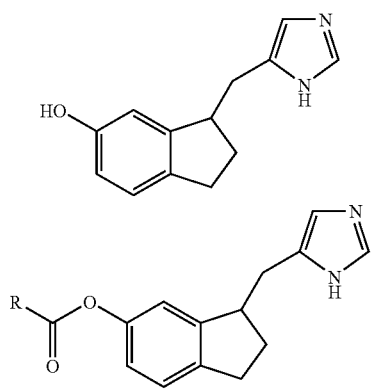

wherein R is optionally substituted lower alkyl, aryl, cycloalkyl, heteroaryl, lower alkylamino, and saturated. 5- or 6-membered heterocyclic groups containing. 1 or 2 N atoms.

Further, other classes of compounds that exhibit functional selectivity for the alpha 2C receptor have been discovered. Application U.S. Ser. No. 11/508,458, filed Aug. 23, 2006, discloses indoline compounds that possess this activity and application U.S. Ser. No. 11/508,467, filed on the same date, describes morpholine compounds that are functionally selective of the alpha 2C receptor. CIP applications of these applications have been filed; the Ser. Nos. are 11/705,673 and 11/705,683, both filed on Feb. 13, 2007.

Additional applications filed concurrently herewith that disclose alpha2C receptor agonists are application U.S. Ser. No. 12/525,648 (now U.S. Pat. No. 8,017,642), which claims priority to provisional application U.S. Ser. No. 60/901,064, and application U.S. Ser. No. 12/525,646, which claims priority to provisional applications U.S. Ser. No. 60/901,070 and 60/972,892.

It has been discovered in accordance with the present invention that adrenergic compounds that act selectively, and preferably even specifically, as agonists of the α2C or the α2B/α2C (hereinafter referred to as α2C or α2B/2C) receptor subtypes in preference over the α2A receptor subtype and that act functionally selectively as agonists of the α2C or the α2B/2C receptor subtype in preference over the α2A receptor subtype possess desirable therapeutic properties associated with adrenergic receptors but without having one or more undesirable side effects such as changes in blood pressure or sedation. For the purposes of the present invention, a compound is defined to be a specific or at least functionally selective agonist of the α2C receptor subtype over the α2A receptor subtype if the compound's efficacy at the α2C receptor is 30% $E_{max}$ (GTPγS assay) and its efficacy at the α2A receptor is 30% $E_{max}$ (GTPγS assay).

There is a need for new compounds, formulations, treatments and therapies to treat diseases and disorders associated with α2C adrenergic receptors while minimizing adverse side effects. Further, there is a need to develop compounds that are functionally selective for the α2C or the α2B/2C receptor subtype with respect to the α2A receptor subtype. It is, therefore, an object of this invention to provide compounds useful in the treatment or prevention or amelioration of such diseases and disorders.

SUMMARY OF THE INVENTION

In its many embodiments, the present invention provides a novel class of heterocyclic compounds as functionally selective α2C adrenergic receptor agonists, or metabolites, stereoisomers, salts, solvates or polymorphs thereof, methods of preparing such compounds, pharmaceutical compositions comprising one or more such compounds, methods of preparing pharmaceutical formulations comprising one or more such compounds, and methods of treatment, prevention, inhibition or amelioration of one or more conditions associated with α2C receptors using such compounds or pharmaceutical compositions.

In one aspect, the present application discloses a compound, or pharmaceutically acceptable salts, esters or metabolites, solvates, prodrugs or polymorphs of said compound, said compound having the general structure shown in the Formula:

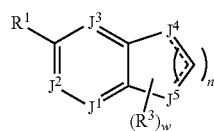

wherein:

$J^1$, $J^2$, and $J^3$ are independently —N—, —N(O)— or —C($R^2$)—;

$J^4$ is:

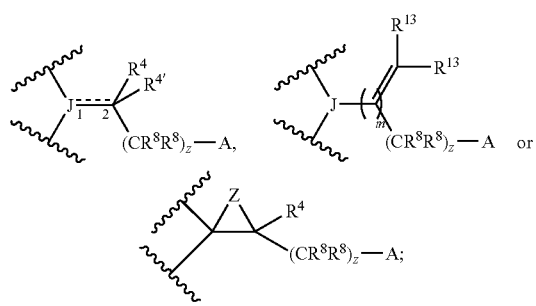

where:

J is —C—, —N—, or —C($R^6$)—;

Z is —[C($R^a$)($R^a$)]$_x$—, where $R^a$ is independently H or alkyl; and x is 1, 2, or 3;

$J^5$ is —C($R^{6'}$)—, —N($R^{6'}$)—, —O— or —S— with the provisio that a double bond is not present between $J^5$ and an adjacent ring atom when $J^5$ is —O— or —S—;

A is a 5-membered heteroaryl, heterocyclyl or heterocyclenyl ring containing 1-3 heteroatoms (preferably independently selected from the group consisting of oxygen, nitrogen and sulphur), and is optionally substituted with at least one $R^5$ and/or 1 or 2 (═O) (carbonyl) groups;

═ is a single or double bond provided that there cannot be two continuous double bonds and further provided that when atoms 1 and 2 form a double bond, $R^{4'}$ is not present;

$R^1$ is a ring selected from the group consisting of cycloalkyl, cycloalkenyl, aryl, heterocyclyl, heterocyclenyl, and heteroaryl, each of which is optionally substituted with at least one (preferably 1 to 5, more preferably 1 to 3) $R^{12}$;

$R^2$ is independently selected from the group consisting of H, —OH, halo, —CN, —NO$_2$, —S(O)$_p R^7$, —$NR^7 R^{7'}$, —(CH$_2$)$_q YR^{7'}$, —(CH$_2$)$_q$N($R^7$)$YR^{7'}$, —(CH$_2$)$_q OYR^{7'}$, and —(CH$_2$)$_q$ON═CR$^7 R^{7'}$, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one (preferably 1 to 5, more preferably 1 to 3) $R^5$;

Y is selected from the group consisting of a bond, —C(═O)—, —C(═O)NR$^7$—, —C(═O)O—, —C(═NR$^7$)—, —C(═NOR$^7$)—, —C(═NR$^7$)NR$^7$—, —C(═NR$^7$)NR$^7$O—, —S(O)$_p$—, —SO$_2$NR$^7$—, and —C(═S)NR$^7$—;

$R^3$ is independently selected from the group consisting of H, halo, and (═O), and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one (preferably 1 to 5, more preferably 1 to 3) $R^5$, provided that when w is 3, no more than 2 of the $R^3$ groups may be (═O);

$R^4$ is selected from the group consisting of H, —CN, and halo, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one (preferably 1 to 5, more preferably 1 to 3) $R^5$;

$R^{4'}$ is absent or selected from the group consisting of H and halo and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one (preferably 1 to 5, more preferably 1 to 3) $R^5$;

$R^5$ is independently selected from the group consisting of H, halo, —OH, —CN, —NO$_2$, —NR$^7 R^{7'}$, and —S(O)$_p R^7$, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups, each of which is optionally substituted with at least one (preferably 1 to 5, more preferably 1 to 3) of halo, —OH, —CN, —NO$_2$, —NR$^7 R^{7'}$, and —S(O)$_p R^7$ substituents and/or 1 or 2 (═O) groups, $R^6$ is independently selected from the group consisting of H, —CN and halo and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups, each of which is optionally substituted with at least one (preferably 1 to 5, more preferably 1 to 3) of halo, —OH, —CN, —NO$_2$, —NR$^7 R^{7'}$, and —S(O)$_p R^7$ substituents and/or 1 or 2 (═O) groups, and —C(═O)$R^7$, —C(═O)O$R^7$, —C(═O)NR$^7 R^{7'}$, —SO$_2 R^7$ and —SO$_2$NR$^7 R^{7'}$;

$R^{6'}$ is independently selected from the group consisting of H and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups, each of which is optionally substituted with at least one (preferably 1 to 5, more preferably 1 to 3) of halo, —OH, —CN, —NO$_2$, —NR$^7 R^{7'}$, and S(O)$_p R^7$ and/or 1 or 2 (═O) groups substituents, and —C(═O)$R^7$, —C(═O)O$R^7$, —C(═O)NR$^7 R^{7'}$, —SO$_2 R^7$ and —SO$_2$NR$^7 R^{7'}$;

$R^7$ is independently selected from the group consisting of H and alkyl, alkenyl, alkynyl, cycloalkyl, cycloalkylalkyl, cycloclenyl, cyclocyclenylalkyl, aryl, arylalkyl, heterocyclyl, heterocyclylalkyl, heterocyclenyl, heterocyclenylalkyl, heteroaryl, and heteroarylalkyl groups, each of which is optionally substituted one or more times (preferably 1 to 5, more preferably 1 to 3) by $R^{12}$;

$R^{7'}$ is independently selected from the group consisting of H and alkyl, alkenyl, alkynyl, cycloalkyl, cycloalkylalkyl, cycloclenyl, cyclocyclenylalkyl, aryl, arylalkyl, heterocyclyl, heterocyclylalkyl, heterocyclenyl, heterocyclenylalkyl, heteroaryl, and heteroarylalkyl groups, each of which is optionally substituted one or more times (preferably 1 to 5, more preferably 1 to 3) by $R^{12}$; or a) when a variable is —NR$^7 R^{7'}$, —C(O)NR$^7 R^{7'}$ or SO$_2$NR$^7 R^{7'}$, $R^7$ and $R^{7'}$ together with the nitrogen atom to which they are attached independently form a 3- to 8-membered heterocyclyl, heterocyclenyl or heteroaryl ring having, in addition to the N atom, 1 or 2 additional hetero atoms independently selected from the group consisting of O, N, —N($R^9$)— and S, wherein said rings are optionally substituted by 1 to 5 independently selected $R^5$ moieties and/or 1 or 2 (═O) groups, or b) when a variable is —(CH$_2$)$_q$ON═CR$^7 R^{7'}$, $R^7$ and $R^{7'}$ together with the carbon atom to which they are attached independently form a 3- to 8-membered cycloalkyl, cycloalkenyl, aryl, heterocyclyl, heterocyclenyl or heteroaryl ring, wherein said hetroacyclyl, heterocyclenyl or heteroaryl rings have 1-3 heteroatoms which are independently selected from the group consisting of O, N, —N(R$^9$)— and S, wherein said rings are optionally substituted by 1 to 5 independently selected R$^5$ moieties and/or 1 or 2 (=O) groups, R$^8$ is independently selected from the group consisting H, alkyl, halo, nitrile, and alkoxy;

R$^9$ is independently selected from the group consisting of H, —C(O)—R$^{10}$, —C(O)—OR$^{10}$, and —S(O)$_p$—OR$^{10}$ and alkyl, alkenyl, alkynyl, cycloalkyl, aryl, arylalkyl, heteroaryl, and heteroarylalkyl groups, each of which is optionally substituted with at least one (preferably 1 to 5, more preferably 1 to 3) of halo, —OH, —CN, —NO$_2$, —N(R$^{11}$)$_2$, and —S(O)$_p$R$^{11}$ substituents and/or 1 or 2 (=O) groups; and R$^{10}$ is independently selected from the group consisting of alkyl, alkenyl, alkynyl, cycloalkyl, aryl, arylalkyl, heteroaryl, and heteroarylalkyl groups, each of which is optionally substituted with at least one (preferably 1 to 5, more preferably 1 to 3) of halo, —OH, —CN, —NO$_2$, —N(R$^{11}$)$_2$, and —S(O)$_p$R$^{11}$ substituents and/or 1 or 2 (=O) groups;

R$^{11}$ is a moiety independently selected from the group consisting of H and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl, each of which is optionally substituted by at least one (preferably 1 to 5, more preferably 1 to 3) substituent independently selected from the group consisting of halo, —OH, —CN, —NO$_2$, —N(R$^{11'}$)$_2$, and —S(O)$_p$R$^{11'}$ and/or 1 or 2 (=O) groups;

R$^{11'}$ is independently selected from the group consisting of H, alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl;

R$^{12}$ is independently selected from selected from the group consisting of H, halo, —OH, —CN, —NO$_2$, —N(R$^{11}$)$_2$, —C(O)—OR$^{14}$, —N(R$^{14}$)—C(O)—R$^{14}$, —N(R$^{14}$)—CO)$_2$—R$^{14}$, —C(O)—N(R$^{11}$)$_2$, —N(R$^{14}$)—S(O)$_2$—R$^{11'}$, —S(O)$_2$—N(R$^{11}$)$_2$ and —S(O)$_p$R$^{11}$ and/or 1 or 2 (=O) groups, and alkyl, alkoxy, alkenyl, alkenyloxy, alkynyl, cycloalkyl, cycloalkenyl, cycloalkoxy, aryl, aryloxy, arylalkyl, heteroaryl, heteroaryloxy, heteroarylalkyl, heterocyclyl, heterocyclenyl, heterocyclenyloxy, heterocyclylalkyl, heterocyclenylalkyl, arylalkoxy, heteroarylalkoxy, heterocyclylalkoxy, and heterocyclenylalkoxy groups, each of which in turn is optionally substituted by at least once (preferably 1 to 5, more preferably 1 to 3) by a substituent selected from the group consisting of H, alkyl, haloalkyl, halo, —OH, optionally substituted alkoxy, optionally substituted aryloxy, optionally substituted cycloalkoxy, optionally substituted heteroaryloxy, optionally substituted heterocyclenyloxy, —CN, —NO$_2$, —N(R$^{11}$)$_2$, and —S(O)$_p$R$^{11}$ and/or 1 or 2 (=O) groups, wherein said optionally substituted alkoxy, aryloxy, optionally substituted cycloalkoxy, optionally substituted heteroaryloxy, and heterocyclenyloxy when substituted are substituted one or more (preferably 1 to 5, more preferably 1 to 3) times by R$^{11}$;

R$^{13}$ is independently selected from the group consisting of H and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one (preferably 1 to 5, more preferably 1 to 3) R$^5$;

R$^{14}$ is independently H, alkyl, or aryl;

m is 0 or 1;

n is independently 1, 2, or 3;

p is independently 0, 1, or 2;

q is independently an integer from 0 to 6;

w is 0, 1, 2, 3, 4, or 5; and z is 0, 1, 2, 3, 4, or 5;

with the following provisos:

(a) if J is N, then J$^5$ is —C(R$^6$)—;

(b) if J$^5$ is O, S or —N(R$^6'$)—, then J is —C— or —C(R$^6$)—;

(c) if m is 0, then z cannot be 0; and (d) if J is —C— or —C(R$^6$)— and J$^5$ is —C(R$^6'$)—, then R$^1$ cannot be cycloalkyl.

Compounds described in the present application include a compound, or pharmaceutically acceptable salts, esters, prodrugs, metabolites, solvates or polymorphs of said compound, said compound having the general structure shown in Formula Ia or Ib:

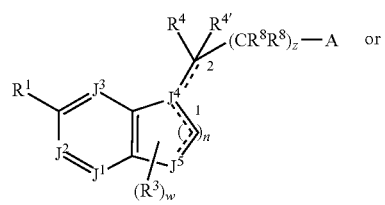

Formula Ia

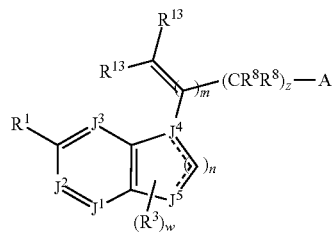

Formula Ib wherein:

A is a 5-membered heteroaryl, heterocyclyl or heterocyclenyl ring containing 1-3 heteroatoms (preferably independently selected from the group consisting of oxygen, nitrogen and sulphur), and is optionally substituted with at least one R$^5$ and/or 1 or 2 (=O) (carbonyl) groups;

J$^1$, J$^2$, and J$^3$ are independently —N—, —N(O)— or —C(R$^2$)—;

J$^4$ is C, N, or —C(R$^6$)—;

J$^5$ is —C(R$^6'$)—, —N(R$^6'$)—, —O— or —S—; with the proviso that a double bond is not present between J$^5$ and an adjacent ring atom when J$^5$ is —O— or —S—.

= is a single or double bond provided that there cannot be two continuous double bonds and further provided that when atoms 1 and 2 form a double bond, R$^{4'}$ is not present;

R$^1$ is a ring selected from the group consisting of cycloalkyl, cycloalkenyl, aryl, heterocyclyl, heterocyclenyl, and heteroaryl, each of which is optionally substituted with at least one (preferably 1 to 5, more preferably 1 to 3) R$^{12}$;

R$^2$ is independently selected from the group consisting of H, —OH, halo, —CN, —NO$_2$, —S(O)$_p$R$^7$, —NR$^7$R$^{7'}$, —(CH$_2$)$_q$YR$^{7'}$, —(CH$_2$)$_q$N(R$^7$)YR$^{7'}$, —(CH$_2$)$_q$OYR$^{7'}$, and —(CH$_2$)$_q$ON=CR$^7$R$^{7'}$, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one (preferably 1 to 5, more preferably 1 to 3) R$^5$;

Y is selected from the group consisting of a bond, —C(=O)—, —C(=O)NR$^7$—, —C(=O)O—, —C(=NR$^7$)—, —C(=NOR$^7$)—, —C(=NR$^7$)NR$^7$—, —C(=NR$^7$)NR$^7$O—, —S(O)$_p$—, —SO$_2$NR$^7$—, and —C(=S)NR$^7$—;

R$^3$ is independently selected from the group consisting of H, halo, and (=O), and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one (preferably 1 to 5, more preferably 1 to 3) R$^5$, provided that when w is 3, no more than 2 of the R$^3$ groups may be (=O);

R$^4$ is absent or selected from the group consisting of H, —CN, and halo, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one (preferably 1 to 5, more preferably 1 to 3) R$^5$;

R$^{4'}$ is selected from the group consisting of H and halo and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one (preferably 1 to 5, more preferably 1 to 3) R$^5$;

R$^5$ is independently selected from the group consisting of H, halo, —OH, —CN, —NO$_2$, —NR$^7$R$^{7'}$, and —S(O)$_p$R$^7$, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups, each of which is optionally substituted with at least one (preferably 1 to 5, more preferably 1 to 3) of halo, —OH, —CN, —NO$_2$, —NR$^7$R$^{7'}$, and —S(O)$_p$R$^7$ substituents and/or 1 or 2 (=O) groups, R$^6$ is independently selected from the group consisting of H, —CN, and halo and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups, each of which is optionally substituted with at least one (preferably 1 to 5, more preferably 1 to 3) of halo, —OH, —CN, —NO$_2$, —NR$^7$R$^{7'}$, and —S(O)$_p$R$^7$ substituents and/or 1 or 2 (=O) groups, and —C(=O)R$^7$, —C(=O)OR$^7$, —C(=O)NR$^7$R$^{7'}$, —SO$_2$R$^7$ and —SO$_2$NR$^7$R$^{7'}$;

or, R$^4$ and R$^6$ taken together with the carbon atoms to which they are attached form a 3- to 6-membered cycloalkyl, cycloalkenyl, heterocyclyl or heterocyclenyl ring, wherein said rings may be optionally substituted one or more times (preferably 1 to 5, more preferably 1 to 3) by R$^5$ and/or 1 or 2 (=O) groups;

R$^{6'}$ is independently selected from the group consisting of H and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups, each of which is optionally substituted with at least one (preferably 1 to 5, more preferably 1 to 3) of halo, —OH, —CN, —NO$_2$, —NR$^7$R$^{7'}$, and —S(O)$_p$R$^7$ and/or 1 or 2 (=O) groups substituents, and —C(=O)R$^7$, —C(=O)OR$^7$, —C(=O)NR$^7$R$^{7'}$, —SO$_2$R$^7$ and —SO$_2$NR$^7$R$^{7'}$;

R$^7$ is independently selected from the group consisting of H and alkyl, alkenyl, alkynyl, cycloalkyl, cycloalkylalkyl, cycloclenyl, cyclocyclenylalkyl, aryl, arylalkyl, heterocyclyl, heterocyclylalkyl, hetrocyclenyl, hetrocyclenylalkyl, heteroaryl, and heteroarylalkyl groups, each of which is optionally substituted one or more times (preferably 1 to 5, more preferably 1 to 3) by R$^{12}$;

R$^{7'}$ is independently selected from the group consisting of H and alkyl, alkenyl, alkynyl, cycloalkyl, cycloalkylalkyl, cycloclenyl, cyclocyclenylalkyl, aryl, arylalkyl, heterocyclyl, heterocyclylalkyl, hetrocyclenyl, hetrocyclenylalkyl, heteroaryl, and heteroarylalkyl groups, each of which is optionally substituted one or more times (preferably 1 to 5, more preferably 1 to 3) by R$^{12}$; or a) when a variable is —NR$^7$R$^{7'}$, —C(O)NR$^7$R$^{7'}$ or SO$_2$NR$^7$R$^{7'}$, R$^7$ and R$^{7'}$ together with the nitrogen atom to which they are attached independently form a 3- to 8-membered heterocyclyl, heterocyclenyl or heteroaryl ring having, in addition to the N atom, 1 or 2 additional hetero atoms independently selected from the group consisting of O, N, —N(R$^9$)— and S, wherein said rings are optionally substituted by 1 to 5 independently selected R$^5$ moieties and/or 1 or 2 (=O) groups, or b) when a variable is —(CH$_2$)$_q$ON=CR$^7$R$^{7'}$, R$^7$ and R$^{7'}$ together with the carbon atom to which they are attached independently form a 3- to 8-membered cycloalkyl, cycloalkenyl, aryl, heterocyclyl, heterocyclenyl or heteroaryl ring, wherein said hetroacyclyl, heterocyclenyl or heteroaryl rings have 1-3 heteroatoms which are independently selected from the group consisting of O, N, —N(R$^9$)— and S, wherein said rings are optionally substituted by 1 to 5 independently selected R$^5$ moieties and/or 1 or 2 (=O) groups, R$^8$ is independently selected from the group consisting H, alkyl, halo, nitrile, and alkoxy;

R$^9$ is independently selected from the group consisting of H, —C(O)—R$^{10}$, —C(O)—OR$^{10}$, and —S(O)$_p$—OR$^{10}$ and alkyl, alkenyl, alkynyl, cycloalkyl, aryl, arylalkyl, heteroaryl, and heteroarylalkyl groups, each of which is optionally substituted with at least one (preferably 1 to 5, more preferably 1 to 3) of halo, —OH, —CN, —NO$_2$, —N(R$^{11}$)$_2$, and —S(O)$_p$R$^{11}$ substituents and/or 1 or 2 (=O) groups; and R$^{10}$ is independently selected from the group consisting of alkyl, alkenyl, alkynyl, cycloalkyl, aryl, arylalkyl, heteroaryl, and heteroarylalkyl groups, each of which is optionally substituted with at least one (preferably 1 to 5, more preferably 1 to 3) of halo, —OH, —CN, —NO$_2$, —N(R$^{11}$)$_2$, and —S(O)$_p$R$^{11}$ substituents and/or 1 or 2 (=O) groups;

R$^{11}$ is a moiety independently selected from the group consisting of H and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl, each of which is optionally substituted by at least one (preferably 1 to 5, more preferably 1 to 3) substituent independently selected from the group consisting of halo, —OH, —CN, —NO$_2$, —N(R$^{11'}$)$_2$, and —S(O)$_p$R$^{11'}$ and/or 1 or 2 (=O) groups;

R$^{11'}$ is independently selected from the group consisting of H, alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl;

R$^{12}$ is independently selected from selected from the group consisting of H, halo, —OH, —CN, —NO$_2$, —N(R$^{11}$)$_2$, —C(O)—OR$^{14}$, —N(R$^{14}$)—C(O)—R$^{14}$, —N(R$^{14}$)—C(O)$_2$—R$^{14}$, C(O)—N(R$^{11}$)$_2$)—N(R$^{14}$)—S(O)$_2$—R$^{11'}$, —S(O)$_2$—N(R$^{11}$)$_2$ and —S(O)$_p$R$^{11}$ and/or 1 or 2 (=O) groups, and alkyl, alkoxy, alkenyl, alkenyloxy, alkynyl, cycloalkyl, cycloalkenyl, cycloalkoxy, aryl, aryloxy, arylalkyl, heteroaryl, heteroaryloxy, heteroarylalkyl, heterocyclyl, heterocyclenyl, heterocyclenyloxy, heterocyclylalkyl, heterocyclenylalkyl, arylalkoxy, heteroarylalkoxy, heterocyclylalkoxy, and heterocyclenylalkoxy groups, each of which in turn is optionally substituted by at least once (preferably 1 to 5, more preferably 1 to 3) by a substituent selected from the group consisting of H, alkyl, haloalkyl, halo, —OH, optionally substituted alkoxy, optionally substituted aryloxy, optionally substituted cycloalkoxy, optionally substituted heteroaryloxy, optionally substituted heterocyclenyloxy, —CN, —NO$_2$, —N(R$^{11}$)$_2$, and —S(O)$_p$R$^{11}$ and/or 1 or 2 (═O) groups, wherein said optionally substituted alkoxy, aryloxy, optionally substituted cycloalkoxy, optionally substituted heteroaryloxy, and heterocyclenyloxy when substituted are substituted one or more (preferably 1 to 5, more preferably 1 to 3) times by R$^{11}$;

R$^{13}$ is independently selected from the group consisting of H and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one (preferably 1 to 5, more preferably 1 to 3) R$^5$;

m is 0 or 1;
n is independently 1, 2, or 3;
p is independently 0, 1, or 2;
q is independently an integer from 0-6;
w is an integer from 0-5; and
z is an integer from 0-5
with the following provisos:
(a) if J$^4$ is N, then J$^5$ is —C(R$^{6'}$)—;
(b) if J$^5$ is O, S or —N(R$^{6'}$)—, then J$^4$ is —C— or —C(R$^6$)—;
(c) if m is 0, then z cannot be 0; and
(d) if J$^4$ is —C— or —C(R$^6$)— and J$^5$ is —C(R$^{6'}$)—, then R$^1$ cannot be cycloalkyl.

The compounds of Formula I (including those of formulae Ia and IIb) can be useful as α2C adrenergic receptor agonists, and can be useful in the treatment and prevention of allergic rhinitis, congestion (including, but not limited to nasal congestion), migraine, congestive heart failure, cardiac ischemia, glaucoma, stress-induced urinary incontence, attention deficit hyperactivity disorder, neuronal damage from ischemia and psychotic disorders. Further, the compounds of Formulae Ia and Ib can be useful in the treatment of pain (both chronic and acute), such as pain that is caused by inflammation, neuropathy, arthritis (including osteo and rheumatoid arthritis), diabetes (e.g., diabetes mellitus or diabetes insipidus) or pain of an unknown origin. Examples of neuropathic pain may include but not limited to; diabetic neuropathy, neuralgia of any etiology (e.g. post-herpetic, trigeminal), chemotherapy-induced neuropathy, HIV, lower back pain of neuropathic origin (e.g. sciatica), traumatic peripheral nerve injury of any etiology, central pain (e.g. post-stroke, thalamic, spinal nerve injury). Other pain that can be treated is nociceptive pain and pain that is visceral in origin or pain that is secondary to inflammation or nerve damage in other diseases or diseases of unknown origin. Further, the compounds of Formula I (including those of Formulae Ia and Ib) can be useful in the treatment of symptoms of diabetes. Examples of symptoms of diabetes may include but are not limited to: hyperglycemia, hypertriglyceridemia, increased levels of blood insulin and hyperlipidemia.

Alternatively, the present invention provides for a method for the treatment of congestion in a mammal in need thereof which comprises administering to a mammal an effective dose of at least one compound having adrenergic activity wherein said compound is a functionally selective agonist of the α2c receptor.

A further embodiment of the present invention is a method for the treatment of congestion in a mammal in need thereof which comprises administering to a mammal an effective dose of at least one compound having adrenergic activity wherein said compound is a functionally selective agonist of the α2C receptor, wherein the selective agonist of the α2c receptor has an efficacy that is greater than or equal to 30% E$_{max}$ when assayed in the GTPγS assay and its efficacy at the α2A receptor is ≦30% E$_{max}$ (GTPγS assay).

Another embodiment of the present invention is a method for the treatment of congestion in a mammal in need thereof without modifying the blood pressure at therapeutic doses which comprises administering to the mammal an effective dose of at least one compound having adrenergic activity wherein said compound is a selective agonist of the α2C receptor.

DETAILED DESCRIPTION

In an embodiment, the present invention discloses certain heterocyclic compounds which are represented by structural Formula I, or a pharmaceutically acceptable salt or solvate thereof, wherein the various moieties are as described above.

In one embodiment, the present invention discloses compounds of Formula Ia which are represented by the structural Formula Ia Formula Ia or a pharmaceutically acceptable salt, ester, solvate or prodrug thereof, wherein:

A is a 5-membered heteroaryl, heterocyclyl or heterocyclenyl ring containing 1-3 heteroatoms, and is optionally substituted with at least one R$^5$ and/or 1 or 2 (═O) (carbonyl) groups;

J$^1$, J$^2$, and J$^3$ are independently —N—, —N(O)— or —C(R$^2$)—;

J is C, N, or —C(R$^6$)—;

J$^5$ is —C(R$^{6'}$)—, —N(R$^{6'}$)—, —O— or —S— with the proviso that a double bonds is not present between J$^5$ and an adjacent ring atom when J$^5$ is —O— or —S—;

═ is a single or double bond provided that there cannot be two continuous double bonds and further provided that when atoms 1 and 2 form a double bond, R$^{4'}$ is not present;

R$^1$ is a ring selected from the group consisting of cycloalkyl, cycloalkenyl, aryl, heterocyclyl, heterocyclenyl, and heteroaryl, each of which is optionally substituted with at least one R$^{12}$;

R$^2$ is independently selected from the group consisting of H, —OH, halo, —CN, —NO$_2$, —S(O)$_p$R$^7$, —NR$^7$R$^{7'}$, —(CH$_2$)$_q$YR$^{7'}$, —(CH$_2$)$_q$N(R$^7$)YR$^{7'}$, —(CH$_2$)$_q$OYR$^{7'}$, and —(CH$_2$)$_q$ON═CR$^7$R$^{7'}$, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one R$^5$;

Y is selected from the group consisting of a bond, —C(═O)—, —C(═O)NR$^7$—, —C(═O)O—, —C(═NR$^7$)—, —C(═NOR$^7$)—, —C(═NR$^7$)NR$^7$—, —C(═NR$^7$)NR$^7$O—, —S(O)$_p$—, —SO$_2$NR$^7$—, and —C(═S)NR$^7$—;

R$^3$ is independently selected from the group consisting of H, halo, and (═O), and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one $R^5$, provided that when w is 3, no more than 2 of the $R^3$ groups may be (=O);

$R^4$ is selected from the group consisting of H, —CN, and halo, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one $R^5$;

$R^{4'}$ is absent or selected from the group consisting of H and halo, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one $R^5$;

$R^5$ is independently selected from the group consisting of H, halo, —OH, —CN, —NO$_2$, —NR$^7$R$^{7'}$, and —S(O)$_p$R$^7$, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups, each of which is optionally substituted with at least one of halo, —OH, —CN, —NO$_2$, —NR$^7$R$^{7'}$, and —S(O)$_p$R$^7$ substituents and/or 1 or 2 (=O) groups, $R^6$ is independently selected from the group consisting of H, —CN and halo, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups, each of which is optionally substituted with at least one of halo, —OH, —CN, —NO$_2$, —NR$^7$R$^{7'}$, and —S(O)$_p$R$^7$ substituents and/or 1 or 2 (=O) groups, and —C(=O)R$^7$, —C(=O)OR$^7$, —C(=O)NR$^7$R$^{7'}$, —SO$_2$R$^7$ and —SO$_2$N1R$^7$R$^{7'}$;

$R^{6'}$ is independently selected from the group consisting of H and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups, each of which is optionally substituted with at least one of halo, —OH, —CN, —NO$_2$, —NR$^7$R$^{7'}$, and —S(O)$_p$R$^7$ and/or 1 or 2 (=O) groups substituents, and —C(=O)R$^7$, —C(=O)OR$^7$, —C(=O)NR$^7$R$^{7'}$, —SO$_2$R$^7$ and —SO$_2$NR$^7$R$^{7'}$;

$R^7$ is independently selected from the group consisting of H and alkyl, alkenyl, alkynyl, cycloalkyl, cycloalkylalkyl, cycloclenyl, cyclocyclenylalkyl, aryl, arylalkyl, heterocyclyl, heterocyclylalkyl, hetrocyclenyl, hetrocyclenylalkyl, heteroaryl, and heteroarylalkyl groups, each of which is optionally substituted one or more times by $R^{12}$;

$R^{7'}$ is independently selected from the group consisting of H and alkyl, alkenyl, alkynyl, cycloalkyl, cycloalkylalkyl, cycloclenyl, cyclocyclenylalkyl, aryl, arylalkyl, heterocyclyl, heterocyclylalkyl, hetrocyclenyl, hetrocyclenylalkyl, heteroaryl, and heteroarylalkyl groups, each of which is optionally substituted one or more times by $R^{12}$; or a) when a variable is —NR$^7$R$^{7'}$, —C(O)NR$^7$R$^{7'}$ or SO$_2$NR$^7$R$^{7'}$, R$^7$ and R$^{7'}$ together with the nitrogen atom to which they are attached independently form a 3- to 8-membered heterocyclyl, heterocyclenyl or heteroaryl ring having, in addition to the N atom, 1 or 2 additional hetero atoms independently selected from the group consisting of O, N, —N(R$^9$)— and S, wherein said rings are optionally substituted by 1 to 5 independently selected R$^5$ moieties and/or 1 or 2 (=O) groups, or b) when a variable is —(CH$_2$)$_q$ON=CR$^7$R$^{7'}$, R$^7$ and R$^{7'}$ together with the carbon atom to which they are attached independently form a 3- to 8-membered cycloalkyl, cycloalkenyl, aryl, heterocyclyl, heterocyclenyl or heteroaryl ring, wherein said hetroacyclyl, heterocyclenyl or heteroaryl rings have 1-3 heteroatoms which are independently selected from the group consisting of O, N, —N(R$^9$)— and S, wherein said rings are optionally substituted by 1 to 5 independently selected R$^5$ moieties and/or 1 or 2 (=O) groups, $R^8$ is independently selected from the group consisting H, alkyl, halo, nitrile, and alkoxy;

$R^9$ is independently selected from the group consisting of H, —C(O)—R$^{10}$, —C(O)—OR$^{10}$, and —S(O)$_p$—OR$^{10}$ and alkyl, alkenyl, alkynyl, cycloalkyl, aryl, arylalkyl, heteroaryl, and heteroarylalkyl groups, each of which is optionally substituted with at least one of halo, —OH, —CN, —NO$_2$, —N(R$^{11}$)$_2$, and —S(O)$_p$R$^{11}$ substituents and/or 1 or 2 (=O) groups; and $R^{10}$ is independently selected from the group consisting of alkyl, alkenyl, alkynyl, cycloalkyl, aryl, arylalkyl, heteroaryl, and heteroarylalkyl groups, each of which is optionally substituted with at least one of halo, —OH, —CN, —NO$_2$, —N(R$^{11}$)$_2$, and —S(O)$_p$R$^{11}$ substituents and/or 1 or 2 (=O) groups;

$R^{11}$ is a moiety independently selected from the group consisting of H and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl, each of which is optionally substituted by at least one substituent independently selected from the group consisting of halo, —OH, —CN, —NO$_2$, —N(R$^{11}$)$_2$, and —S(O)$_p$R$^{11'}$ and/or 1 or 2 (=O) groups;

$R^{11'}$ is independently selected from the group consisting of H, alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl;

$R^{12}$ is independently selected from selected from the group consisting of H, halo, —OH, —CN, —NO$_2$, —N(R$^{11}$)$_2$, —C(O)—OR$^{14}$, —N(R$^{14}$)—C(O)—R$^{14}$, —N(R$^{14}$)—C(O)$_2$—R$^{14}$, —C(O)—N(R$^{11}$)$_2$, —N(R$^{14}$)—S(O)$_2$—R$^{11}$, —S(O)$_2$—N(R$^{11}$)$_2$ and —S(O)$_p$R$^{11}$ and/or 1 or 2 (=O) groups, and alkyl, alkoxy, alkenyl, alkenyloxy, alkynyl, cycloalkyl, cycloalkenyl, cycloalkoxy, aryl, aryloxy, arylalkyl, heteroaryl, heteroaryloxy, heteroarylalkyl, heterocyclyl, heterocyclenyl, heterocyclenyloxy, heterocyclylalkyl, heterocyclenylalkyl, arylalkoxy, heteroarylalkoxy, heterocyclylalkoxy, and heterocyclenylalkoxy groups, each of which in turn is optionally substituted by at least once by a substituent selected from the group consisting of H, alkyl, haloalkyl, halo, —OH, optionally substituted alkoxy, optionally substituted aryloxy, optionally substituted cycloalkoxy, optionally substituted heteroaryloxy, optionally substituted heterocyclenyloxy, —CN, —NO$_2$, —N(R$^{11}$)$_2$, and —S(O)$_p$R$^{11}$ and/or 1 or 2 (=O) groups, wherein said optionally substituted alkoxy, aryloxy, optionally substituted cycloalkoxy, optionally substituted heteroaryloxy, and heterocyclenyloxy when substituted are substituted one or more times by R$^{11}$;

$R^{14}$ is independently H, alkyl, or aryl;

m is 0 or 1;

n is independently 1, 2 or 3;

p is independently 0-2;

q is independently an integer from 0-6;

w is 0, 1, 2, 3, 4, or 5; and z is 0, 1, 2, 3, 4, or 5, with the following provisos:

(a) if J is N, then J$^5$ is —C(R$^{6'}$)—;

(b) if J$^5$ is O, S or —N(R$^{6'}$)—, then J is —C— or —C(R$^6$)—;

(c) if m is 0, then z cannot be 0; and (d) if J is —C— or —C(R$^6$)— and J$^5$ is —C(R$^{6'}$)—, then R$^1$ cannot be cycloalkyl.

In another embodiment, the present invention discloses compounds of Formula I which are represented by the structural Formula Ib Formula Ib

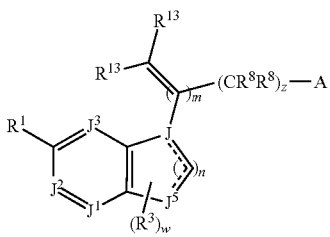

or a pharmaceutically acceptable salt, ester, solvate or prodrug thereof, wherein:

A is a 5-membered heteroaryl, heterocyclyl or heterocyclenyl ring containing 1-3 heteroatoms, and is optionally substituted with at least one $R^5$ and/or 1 or 2 (=O) (carbonyl) groups;

$J^1$, $J^2$, and $J^3$ are independently —N—, —N(O)— or —C($R^2$)—;

J is C, N, or C($R^6$)—;

$J^5$ is —C($R^{6'}$)—, —N($R^{6'}$)—, —O— or —S—, with the proviso that a double bond is not present between $J^5$ and an adjacent ring atom when $J^5$ is —O— or —S—;

═ is a single or double bond provided that there cannot be two continuous double bonds;

$R^1$ is a ring selected from the group consisting of cycloalkyl, cycloalkenyl, aryl, heterocyclyl, heterocyclenyl, and heteroaryl, each of which is optionally substituted with at least one $R^{12}$;

$R^2$ is independently selected from the group consisting of H, —OH, halo, —CN, —NO$_2$, —S(O)$_p R^7$, —NR$^7 R^{7'}$, —(CH$_2$)$_p$YR$^{7'}$, —(CH$_2$)$_q$N(R$^7$)YR$^{7'}$, —(CH$_2$)$_p$OYR$^{7'}$, and —(CH$_2$)$_q$ON═CR$^7 R^{7'}$, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one $R^5$;

Y is selected from the group consisting of a bond, —C(═O)—, —C(═O)NR$^7$—, —C(═O)O—, —C(═NR$^7$)—, —C(═NOR$^7$)—, —C(═NR$^7$)NR$^7$—, —C(═NR$^7$)NR$^7$O—, —S(O)$_p$—, —SO$_2$NR$^7$—, and —C(═S)NR$^7$—;

$R^3$ is independently selected from the group consisting of H, halo, and (═O), and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one $R^5$, provided that when w is 3, no more than 2 of the $R^3$ groups may be (═O);

$R^5$ is independently selected from the group consisting of H, halo, —OH, —CN, —NO$_2$, —NR$^7 R^{7'}$, and —S(O)$_p R^7$, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups, each of which is optionally substituted with at least one of halo, —OH, —CN, —NO$_2$, —NR$^7 R^{7'}$, and —S(O)$_p R^7$ substituents and/or 1 or 2 (═O) groups, $R^6$ is independently selected from the group consisting of H, —CN, and halo, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups, each of which is optionally substituted with at least one of halo, —OH, —CN, —NO$_2$, —NR$^7 R^{7'}$, and —S(O)$_p R^7$ substituents and/or 1 or 2 (═O) groups, and —C(═O)R$^7$, —C(═O)OR$^7$, —C(═O)NR$^7 R^{7'}$, —SO$_2 R^7$ and —SO$_2$NR$^7 R^{7'}$;

$R^{6'}$ is independently selected from the group consisting of H and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups, each of which is optionally substituted with at least one of halo, —OH, —CN, —NO$_2$, —NR$^7 R^{7'}$, and —S(O)$_p R^7$ and/or 1 or 2 (═O) groups substituents, and —C(═O)R$^7$, —C(═O)OR$^7$, —C(═O)NR$^7 R^{7'}$, —SO$_2 R^7$ and —SO$_2$NR$^7 R^{7'}$;

$R^7$ is independently selected from the group consisting of H and alkyl, alkenyl, alkynyl, cycloalkyl, cycloalkylalkyl, cycloclenyl, cyclocyclenylalkyl, aryl, arylalkyl, heterocyclyl, heterocyclylalkyl, hetrocyclenyl, hetrocyclenylalkyl, heteroaryl, and heteroarylalkyl groups, each of which is optionally substituted one or more times by $R^{12}$;

$R^{7'}$ is independently selected from the group consisting of H and alkyl, alkenyl, alkynyl, cycloalkyl, cycloalkylalkyl, cycloclenyl, cyclocyclenylalkyl, aryl, arylalkyl, heterocyclyl, heterocyclylalkyl, hetrocyclenyl, hetrocyclenylalkyl, heteroaryl, and heteroarylalkyl groups, each of which is optionally substituted one or more times by $R^{12}$; or a) when a variable is —NR$^7 R^{7'}$, —C(O)NR$^7 R^{7'}$ or —SO$_2$NR$^7 R^{7'}$, $R^7$ and $R^{7'}$ together with the nitrogen atom to which they are attached independently form a 3- to 8-membered heterocyclyl, heterocyclenyl or heteroaryl ring having, in addition to the N atom, 1 or 2 additional hetero atoms independently selected from the group consisting of O, N, —N($R^9$)— and S, wherein said rings are optionally substituted by 1 to 5 independently selected $R^5$ moieties and/or 1 or 2 (═O) groups, or b) when a variable is —(CH$_2$)$_q$ON═CR$^7 R^{7'}$, $R^7$ and $R^{7'}$ together with the carbon atom to which they are attached independently form a 3- to 8-membered cycloalkyl, cycloalkenyl, aryl, heterocyclyl, heterocyclenyl or heteroaryl ring, wherein said hetroacyclyl, heterocyclenyl or heteroaryl rings have 1-3 heteroatoms which are independently selected from the group consisting of O, N, —N($R^9$)— and S, wherein said rings are optionally substituted by 1 to 5 independently selected $R^5$ moieties and/or 1 or 2 (═O) groups, $R^8$ is independently selected from the group consisting H, alkyl, halo, nitrile, and alkoxy;

$R^9$ is independently selected from the group consisting of H, —C(O)—R$^{10}$, —C(O)—OR$^{10}$, and —S(O)$_p$—OR$^{10}$ and alkyl, alkenyl, alkynyl, cycloalkyl, aryl, arylalkyl, heteroaryl, and heteroarylalkyl groups, each of which is optionally substituted with at least one of halo, —OH, —CN, —NO$_2$, —N($R^{11}$)$_2$, and —S(O)$_p R^{11}$ substituents and/or 1 or 2 (═O) groups; and $R^{10}$ is independently selected from the group consisting of alkyl, alkenyl, alkynyl, cycloalkyl, aryl, arylalkyl, heteroaryl, and heteroarylalkyl groups, each of which is optionally substituted with at least one of halo, —OH, —CN, —NO$_2$, —N($R^{11}$)$_2$, and —S(O)$_p R^{11}$ substituents and/or 1 or 2 (═O) groups;

$R^{11}$ is a moiety independently selected from the group consisting of H and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl, each of which is optionally substituted by at least one substituent independently selected from the group consisting of halo, —OH, —CN, —NO$_2$, —N($R^{11'}$)$_2$, and —S(O)$_p R^{11'}$ and/ or 1 or 2 (═O) groups;

$R^{11'}$ is independently selected from the group consisting of H, alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl;

$R^{12}$ is independently selected from selected from the group consisting of H, halo, —OH, —CN, —NO$_2$, —N(R$^{11}$)$_2$, —C(O)—OR$^{14}$, —N(R$^{14}$)—C(O)—R$^{14}$, —N(R$^{14}$)—C(O)$_2$—R$^{14}$, —C(O)—N(R$^{11}$)$_2$, —N(R$^{14}$)—S(O)$_2$—R$^{11'}$, —S(O)$_2$—N(R$^{11}$)$_2$ and —S(O)$_p$R$^{11}$ and/or 1 or 2 (═O) groups, and alkyl, alkoxy, alkenyl, alkenyloxy, alkynyl, cycloalkyl, cycloalkenyl, cycloalkoxy, aryl, aryloxy, arylalkyl, heteroaryl, heteroaryloxy, heteroarylalkyl, heterocyclyl, heterocyclenyl, heterocyclenyloxy, heterocyclylalkyl, heterocyclenylalkyl, arylalkoxy, heteroarylalkoxy, heterocyclylalkoxy, and heterocyclenylalkoxy groups, each of which in turn is optionally substituted by at least once by a substituent selected from the group consisting of H, alkyl, haloalkyl, halo, —OH, optionally substituted alkoxy, optionally substituted aryloxy, optionally substituted cycloalkoxy, optionally substituted heteroaryloxy, optionally substituted heterocyclenyloxy, —CN, —NO$_2$, —N(R$^{11}$)$_2$, and —S(O)$_p$R$^{11}$ and/or 1 or 2 (═O) groups, wherein said optionally substituted alkoxy, aryloxy, optionally substituted cycloalkoxy, optionally substituted heteroaryloxy, and heterocyclenyloxy when substituted are substituted one or more times by R$^{11}$;

$R^{13}$ is independently selected from the group consisting of H and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one R$^5$;

$R^{14}$ is independently H, alkyl, or aryl;

m is 0 or 1;

n is independently 1, 2, or 3;

p is independently 0, 1, or 2;

q is independently an integer from 0-6;

w is 0, 1, 2, 3, 4, or 5; and z is 0, 1, 2, 3, 4, or 5 with the following provisos:

(a) if J is N, then J$^5$ is —C(R$^{6'}$)—;

(b) if J$^5$ is O, S or —N(R$^{6'}$)—, then J is —C— or —C(R$^6$)—;

(c) if m is 0, then z cannot be 0; and (d) if J is —C— or —C(R$^6$)— and J$^5$ is —C(R$^{6'}$)—, then R$^1$ cannot be cycloalkyl.

In another embodiment, the present invention discloses compounds of Formula I which is represented by the structural Formula Ic

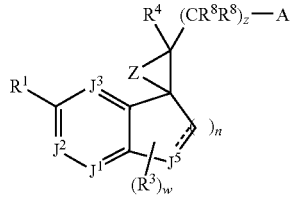

Ic or a pharmaceutically acceptable salt, ester, solvate or prodrug thereof,
wherein:

A is a 5-membered heteroaryl, heterocyclyl or heterocyclenyl ring containing 1-3 heteroatoms, and is optionally substituted with at least one R$^5$ and/or 1 or 2 (═O) (carbonyl) groups;

J$^1$, J$^2$, and J$^3$ are independently —N—, —N(O)— or —C(R$^2$)—;

J$^5$ is —C(R$^{6'}$)—, —N(R$^{6'}$)—, —O— or —S—, with the proviso that a double bond is not present between J$^5$ and an adjacent ring atom when J$^5$ is —O— or —S—;

═ is a single or double bond provided that there cannot be two continuous double bonds;

$R^1$ is a ring selected from the group consisting of cycloalkyl, cycloalkenyl, aryl, heterocyclyl, heterocyclenyl, and heteroaryl, each of which is optionally substituted with at least one R$^{12}$;

$R^2$ is independently selected from the group consisting of H, —OH, halo, —CN, —NO$_2$, —S(O)$_p$R$^7$, —NR$^7$R$^{7'}$, —(CH$_2$)$_q$YR$^{7'}$, —(CH$_2$)$_p$N(R$^7$)YR$^{7'}$, —(CH$_2$)$_p$OYR$^{7'}$, and —(CH$_2$)$_q$ON═CR$^7$R$^{7'}$, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one R$^5$;

Y is selected from the group consisting of a bond, —C(═O)—, —C(═O)NR$^7$—, —C(═O)O—, —C(═NR$^7$)—, —C(═NOR$^7$)—, —C(═NR$^7$)NR$^7$—, —C(═NR$^7$)NR$^7$O—, —S(O)$_p$—, —SO$_2$NR$^7$—, and —C(═S)NR$^7$—;

$R^3$ is independently selected from the group consisting of H, halo, and (═O), and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one R$^5$, provided that when w is 3, no more than 2 of the R$^3$ groups may be (═O);

$R^4$ is selected from the group consisting of H, —CN, and halo, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one R$^5$;

$R^5$ is independently selected from the group consisting of H, halo, —OH, —CN, —NO$_2$, —NR$^7$R$^{7'}$, and —S(O)$_p$R$^7$, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups, each of which is optionally substituted with at least one of halo, —OH, —CN, —NO$_2$, —NR$^7$R$^{7'}$, and —S(O)$_p$R$^7$ substituents and/or 1 or 2 (═O) groups, $R^{6'}$ is independently selected from the group consisting of H, —CN and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups, each of which is optionally substituted with at least one of halo, —OH, —CN, —NO$_2$, —NR$^7$R$^{7'}$, and —S(O)$_p$R$^7$ and/or 1 or 2 (═O) groups substituents, and —C(═O)R$^7$, —C(═O)OR$^7$, —C(═O)NR$^7$R$^{7'}$, —SO$_2$R$^7$ and —SO$_2$NR$^7$R$^{7'}$;

$R^7$ is independently selected from the group consisting of H and alkyl, alkenyl, alkynyl, cycloalkyl, cycloalkylalkyl, cycloclenyl, cyclocyclenylalkyl, aryl, arylalkyl, heterocyclyl, heterocyclylalkyl, hetrocyclenyl, heterocyclenylalkyl, heteroaryl, and heteroarylalkyl groups, each of which is optionally substituted one or more times by R$^{12}$;

$R^{7'}$ is independently selected from the group consisting of H and alkyl, alkenyl, alkynyl, cycloalkyl, cycloalkylalkyl, cycloclenyl, cyclocyclenylalkyl, aryl, arylalkyl, heterocyclyl, heterocyclylalkyl, hetrocyclenyl, hetrocyclenylalkyl, heteroaryl, and heteroarylalkyl groups, each of which is optionally substituted one or more times by R$^{12}$; or a) when a variable is —NR$^7$R$^{7'}$, —C(O)NR$^7$R$^{7'}$ or SO$_2$NR$^7$R$^{7'}$, R$^7$ and R$^{7'}$ together with the nitrogen atom to which they are attached independently form a 3- to 8-membered heterocyclyl, heterocyclenyl or heteroaryl ring having, in addition to the N atom, 1 or 2 additional hetero atoms independently selected from the group consisting of O, N, —N(R$^9$)— and S, wherein said rings are optionally substituted by 1 to 5 independently selected $R^5$ moieties and/or 1 or 2 (=O) groups, or b) when a variable is —(CH$_2$)$_q$ON=CR$^7$R$^{7'}$, R$^7$ and R$^{7'}$ together with the carbon atom to which they are attached independently form a 3- to 8-membered cycloalkyl, cycloalkenyl, aryl, heterocyclyl, heterocyclenyl or heteroaryl ring, wherein said hetroacyclyl, heterocyclenyl or heteroaryl rings have 1-3 heteroatoms which are independently selected from the group consisting of O, N, —N(R$^9$)— and S, wherein said rings are optionally substituted by 1 to 5 independently selected R$^5$ moieties and/or 1 or 2 (=O) groups, $R^8$ is independently selected from the group consisting H, alkyl, halo, nitrile, and alkoxy;

$R^9$ is independently selected from the group consisting of H, —C(O)—R$^{10}$, —C(O)—OR$^{10}$, and —S(O)$_p$—OR$^{10}$ and alkyl, alkenyl, alkynyl, cycloalkyl, aryl, arylalkyl, heteroaryl, and heteroarylalkyl groups, each of which is optionally substituted with at least one of halo, —OH, —CN, —NO$_2$, —N(R$^{11}$)$_2$, and —S(O)$_p$R$^{11}$ substituents and/or 1 or 2 (=O) groups; and $R^{10}$ is independently selected from the group consisting of alkyl, alkenyl, alkynyl, cycloalkyl, aryl, arylalkyl, heteroaryl, and heteroarylalkyl groups, each of which is optionally substituted with at least one of halo, —OH, —CN, —NO$_2$, —N(R$^{11}$)$_2$, and —S(O)$_p$R$^{11}$ substituents and/or 1 or 2 (=O) groups;

$R^{11}$ is a moiety independently selected from the group consisting of H and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl, each of which is optionally substituted by at least one substituent independently selected from the group consisting of halo, —OH, —CN, —NO$_2$, —N(R$^{11}$)$_2$, and —S(O)$_p$R$^{11'}$ and/or 1 or 2 (=O) groups;

$R^{11'}$ is independently selected from the group consisting of H, alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl;

$R^{12}$ is independently selected from selected from the group consisting of H, halo, —OH, —CN, —NO$_2$, —N(R$^{11}$)$_2$, —C(O)—OR$^{14}$, —N(R$^{14}$)—C(O)—R$^{14}$, —N(R$^{14}$)—C(O)$_2$—R$^{14}$, —C(O)—N(R$^{11}$)$_2$, —N(R$^{14}$)—S(O)$_2$—R$^{11'}$, —S(O)$_2$—N(R$^{11}$)$_2$ and —S(O)$_p$R$^{11}$ and/or 1 or 2 (=O) groups, and alkyl, alkoxy, alkenyl, alkenyloxy, alkynyl, cycloalkyl, cycloalkenyl, cycloalkoxy, aryl, aryloxy, arylalkyl, heteroaryl, heteroaryloxy, heteroarylalkyl, heterocyclyl, heterocyclenyl, heterocyclenyloxy, heterocyclylalkyl, heterocyclenylalkyl, arylalkoxy, heteroarylalkoxy, heterocyclylalkoxy, and heterocyclenylalkoxy groups, each of which in turn is optionally substituted by at least once by a substituent selected from the group consisting of H, alkyl, haloalkyl, halo, —OH, optionally substituted alkoxy, optionally substituted aryloxy, optionally substituted cycloalkoxy, optionally substituted heteroaryloxy, optionally substituted heterocyclenyloxy, —CN, —NO$_2$, —N(R$^{11}$)$_2$, and —S(O)$_p$R$^{11'}$ and/or 1 or 2 (=O) groups, wherein said optionally substituted alkoxy, aryloxy, optionally substituted cycloalkoxy, optionally substituted heteroaryloxy, and heterocyclenyloxy when substituted are substituted one or more times by R$^{11}$;

$R^{14}$ is independently H, alkyl, or aryl;

m is 0 or 1;

n is independently 1, 2, or 3;

p is independently 0, 1, or 2;

q is independently an integer from 0-6;

w is 0, 1, 2, 3, 4, or 5; and z is 0, 1, 2, 3, 4, or 5, with the following provisos:

(a) if J is N, then J$^5$ is —C(R$^{6'}$)—;

(b) if J$^5$ is O, S or —N(R$^{6'}$)—, then J is —C— or —C(R$^6$)—;

(c) if m is 0, then z cannot be 0; and (d) if J is —C— or —C(R$^6$)— and J$^5$ is —C(R$^{6'}$)—, then R$^1$ cannot be cycloalkyl.

In one embodiment R$^1$ is optionally substituted (preferably 1 to 5 times) aryl (preferably optionally substituted phenyl) or optionally substituted (preferably 1 to 5 times) heteroaryl, wherein the optional substituents are, for example, any of the "ring system substituents" identified below. Preferred heteroaryl rings include pyridine, pyrimidine, furan, pyrrole, thiophene, pyridazine, pyrazine, indolizine, indole, isoindole, indoline, benzofuran, benzothiophene, indazole, benzimidazole, benzthiazole, quinoline, isoquinoline, cinnoline, phthalazine, quinazoline, quinoxaline, and naphthyridine. More preferred heteroaryl rings include pyridine, pyrimidine, furan, pyrrole, thiophene, pyridazine, pyrazine, indole, indoline, benzofuran, benzothiophene, benzimidazole, and benzthiazole. Most preferred heteroaryl rings include pyridine, pyrimidine, furan, pyrrole, and thiophene. Preferred optional substituents include alkyl, haloalkyl, nitro, cyano, halo, hydroxyl, alkoxy, amino, alkylamino, dialkylamino, haloalkoxy, aryl, and heteroaryl, wherein said aryl and heteroaryl are optionally substituted 1 to 5, preferably 1 to 3, times by alkyl, haloalkyl, nitro, cyano, halo, hydroxyl, alkoxy, amino, alkylamino, dialkylamino and haloalkoxy.

In another embodiment, R$^1$ is an optionally substituted pyridine ring.

In another embodiment, R$^1$ is an optionally substituted pyrimidine ring.

In another embodiment, R$^1$ is an optionally substituted furan ring.

In another embodiment, R$^1$ is an optionally substituted pyrrole ring.

In another embodiment A is an optionally substituted 5-membered heteroaryl, heterocyclenyl or heterocyclyl ring. Preferred optionally substituted heteroaryl, heterocyclenyl or heterocyclyl 5-membered rings include, for example, imidazole, thiazole, pyrrole, isoxazole, oxazole, isothiazole, pyrazole, imadazoline, imidazol-2-one, imidazol-2-thione, 2-aminoimidazoline, oxazoline, oxazol-2-one, oxazol-2-thione, 2-aminooxazoline, thiazoline, thiazol-2-one, thiazol-2-thione, 2-aminothiazoline, pyrroline, pyrazoline, pyrrolidine, imidazolidine, and pyrazolidine. A more preferred set of 5-membered rings includes: imidazole, imadazoline, imidazol-2-one, imidazol-2-thione, 2-aminoimidazoline, oxazoline, oxazol-2-one, oxazol-2-thione, and 2-aminooxazoline. A most preferred set of 5-membered rings includes imidazole. Optionally substituents include any of the "ring system substituents" identified below.

In another embodiment, if J$^1$-J$^3$ are —C(H)—, R$^1$ is an optionally substituted pyridine, pyrimidine, pyrimidine, furan or pyrrole ring, and A is unsubstituted imidazolyl.

In another embodiment, if J$^1$-J$^2$ are —C(H)—, J$^3$ is —N—, R$^1$ is an optionally substituted pyridine, pyrimidine, pyrimidine, furan or pyrrole ring, and A is unsubstituted imidazolyl.

In another embodiment, if J$^1$-J$^3$ are —C(H)—, J is —N—, J$^5$ is —C(H)—, n is 1, R$^3$ is H, R$^4$ is H, R$^{4'}$ is H, R$^1$ is an optionally substituted pyridine, pyrimidine, pyrimidine, furan or pyrrole ring, A is unsubstituted imidazolyl, z=0, and n=1 or 2.

In another embodiment, if J$^1$-J$^3$ are —C(H)—, J is —C—, J$^5$ is —N(R$^{6'}$)—, n is 1, R$^3$ is H, R$^4$ is H, R$^{4'}$ is H, R$^1$ is an optionally substituted pyridine, pyrimidine, pyrimidine, furan or pyrrole ring, A is unsubstituted imidazolyl, z=0, and n=1 or 2.

In another embodiment, if $J^1$-$J^3$ are —C(H)—, J is —C—, $J^5$ is —O—, n is 1, $R^3$ is H, $R^4$ is H, $R^{4'}$ is H, $R^1$ is an optionally substituted pyridine, pyrimidine, pyrimidine, furan or pyrrole ring, A is unsubstituted imidazolyl, z=0, and n=1 or 2.

In another embodiment, if $J^1$-$J^3$ are —C(H)—, J is —C—, $J^5$ is —S—, n is 1, $R^3$ is H, $R^4$ is H, $R^{4'}$ is H, $R^1$ is an optionally substituted pyridine, pyrimidine, pyrimidine, furan or pyrrole ring, A is unsubstituted imidazolyl, z=0, and n=1 or 2.

In another embodiment, if J is N, then $J^5$ is —C($R^{6'}$)—.

In another embodiment, if J is C, then $J^5$ is —N($R^{6'}$)—.

In another embodiment, if J is C, then $J^5$ is —O—.

In another embodiment, if J is C, then $J^5$ is —S—.

In another embodiment, if J is C, then $J^5$ is —C($R^{6'}$)—.

In another embodiment, if J is C($R^6$), then $J^5$ is —O—.

In another embodiment, if J is C($R^6$), then $J^5$ is —S—.

In another embodiment, if J is C($R^6$), then $J^5$ is —C($R^{6'}$)—.

In another embodiment, $J^1$-$J^3$ are each —C($R^2$)—.

In another embodiment, $J^1$ is —N—.

In another embodiment, $J^2$ is —N—.

In another embodiment, $J^3$ is —N—.

In another embodiment, $J^2$ and $J^3$ are both —N—.

In another embodiment, A is a 5-membered heterocyclic ring containing at least one ring nitrogen.

In another embodiment, $R^1$ is an optionally substituted pyridine, pyrimidine, furan or pyrrole ring, and A is an imadazoline.

In another embodiment, A is substituted with 1 or 2 (=O).

In another embodiment, $R^1$ is an optionally substituted pyridine, pyrimidine, furan or pyrrole ring, and A is a 2-aminoimidazoline.

In another embodiment, $R^1$ is an optionally substituted pyridine, pyrimidine, furan or pyrrole ring, and A is a 2-aminooxazoline.

In another embodiment, $R^1$ is an optionally substituted pyridine, pyrimidine, furan or pyrrole ring, and A is an imidazol-2-one.

In another embodiment, $R^1$ is an optionally substituted pyridine, pyrimidine, furan or pyrrole ring, and A is an imidazol-2-thione.

In another embodiment, $R^2$ is independently selected from the group consisting of H, —OH, halo, —CN, —$NO_2$—S$(O)_pR^7$, —$NR^7R^{7'}$, —$(CH_2)_qYR^{7'}$, —$(CH_2)_qN(R^7)YR^{7'}$, —$(CH_2)_qOYR^{7'}$, and —$(CH_2)_qON=CR^7R^{7'}$, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one $R^5$.

In another embodiment, $R^2$ is H.

In another embodiment, Y is selected from a bond, —C(=O)—, —C(=O)$NR^7$—, —C(=O)O—, —S$(O)_P$—, and —$SO_2NR^7$—.

In another embodiment, $R^3$ is independently selected from H, —CN and halo, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one $R^5$.

In another embodiment, $R^4$ is independently selected from H and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one $R^5$.

In another embodiment, $R^{4'}$ is independently selected from H and halo, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one $R^5$.

In another embodiment, in Formula Ia, atoms 1 and 2 form a double bond and $R^{4'}$ does not exist.

In another embodiment, $R^5$ is independently selected from H, halo, —OH, —CN, —$NO_2$, —$NR^7R^{7'}$, and —S$(O)_pR^7$, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups, each of which is optionally substituted with at least one of halo, —OH, —CN, —$NO_2$, —$NR^7R^{7'}$, and —S$(O)_pR^7$ substituents.

In another embodiment, $R^5$ is independently selected from H, halo, —OH, —CN, and alkyl.

In another embodiment, $R^6$ is independently selected from H and halo, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups, each of which is optionally substituted with at least one of halo, —OH, —CN, —$NO_2$, —$NR^7R^{7'}$, and —S$(O)_pR^7$ substituents, and —C(=O)$R^7$, —C(=O)$OR^7$, —C(=O)$NR^7R^{7'}$, —$SO_2R^7$ and —$SO_2$—$NR^7R^{7'}$.

In another embodiment, $R^{6'}$ is independently selected from H and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups, each of which is optionally substituted with at least one of halo, —OH, —CN, —$NO_2$, —$NR^7R^{7'}$, and —S$(O)_pR^7$ substituents, and —C(=O)$R^7$, —C(=O)$OR^7$, —C(=O)$NR^7R^{7'}$, —$SO_2R^7$ and —$SO_2$—$NR^7R^{7'}$.

In another embodiment, $R^{6'}$ is independently selected from H, optionally substituted alkyl, —C(=O)$R^7$, —C(=O)$OR^7$, —C(=O)$NR^7R^{7'}$, —$SO_2R^7$ and —$SO_2$—$NR^7R^{7'}$.

In another embodiment, $R^7$ is independently selected from H and alkyl, alkenyl, alkynyl, cycloalkyl, aryl, arylalkyl, heterocyclyl, heteroaryl, and heteroarylalkyl groups, each of which is optionally substituted with at least one of halo, alkoxy, —OH, —CN, —$NO_2$, —$N(R^{11})_2$, and —S$(O)_pR^{11}$ substituents.

In another embodiment, $R^{7'}$ is independently selected from H and alkyl, alkenyl, alkynyl, cycloalkyl, aryl, arylalkyl, heterocyclyl, heteroaryl, and heteroarylalkyl groups, each of which is optionally substituted with at least one of halo, alkoxy, —OH, —CN, —$NO_2$, —$N(R^{11})_2$, and —S$(O)_pR^{11}$ substituents.

In another embodiment, when a variable is —$NR^7R^{7'}$, —C(O)$NR^7R^{7'}$ or —$SO_2NR^7R^{7'}$, $R^7$ and $R^{7'}$ together with the N atom to which they are attached form a aziridine, azetidine, pyrrole, pyrrolidine, piperidine, piperazine or morpholine ring, each of which are optionally substituted by $R^5$.

In another embodiment, $R^8$ is independently selected from H, halo or alkyl.

In another embodiment, $R^{12}$ is independently alkyl, haloalkyl, —$NO_2$, —CN, halo, —OH, amino, alkylamino, dialkylamino or alkoxy.

In another embodiment $R^{13}$ is independently H or alkyl.

In another embodiment, m is 1 and z is 0-5, more preferably 0-3, most preferably 0 or 1.

In another embodiment, n is 1.

In another embodiment, n is 2.

In another embodiment, p is 0-2.

In another embodiment, z is an integer from 0-6, preferably 1-5, most preferably 1-3.

In another embodiment, m is 0 and z is an integer from 1-5, preferably 1 or 2, most preferably 1.

In another embodiment, A is imidazolyl.

In another embodiment, J is N.

In another embodiment, $J^5$ is $-N(R^{6'})-$.

In another embodiment, the present invention discloses compounds which are represented by structural formulae II-IX or a pharmaceutically acceptable salt, solvate or ester thereof, wherein the various definitions are those described above for Formula I:

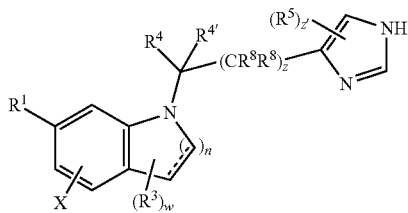

Formula II

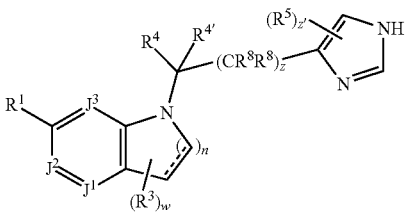

Formula III

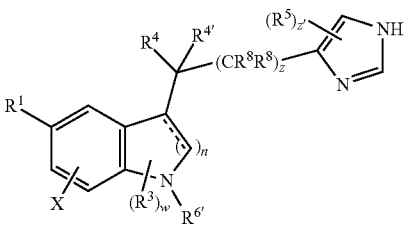

Formula IV

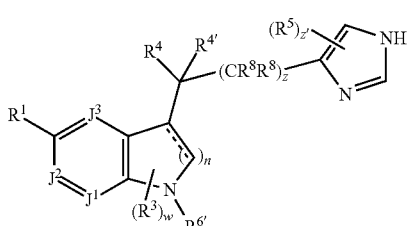

Formula V

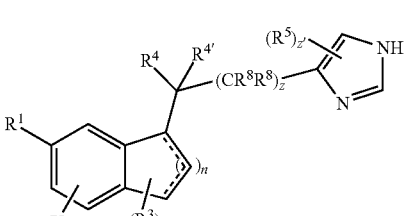

Formula VI

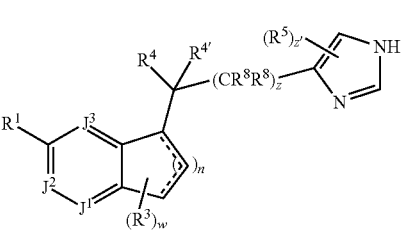

Formula VII

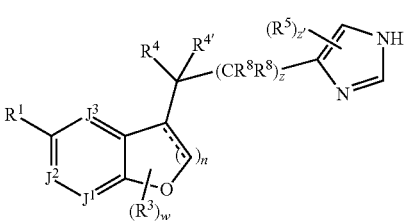

Formula VIII

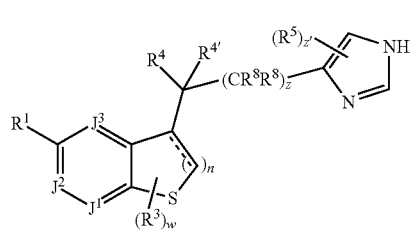

Formula IX and z' is an integer from 0-3.

Another embodiment of the compounds of Formulae II-IX are those wherein

X is halo or H, $J^1$, $J^2$, and $J^3$ are independently $-N-$ or $-C(R^2)-$;

$R^1$ is optionally substituted aryl, optionally substituted arylalkyl, optionally substituted arylalkoxy, optionally substituted pyridyl, optionally substituted pyrimidyl, optionally substituted furanyl, optionally substituted thiophenyl, optionally substituted quinolinyl, optionally substituted indolyl, optionally substituted pyrrolyl, and optionally substituted pyrrolidinyl, optionally substituted pyrazolyl, optionally substituted oxazolyl, optionally substituted isoxazolyl, optionally substituted pyridazinyl, optionally substituted pyrazinyl, optionally substituted tetrazolyl, optionally substituted imidazopyrimidinyl, optionally substituted thiazolyl, optionally substituted isothiazolyl, optionally substituted indazolyl, optionally substituted benzofuranyl, optionally substituted benzothiphenyl, optionally substituted isoquinolyl, optionally substituted benzimidazolyl, optionally substituted benzthiazolyl, optionally substituted quinoxalinyl, wherein said groups may be optionally substituted 1 to 3 times with substitutents selected from the group consisting of alkyl, haloalkyl, nitro, cyano, halo, hydroxyl, amino, alkylamino, dialkylamino, $-C(O)$-amino; $-C(O)$-alkylamino, $-C(O)$-dialkylamino, $-C(O)-OH$, $-C(O)-O$-alkyl, amino-C(O)-alkyl, amino-C(O)-O-alkyl, amino-S(O)$_2$-alkyl, alkoxy, haloalkoxy, aryl, and heteroaryl, wherein said aryl and heteroaryl are optionally substituted 1 to 3 times by alkyl, haloalkyl, nitro, cyano, halo, hydroxyl, amino, alkylamino, dialkylamino, alkoxy, and haloalkoxy;

z is an integer from 1 to 3;

z' is an integer from 0-2 and the remaining definitions are defined above in Formula I.

Another embodiment of the present invention is compounds of Formulae II or III wherein n is 1, z is 1, w is 0, z' is 0 or 1 and $R^4$ is H and the remaining definitions are defined above in Formula I.

Another embodiment of the present invention is the compounds of Formula I that have the structural formula IV

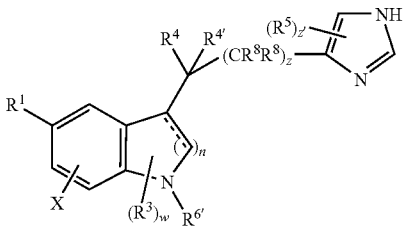

Formula IV or a pharmaceutically acceptable salt, ester, solvate, or prodrug of said compound,
wherein:
X is H or halo; —
═ is a single or double bond;
$R^1$ is selected from the group consisting of optionally substituted aryl, optionally substituted pyridyl, optionally substituted pyrimidyl, optionally substituted furanyl and optionally substituted pyrrolidinyl, wherein said groups may be optionally substituted 1 to 3 times with substitutents selected from the group consisting of alkyl, haloalkyl, nitro, cyano, halo, hydroxyl, amino, alkylamino, dialkylamino, alkoxy, haloalkoxy, aryl, and heteroaryl, wherein said aryl and heteroaryl are optionally substituted 1 to 3 times by alkyl, haloalkyl, nitro, cyano, halo, hydroxyl, amino, alkylamino, dialkylamino, alkoxy, and haloalkoxy;
$R^3$ is independently selected from the group consisting of H and halo, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one $R^5$;
$R^4$ is independently selected from the group consisting of H, —CN, and halo, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one $R^5$;
$R^5$ is independently selected from the group consisting of H, halo, —OH, —CN, —NO$_2$, —NR$^7$R$^{7'}$, and —S(O)$_p$R$^7$, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups, each of which is optionally substituted with at least one of halo, —OH, —CN, —NO$_2$, —NR$^7$R$^{7'}$, and —S(O)$_p$R$^7$ substituents and/or 1 or 2 (═O) groups;
$R^{6'}$ is independently selected from the group consisting of H and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups, each of which is optionally substituted with at least one of halo, —OH, —CN, —NO$_2$, —NR$^7$R$^{7'}$, and —S(O)$_p$R$^7$ and/or 1 or 2 (═O) groups substituents, and —C(═O)R$^7$, —C(═O)OR$^7$, —C(═O)NR$^7$R$^{7'}$, —SO$_2$R$^7$ and —SO$_2$NR$^7$R$^{7'}$;
$R^7$ is independently selected from the group consisting of H and alkyl, alkenyl, alkynyl, cycloalkyl, aryl, arylalkyl, heterocyclyl, heteroaryl, and heteroarylalkyl groups, each of which is optionally substituted with at least one of halo, alkoxy, —OH, —CN, —NO$_2$, —N(R$^{11}$)$_2$ and —S(O)$_p$R$^{11}$ substituents;
$R^{7'}$ is independently selected from the group consisting of H and alkyl, alkenyl, alkynyl, cycloalkyl, aryl, arylalkyl, heterocyclyl, heteroaryl, and heteroarylalkyl groups, each of which is optionally substituted with at least one of halo, alkoxy, —OH, —CN, —NO$_2$, —N(R$^{11}$)$_2$ and —S(O)$_p$R$^{11}$ substituents; or a) when a variable is —NR$^7$R$^{7'}$; —C(O)NR$^7$R$^{7'}$ or SO$_2$NR$^7$R$^{7'}$, R$^7$ and R$^{7'}$ together with the nitrogen atom to which they are attached form a 3- to 8-membered heterocyclyl, heterocyclenyl or heteroaryl ring having, in addition to the N atom, 1 or 2 additional hetero atoms selected from the group consisting of O, N, —N(R$^9$)— and S, wherein said rings are optionally substituted by 1 to 5 independently selected R$^5$ moieties,
$R^8$ is independently H or alkyl;
$R^9$ is independently selected from the group consisting of H, —C(O)—R$^{10}$, —C(O)—OR$^{10}$, and —S(O)$_p$—OR$^{10}$ and alkyl, alkenyl, alkynyl, cycloalkyl, aryl, arylalkyl, heteroaryl, and heteroarylalkyl groups, each of which is optionally substituted with at least one of halo, —OH, —CN, —NO$_2$, —N(R$^{11}$)$_2$, and —S(O)$_p$R$^{11}$ substituents; and
$R^{10}$ is selected from the group consisting of alkyl, alkenyl, alkynyl, cycloalkyl, aryl, arylalkyl, heteroaryl, and heteroarylalkyl groups, each of which is optionally substituted with at least one of halo, —OH, —CN, —NO$_2$, —N(R$^{11}$)$_2$, and —S(O)$_p$R$^{11}$ substituents;
$R^{11}$ is a moiety independently selected from the group consisting of H and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl;
z is an integer from 0-5;
n is independently 1, 2, or 3;
p is independently 0, 1 or 2;
q is independently an integer from 0-6;
w is 0, 1, 2, or 3; and
z' is 0, 1, 2, or 3.

Another embodiment of the present invention are the compounds of Formula I that have the structural formula V

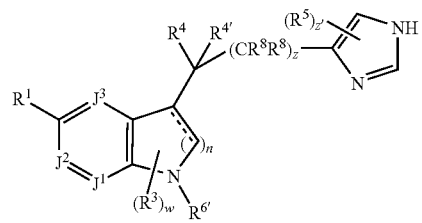

Formula V or a pharmaceutically acceptable salt, ester, solvate or prodrug of said compound,
wherein:
$J^1$, $J^2$, and $J^3$ are independently —N— or —C(R$^2$)—;
═ is a single or double bond;
$R^1$ is selected from the group consisting of optionally substituted aryl, optionally substituted pyridyl, optionally substituted pyrimidyl, optionally substituted furanyl and optionally substituted pyrrolidinyl, wherein said groups may be optionally substituted 1 to 3 times with substitutents selected from the group consisting of alkyl, haloalkyl, nitro, cyano, halo, hydroxyl, amino, alkylamino, dialkylamino, alkoxy, haloalkoxy, aryl, and heteroaryl, wherein said aryl and heteroaryl are optionally substituted 1 to 3 times by alkyl, haloalkyl, nitro, cyano, halo, hydroxyl, amino, alkylamino, dialkylamino, alkoxy, and haloalkoxy;
$R^2$ is independently selected from the group consisting of H, —OH, halo, —CN, —NO$_2$, —S(O)$_p$R$^7$, —NR$^7$R$^{7'}$, —(CH$_2$)$_q$YR$^{7'}$, —(CH$_2$)$_q$N(R$^7$)YR$^{7'}$, —(CH$_2$)$_q$OYR$^{7'}$, and —(CH$_2$)$_p$ON═CR$^7$R$^{7'}$, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one $R^5$;

Y is selected from a bond, —C(=O)—, —C(=O)$NR^7$—, —C(=O)O—, —S(O)$_p$—, and —SO$_2$$NR^7$—.

$R^3$ is independently selected from the group consisting of H, and halo, and (=O), and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one $R^5$ provided that when w is 3, no more than 2 of the $R^3$ groups may be (=O);

$R^4$ is independently selected from the group consisting of H, and halo, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one $R^5$;

$R^5$ is independently selected from the group consisting of H, halo, —OH, —CN, —NO$_2$, —$NR^7R^{7'}$, and —S(O)$_p$$R^7$, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups, each of which is optionally substituted with at least one of halo, —OH, —CN, —NO$_2$, —$NR^7R^{7'}$, and —S(O)$_p$$R^7$ substituents and/or 1 or 2 (=O) groups;

$R^{6'}$ is independently selected from the group consisting of H and halo, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups, each of which is optionally substituted with at least one of halo, —OH, —CN, —NO$_2$, —$NR^7R^{7'}$, and —S(O)$_p$$R^7$ substituents, and —C(=O)$R^7$, —C(=O)O$R^7$, —C(=O)$NR^7R^{7'}$, —SO$_2$$R^7$ and —SO$_2$$NR^7R^{7'}$;

$R^7$ is independently selected from the group consisting of H and alkyl, alkenyl, alkynyl, cycloalkyl, aryl, arylalkyl, heterocyclyl, heteroaryl, and heteroarylalkyl groups, each of which is optionally substituted with at least one of alkyl, haloalkyl, halo, alkoxy, —OH, —CN, —NO$_2$, —N($R^{11}$)$_2$ and —S(O)$_p$$R^{11}$ substituents;

$R^{7'}$ is independently selected from the group consisting of H and alkyl, alkenyl, alkynyl, cycloalkyl, aryl, arylalkyl, heterocyclyl, heteroaryl, and heteroarylalkyl groups, each of which is optionally substituted with at least one of alkyl, haloalkyl, halo, alkoxy, —OH, —CN, —NO$_2$, —N($R^{11}$)$_2$ and —S(O)$_p$$R^{11}$ substituents; or a) when a variable is —$NR^7R^{7'}$; —C(O)$NR^7R^{7'}$ or SO$_2$$NR^7R^{7'}$, $R^7$ and $R^{7'}$ together with the nitrogen atom to which they are attached form a 3- to 8-membered heterocyclyl, heterocyclenyl or heteroaryl ring having, in addition to the N atom, 1 or 2 additional hetero atoms selected from the group consisting of O, N, —N($R^9$)— and S, wherein said rings are optionally substituted by 1 to 5 independently selected $R^5$ moieties, $R^8$ is independently H or alkyl;

$R^9$ is independently selected from the group consisting of H, —C(O)—$R^{10}$, —C(O)—O$R^{10}$, and —S(O)$_p$—O$R^{10}$ and alkyl, alkenyl, alkynyl, cycloalkyl, aryl, arylalkyl, heteroaryl, and heteroarylalkyl groups, each of which is optionally substituted with at least one of halo, —OH, —CN, —NO$_2$, —N($R^{11}$)$_2$, and —S(O)$_p$$R^{11}$ substituents; and $R^{10}$ is selected from the group consisting of alkyl, alkenyl, alkynyl, cycloalkyl, aryl, arylalkyl, heteroaryl, and heteroarylalkyl groups, each of which is optionally substituted with at least one of halo, —OH, —CN, —NO$_2$, —N($R^{11}$)$_2$, and —S(O)$_p$$R^{11}$ substituents;

$R^{11}$ is a moiety independently selected from the group consisting of H and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl;

z is an integer from 0-5;

n is independently 1, 2, or 3;

p is independently 0, 1, or 2;

q is independently an integer from 0-6;

w is 0, 1, 2, or 3; and z' is 0, 1, 2, or 3.

Another embodiment of the present invention are the compounds of Formula I that have the structural formula VI

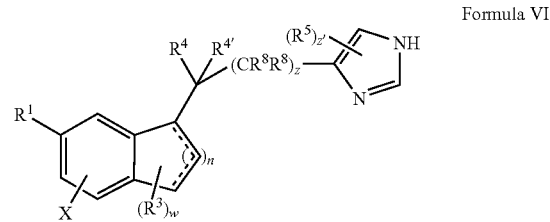

Formula VI wherein $R^1$ is selected from the group consisting of optionally substituted aryl, optionally substituted pyridyl, optionally substituted pyrimidyl, optionally substituted furanyl, optionally substituted thiophenyl and optionally substituted pyrrolyl and optionally substituted pyrrolidinyl, wherein said groups may be optionally substituted 1 to 3 times with substitutents selected from the group consisting of alkyl, haloalkyl, nitro, cyano, halo, hydroxyl, amino, alkylamino, dialkylamino, alkoxy, haloalkoxy, aryl, and heteroaryl, wherein said aryl and heteroaryl are optionally substituted 1 to 3 times by alkyl, haloalkyl, nitro, cyano, halo, hydroxyl, amino, alkylamino, dialkylamino, alkoxy, and haloalkoxy;

X is H or halo;

z is an integer from 0-5;

w is an integer from 0-3;

z' is an integer from 0-3; and n is independently 1, 2 or 3, or a pharmaceutically acceptable salt, ester, solvate or prodrug thereof.

Another embodiment of the present invention are the compounds of Formula I that have the structural Formula VII

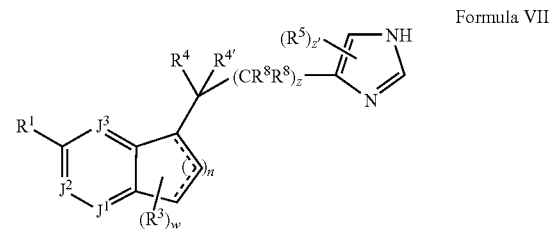

Formula VII wherein:

$J^1$, $J^2$ and $J^3$ are independently —N— or —(CR$^2$)—;

$R^1$ is selected from the group consisting of optionally substituted aryl, optionally substituted pyridyl, optionally substituted pyrimidyl, optionally substituted furanyl, optionally substituted thiophenyl and optionally substituted pyrrolyl and optionally substituted pyrrolidinyl, wherein said groups may be optionally substituted 1 to 3 times with substitutents selected from the group consisting of alkyl, haloalkyl, nitro, cyano, halo, hydroxyl, amino, alkylamino, dialkylamino, alkoxy, haloalkoxy, aryl, and heteroaryl, wherein said aryl and heteroaryl are optionally substituted 1 to 3 times by alkyl, haloalkyl, nitro, cyano, halo, hydroxyl, amino, alkylamino, dialkylamino, alkoxy, and haloalkoxy;

X is H or halo;
z is an integer from 0-5;
w is 0, 1, 2, or 3; and
z' is 0, 1, 2, or 3; and
n is independently 1, 2, or 3, or a pharmaceutically acceptable salt, ester, solvate or prodrug thereof.

Another embodiment of the compounds of Formula I is compounds represented by the structural Formula X

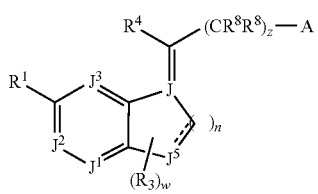

X or a pharmaceutically acceptable salt, ester, solvate or prodrug thereof,
wherein:

A is a 5-membered heteroaryl, heterocyclyl or heterocyclenyl ring containing 1-3 heteroatoms, and is optionally substituted with at least one $R^5$ and/or 1 or 2 (=O) (carbonyl) groups;

$J^1$, $J^2$, and $J^3$ are independently —N—, —N(O)— or —C($R^2$)—;

J is C;

$J^5$ is —C($R^{6'}$)—, —N($R^{6'}$)—, —O— or —S—, with the proviso that a double bond is not present between $J^5$ and an adjacent ring atom when $J^5$; is —O— or —S—;

═ is a single or double bond provided that there cannot be two continuous double bonds $R^1$ is a ring selected from the group consisting of cycloalkyl, cycloalkenyl, aryl, heterocyclyl, heterocyclenyl, and heteroaryl, each of which is optionally substituted with at least one $R^{12}$;

$R^2$ is independently selected from the group consisting of H, —OH, halo, —CN, —NO$_2$, —S(O)$_p$R$^7$, —NR$^7$R$^{7'}$, —(CH$_2$)$_q$YR$^{7'}$, —(CH$_2$)$_q$—N(R$^7$)YR$^{7'}$, —(CH$_2$)$_q$OYR$^{7'}$, and —(CH$_2$)$_q$ON═CR$^7$R$^{7'}$, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one $R^5$;

Y is selected from the group consisting of a bond, —C(═O)—, —C(═O)NR$^7$—, —C(═O)O—, —C(═NR$^7$)—, —C(═NOR$^7$)—, —C(═NR$^7$)NR$^7$—, —C(═NR$^7$)NR$^7$O—, —S(O)$_p$—, —SO$_2$NR$^7$—, and —C(═S)NR$^7$—;

$R^3$ is independently selected from the group consisting of H, halo, and (═O), and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one $R^5$, provided that when w is 3, no more than 2 of the $R^3$ groups may be (═O);

$R^4$ is selected from the group consisting of H, —CN, and halo, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one $R^5$;

$R^5$ is independently selected from the group consisting of H, halo, —OH, —CN, —NO$_2$, —NR$^7$R$^{7'}$, and —S(O)$_p$R$^7$, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups, each of which is optionally substituted with at least one of halo, —OH, —CN, —NO$_2$, —NR$^7$R$^{7'}$, and —S(O)$_p$R$^7$ substituents and/or 1 or 2 (═O) groups, $R^{6'}$ is independently selected from the group consisting of H and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups, each of which is optionally substituted with at least one of halo, —OH, —CN, —NO$_2$, —NR$^7$R$^{7'}$, and —S(O)$_p$R$^7$ and/or 1 or 2 (═O) groups substituents, and —C(═O)R$^7$, —C(═O)OR$^7$, —C(═O)NR$^7$R$^{7'}$, —SO$_2$R$^7$ and —SO$_2$NR$^7$R$^{7'}$;

$R^7$ is independently selected from the group consisting of H and alkyl, alkenyl, alkynyl, cycloalkyl, cycloalkylalkyl, cyclocenyl, cyclocyclenylalkyl, aryl, arylalkyl, heterocyclyl, heterocyclylalkyl, hetrocyclenyl, hetrocyclenylalkyl, heteroaryl, and heteroarylalkyl groups, each of which is optionally substituted one or more times by $R^{12}$;

$R^{7'}$ is independently selected from the group consisting of H and alkyl, alkenyl, alkynyl, cycloalkyl, cycloalkylalkyl, cyclocenyl, cyclocyclenylalkyl, aryl, arylalkyl, heterocyclyl, heterocyclylalkyl, hetrocyclenyl, hetrocyclenylalkyl, heteroaryl, and heteroarylalkyl groups, each of which is optionally substituted one or more times by $R^{12}$; or a) when a variable is —NR$^7$R$^{7'}$, —C(O)NR$^7$R$^{7'}$ or SO$_2$NR$^7$R$^{7'}$, $R^7$ and $R^{7'}$ together with the nitrogen atom to which they are attached independently form a 3- to 8-membered heterocyclyl, heterocyclenyl or heteroaryl ring having, in addition to the N atom, 1 or 2 additional hetero atoms independently selected from the group consisting of O, N, —N(R$^9$)— and S, wherein said rings are optionally substituted by 1 to 5 independently selected $R^5$ moieties and/or 1 or 2 (═O) groups, or b) when a variable is —(CH$_2$)$_q$ON═CR$^7$R$^{7'}$, $R^7$ and $R^{7'}$ together with the carbon atom to which they are attached independently form a 3- to 8-membered cycloalkyl, cycloalkenyl, aryl, heterocyclyl, heterocyclenyl or heteroaryl ring, wherein said hetroacyclyl, heterocyclenyl or heteroaryl rings have 1-3 heteroatoms which are independently selected from the group consisting of O, N, —N(R$^9$)— and S, wherein said rings are optionally substituted by 1 to 5 independently selected $R^5$ moieties and/or 1 or 2 (═O) groups, $R^8$ is independently selected from the group consisting H, alkyl, halo, nitrile, and alkoxy;

$R^9$ is independently selected from the group consisting of H, —C(O)—R$^{10}$, —C(O)—OR$^{10}$, and —S(O)$_p$—OR$^{10}$ and alkyl, alkenyl, alkynyl, cycloalkyl, aryl, arylalkyl, heteroaryl, and heteroarylalkyl groups, each of which is optionally substituted with at least one of halo, —OH, —CN, —NO$_2$, —N(R$^{11}$)$_2$, and —S(O)$_p$R$^{11}$ substituents and/or 1 or 2 (═O) groups; and $R^{10}$ is independently selected from the group consisting of alkyl, alkenyl, alkynyl, cycloalkyl, aryl, arylalkyl, heteroaryl, and heteroarylalkyl groups, each of which is optionally substituted with at least one of halo, —OH, —CN, —NO$_2$, —N(R$^{11}$)$_2$, and —S(O)$_p$R$^{11}$ substituents and/or 1 or 2 (═O) groups;

$R^{11}$ is a moiety independently selected from the group consisting of H and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl, each of which is optionally substituted by at least one substituent independently selected from the group consisting of halo, —OH, —CN, —NO₂, —N(R¹¹')₂, and —S(O)$_p$R¹¹' and/or 1 or 2 (=O) groups;

R¹¹' is independently selected from the group consisting of H, alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl;

R¹² is independently selected from selected from the group consisting of H, halo, —OH, —CN, —NO₂, —N(R¹¹)₂, —C(O)—OR¹⁴, —N(R¹⁴)—C(O)—R¹⁴, —N(R¹⁴)—C(O)₂—R¹⁴, —C(O)—N(R¹¹)₂, —N(R¹⁴)—S(O)₂—R¹¹', —S(O)₂—N(R¹¹)₂ and —S(O)$_p$R¹¹ and/or 1 or 2 (=O) groups, and alkyl, alkoxy, alkenyl, alkenyloxy, alkynyl, cycloalkyl, cycloalkenyl, cycloalkoxy, aryl, aryloxy, arylalkyl, heteroaryl, heteroaryloxy, heteroarylalkyl, heterocyclyl, heterocyclenyl, heterocyclenyloxy, heterocyclylalkyl, heterocyclenylalkyl, arylalkoxy, heteroarylalkoxy, heterocyclylalkoxy, and heterocyclenylalkoxy groups, each of which in turn is optionally substituted by at least once by a substituent selected from the group consisting of H, alkyl, haloalkyl, halo, —OH, optionally substituted alkoxy, optionally substituted aryloxy, optionally substituted cycloalkoxy, optionally substituted heteroaryloxy, optionally substituted heterocyclenyloxy, —CN, —NO₂, —N(R¹¹)₂, and —S(O)$_p$R¹¹ and/or 1 or 2 (=O) groups, wherein said optionally substituted alkoxy, aryloxy, optionally substituted cycloalkoxy, optionally substituted heteroaryloxy, and heterocyclenyloxy when substituted are substituted one or more times by R¹¹;

R¹⁴ is independently H, alkyl, or aryl;

m is 0 or 1;

n is independently 1, 2, or 3;

p is independently 0, 1, or 2;

q is independently an integer from 0-6;

w is 0, 1, 2, 3, 4 or 5; and z is 0, 1, 2, 3, 4, or 5 with the following provisos:

(a) if J is N, then J⁵ is —C(R⁶')—;
(b) if J⁵ is O, S or —N(R⁶')—, then J is —C— or —C(R⁶)—;
(c) if m is 0, then z cannot be 0; and
(d) if J is —C— or —C(R⁶)— and J⁵ is —C(R⁶')—, then R¹ cannot be cycloalkyl.

An embodiment of the compounds of Formula X is compounds represented by structural Formula Xa:

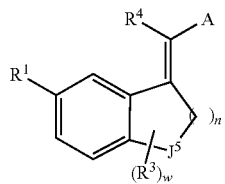

Xa or their pharmaceutically acceptable esters or salts, wherein the variables are those defined above for Formula X.

A further embodiment of the compounds of Formula Xa or their pharmaceutically acceptable esters or salts wherein:

A is imidazole;

R¹ is optionally substituted aryl, optionally substituted arylalkyl, optionally substituted arylalkoxy, optionally substituted pyridyl, optionally substituted pyrimidyl, optionally substituted furanyl, optionally substituted thiophenyl, optionally substituted quinolinyl, optionally substituted indolyl, optionally substituted pyrrolyl, and optionally substituted pyrrolidinyl, wherein said groups may be optionally substituted 1 to 3 times with substitutents selected from the group consisting of alkyl, haloalkyl, nitro, cyano, halo, hydroxyl, amino, alkylamino, dialkylamino, —C(O)-amino; —C(O)-alkylamino, —C(O)-dialkylamino, —C(O)—OH, —C(O)—O-alkyl, alkoxy, haloalkoxy, aryl, and heteroaryl, wherein said aryl and heteroaryl are optionally substituted 1 to 3 times by alkyl, haloalkyl, nitro, cyano, halo, hydroxyl, amino, alkylamino, dialkylamino, alkoxy, and haloalkoxy n is 1 or 2;

J⁵ is —CH₂—, —O—, or —S—, w is 0 or 1; and

R³ is independently H or alkyl.

A further embodiment of the compounds of Formula X is compounds represented by structural Formula Xb

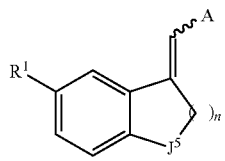

Xb or a pharmaceutically acceptable ester of salt thereof wherein

R¹ is optionally substituted aryl, optionally substituted arylalkyl, optionally substituted arylalkoxy, optionally substituted pyridyl, optionally substituted pyrimidyl, optionally substituted furanyl, optionally substituted thiophenyl, optionally substituted quinolinyl, optionally substituted indolyl, optionally substituted pyrrolyl, and optionally substituted pyrrolidinyl, wherein said groups may be optionally substituted 1 to 3 times with substitutents selected from the group consisting of alkyl, haloalkyl, nitro, cyano, halo, hydroxyl, amino, alkylamino, dialkylamino, —C(O)-amino; —C(O)-alkylamino, —C(O)-dialkylamino, —C(O)—OH, —C(O)—O-alkyl, alkoxy, haloalkoxy, aryl, and heteroaryl, wherein said aryl and heteroaryl are optionally substituted 1 to 3 times by alkyl, haloalkyl, nitro, cyano, halo, hydroxyl, amino, alkylamino, dialkylamino, alkoxy, and haloalkoxy;

n is 1 or 2;

∿∿∿ indicates that A may be cis or trans with the bicyclic ring; and

J⁵ is —CH₂—, —O—, or —S—.

A further embodiment of the compounds of Formula X is compounds represented by structural Formula XI

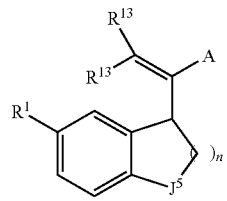

XI or a pharmaceutically acceptable ester or salt thereof wherein

A is imidazole;

R¹ is selected from the group consisting of optionally substituted aryl, optionally substituted arylalkyl, optionally substituted arylalkoxy, optionally substituted pyridyl, optionally substituted pyrimidyl, optionally substituted furanyl, optionally substituted thiophenyl, optionally substituted quinolinyl, optionally substituted indolyl, optionally substituted pyrrolyl, and optionally substituted pyrrolidinyl, wherein said groups may be optionally substituted 1 to 3 times with substitutents selected from the group consisting of alkyl, haloalkyl, nitro, cyano, halo, hydroxyl, amino, alkylamino, dialkylamino, —C(O)-amino; —C(O)-alkylamino, —C(O)-dialkylamino, —C(O)—OH, —C(O)—Oalkyl, alkoxy, haloalkoxy, aryl, and heteroaryl, wherein said aryl and heteroaryl are optionally substituted 1 to 3 times by alkyl, haloalkyl, nitro, cyano, halo, hydroxyl, amino, alkylamino, dialkylamino, alkoxy, and haloalkoxy;

n is 1 or 2; and $J^5$ is —(CH$_2$)—, —O—, or —S—.

A group of compounds is shown below:

An especially preferred group of compounds of the invention is shown below: shown below:

35
-continued
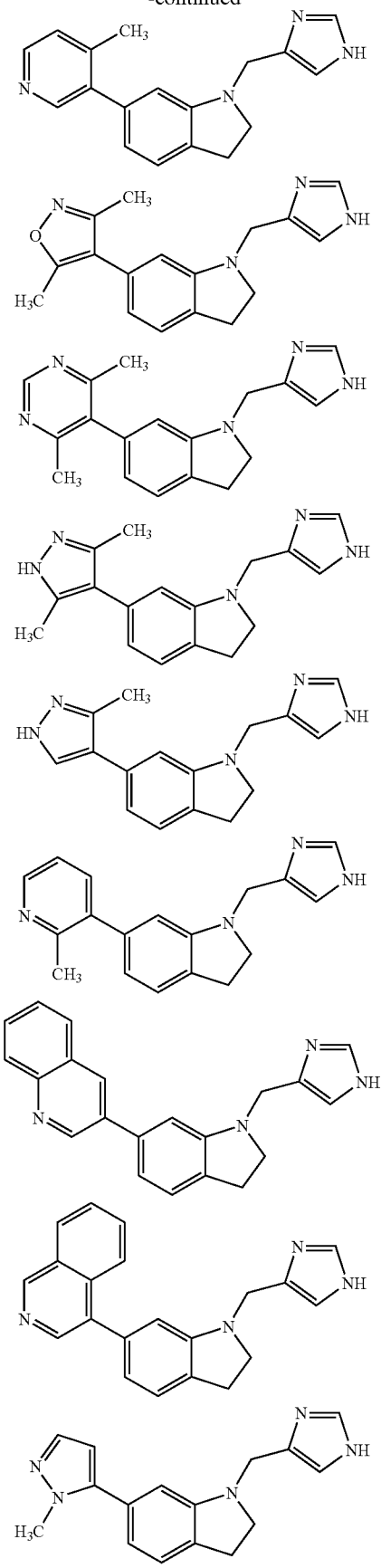
36
-continued
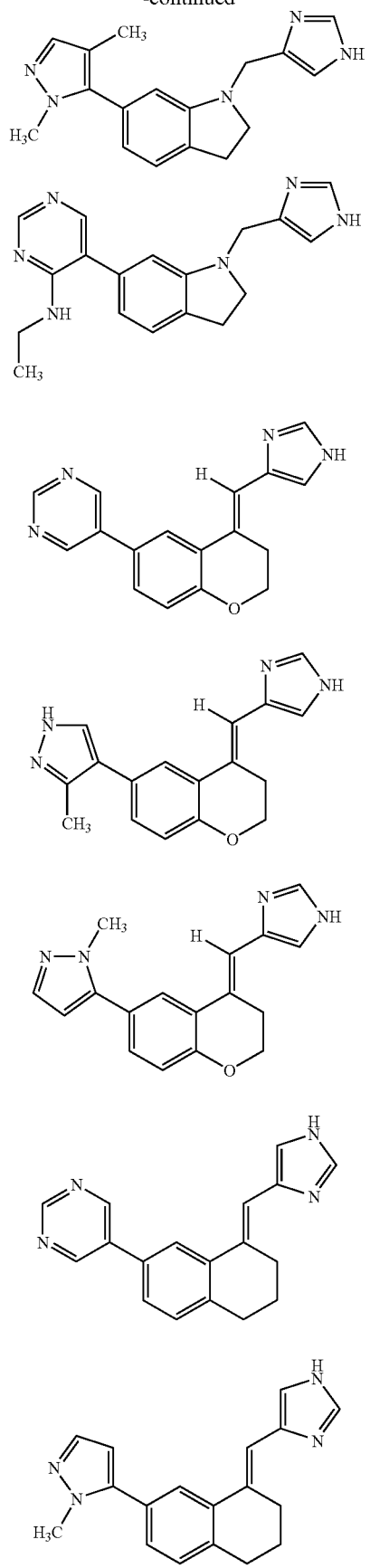

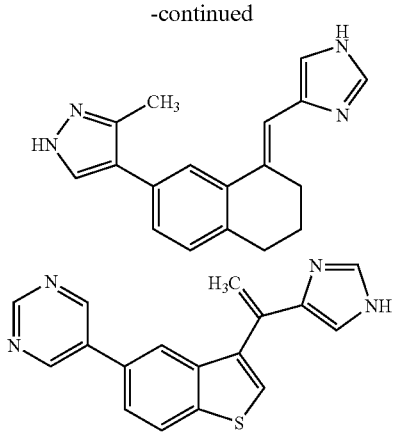

A further embodiment of the present invention is compounds of Formula I in isolated and purified form.

Another embodiment of the present invention is a method for selectively stimulating α2C adrenergic receptors in a cell in need thereof, comprising contacting said cell with a therapeutically effective amount of at least one compound of Formula I.

As used above, and throughout this disclosure, the following terms, unless otherwise indicated, shall be understood to have the following meanings:

"Patient" includes both human and animals.

"Mammal" means humans and other mammalian animals.

"Congestion" refers to all type of congestion including, but not limited to, congestion associated with perennial allergic rhinitis, seasonal allergic rhinitis, non-allergic rhinitis, vasomotor rhinitis, rhinitis medicamentosa, sinusitis, acute rhinosinusitis, or chronic rhinosinusitis or when the congestion is caused by polyps or is associated with the common cold.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl and t-butyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. The term "substituted alkynyl" means that the alkynyl group may be substituted by one or more substituents which may be the same or different, each substituent being independently selected from the group consisting of alkyl, aryl and cycloalkyl.

"Aryl" means an aromatic monocyclic or multicyclic ring system, in which at least one of the multicyclic rings is an aryl ring, comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl. Non-limiting examples of aryl multicyclic ring systems include:

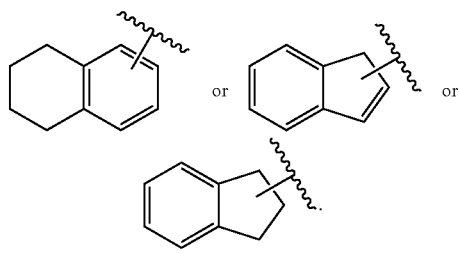

"Heteroaryl" means an aromatic monocyclic or multicyclic ring system, in which at least one of the multicyclic rings is aromatic, comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like.

Non-limiting examples of heteroaryl multicyclic ring systems include:

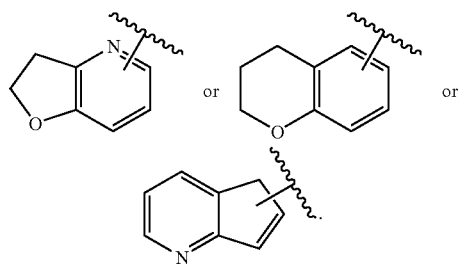

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl-group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Halogen" and "Halo" mean fluorine, chlorine, bromine, or iodine. Preferred are fluorine, chlorine or bromine, and more preferred are fluorine and chlorine.

"Ring system substituent" means a substituent attached to an aromatic or non-aromatic ring system which, for example, replaces an available hydrogen on the ring system. Ring system substituents may be the same or different, each being independently selected from the group consisting of aryl, heteroaryl, aralkyl, alkylaryl, heteroaralkyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, $Y_1Y_2NC(O)$— and $Y_1Y_2NSO_2$—, wherein $Y_1$ and $Y_2$ may be the same or different and are independently selected from the group consisting of hydrogen, alkyl, aryl, and aralkyl.

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protected moieties are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, imidazolidinyl, pyrazolidinyl and the like.

Compounds of Formula I and salts, esters, solvates and prodrugs thereof, may exist in their tautomeric form (for example, as an amide or imino ether). All such tautomeric forms are contemplated herein as part of the present invention. Non-limiting examples of tautomeric forms that are part of this invention are as follows:

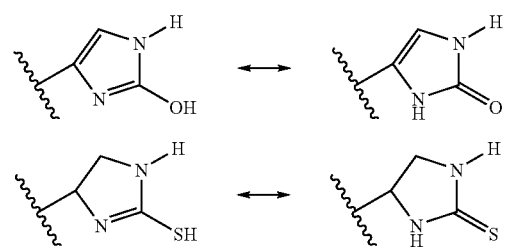

It should be noted that in saturated heterocyclyl containing systems of this invention, there are no hydroxyl, amino, or thiol groups on carbon atoms adjacent to a N, O or S atom. Thus, for example, in the ring:

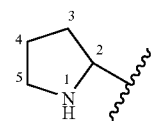

there is no —OH attached directly to carbons marked 2 and 5. It should also be noted that this definition does not preclude (=O), (=S), or (=N) substitutions, or their tautomeric forms, on C atoms adjacent to a N, O or S. Thus, for example, in the above ring, (=O) substitution on carbon 5, or its imino ether tautomer is allowed.

Non-limiting examples which illustrate the present invention are as follows:

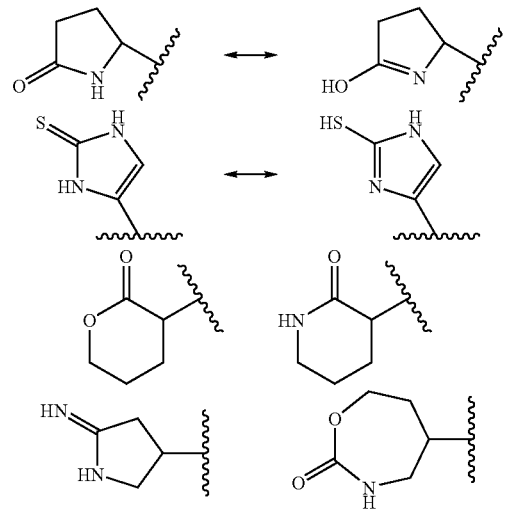

The following non-limiting examples serve to illustrate radicals not contemplated by the present invention:

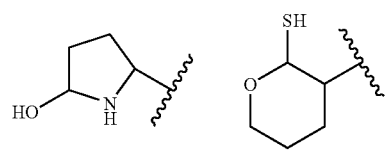

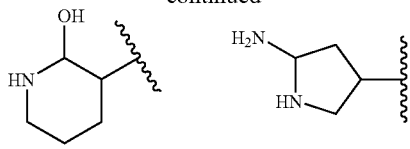

"Alkynylalkyl" means an alkynyl-alkyl-group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Heterocyclylalkyl" or "heteroarylalkyl" means a heterocyclyl-alkyl group in which the heterocyclyl and the alkyl are as previously described. Preferred heterocyclylalkyls contain a lower alkyl group. Non-limiting examples of suitable heterocyclylalkyl groups include piperidylmethyl, piperidylethyl, pyrrolidylmethyl, morpholinylpropyl, piperazinylethyl, azindylmethyl, azetidylethyl, oxiranylpropyl and the like. The bond to the parent moiety is through the alkyl group.

"Heterocyclenyl" (or "heterocycloalkeneyl") means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable monocyclic azaheterocyclenyl groups include 1,2,3,4-tetrahydropyridyl, 1,2-dihydropyridyl, 1,4-dihydropyridyl, 1,2,3,6-tetrahydropyridyl, 1,4,5,6-tetrahydropyrimidyl, 2-pyrrolinyl, 3-pyrrolinyl, 2-imidazolinyl, 2-pyrazolinyl, 2-oxazolinyl, 2-thiazolinyl, and the like. Non-limiting examples of suitable oxaheterocyclenyl groups include 3,4-dihydro-2H-pyran, dihydrofuranyl, fluorodihydrofuranyl, and the like. Non-limiting example of a suitable multicyclic oxaheterocyclenyl group is 7-oxabicyclo[2.2.1]heptenyl. Non-limiting examples of suitable monocyclic thiaheterocyclenyl rings include dihydrothiophenyl, dihydrothiopyranyl, and the like.

"Heterocyclenylalkyl" means a heterocyclenyl-alkyl group in which the heterocyclenyl and the alkyl are as previously described.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an organic acid group in which the —OH of the carboxyl group is replaced by some other substituent. Suitable non-limiting examples include H—C(O)—, alkyl-C (O)—, cycloalkyl-C(O)—, heterocyclyl-C(O)—, and heteroaryl-C(O)— groups in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" or "arylalkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Heteroarylalkoxy" means a heteroarylalkyl-O-group in which the heteroarylalkyl group is as previously described.

"Heterocyclylalkoxy" means a heterocyclylalkyl-O group in which the heterocyclylalkyl group is as previously described.

"Heterocyclenylalkoxy" means a heterocyclenylalkyl-O group in which the heterocyclenylalkyl group is as previously described.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S($O_2$)— group. Preferred groups are those in which the alkyl group is lower alkyl. The bond to the parent moiety is through the sulfonyl.

"Arylsulfonyl" means an aryl-S($O_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

It is noted that carbons of formula I can be replaced with 1-3 silicon atoms, provided all valency requirements are satisfied.

The term "optionally substituted" means optional substitution with the specified groups, radicals or moieties.

The straight — line as a bond generally indicates a mixture of, or either of, the possible isomers, non-limiting example(s) include, containing (R)- and (S)-stereochemistry. For example,

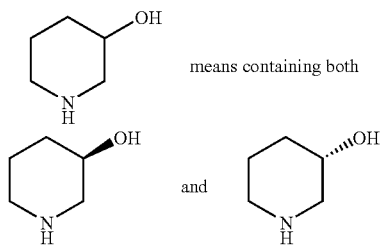

A dashed line (-----) represents an optional bond.
Lines drawn into the ring systems, such as, for example:

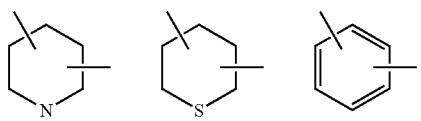

indicate that the indicated line (bond) may be attached to any of the substitutable ring atoms, non-limiting examples include carbon, nitrogen and sulfur ring atoms.

As well known in the art, a bond drawn from a particular atom wherein no moiety is depicted at the terminal end of the bond indicates a methyl group bound through that bond to the atom, unless stated otherwise. For example:

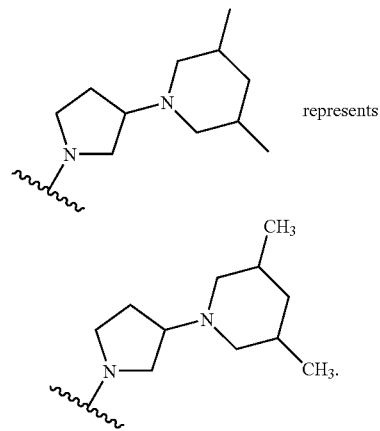

It should also be noted that any heteroatom with unsatisfied valences in the text, schemes, examples and Tables herein is assumed to have the hydrogen atom to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or formula, its definition on each occurrence is independent of its definition at every other occurrence.

Unless defined otherwise, all definitions for the variables follow the convention that the group to the right forms the point of attachment to the molecule; i.e., if a definition is arylalkyl, this means that the alkyl portion of the definition is attached to the molecule.

Further, all divalent variable are attached from left to right. For example when $R^2$ is —$(CH_2)_q$—$N(R^7)YR^{7'}$, and Y is —$C(=O)NR^7$—, then $R^1$ forms the group —$(CH_2)_q N(R^7)$—$C(=O)N(R^7)$—$R^{7'}$.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of formula I or a salt and/or solvate thereof. A discussion of prodrugs is provided in T. Higuchi and V. Stella, *Pro-drugs as Novel Delivery Systems* (1987) Volume 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

For example, if a compound of Formula I or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as 8-dimethylaminoethyl), carbamoyl-$(C_1-C_2)$alkyl, N,N-di$(C_1-C_2)$alkylcarbamoyl-$(C_1-C_2)$alkyl and piperidino-, pyrrolidino- or morpholino$(C_2-C_3)$alkyl, and the like.

Similarly, if a compound of Formula I contains an alcohol functional group, a prodrug can be formed by the replacement of the hydrogen atom of the alcohol group with a group such as, for example, $(C_1-C_6)$alkanoyloxymethyl, 1-(($C_1-C_6$)alkanoyloxy)ethyl, 1-methyl-1-(($C_1-C_6$)alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino$(C_1-C_4)$alkanyl, arylacyl and α-aminoacyl, or α-aminoacyl-α-aminoacyl, where each α-aminoacyl group is independently selected from the naturally occurring L-amino acids, —$P(O)(OH)_2$, —$P(O)(O(C_1-C_6)alkyl)_2$ or glycosyl (the radical resulting from the removal of a hydroxyl group of the hemiacetal form of a carbohydrate), and the like.

If a compound of Formula I incorporates —NH— functional group, such as in a primary or secondary amine or in a nitrogen-containing heterocycle, such as imidazole or piperazine ring, a prodrug can be formed by the replacement of a hydrogen atom in the amine group with a group such as, for example, R-carbonyl, RO-carbonyl, NRR'-carbonyl where R and R' are each independently $(C_1-C_{10})$alkyl, $(C_3-C_7)$cycloalkyl, benzyl, or R-carbonyl is a natural α-aminoacyl or natural α-aminoacyl, —C(OH)C(O)OY$^1$ wherein Y$^1$ is H, $(C_1-C_6)$alkyl or benzyl, —C(OY$^2$)Y$^3$ wherein Y$^2$ is $(C_1-C_4)$ alkyl and Y$^3$ is $(C_1-C_6)$alkyl, carboxy$(C_1-C_6)$alkyl, amino $(C_1-C_4)$alkyl or mono-N— or di-N,N—$(C_1-C_6)$alkylaminoalkyl, —C(Y$^4$)Y$^5$ wherein Y$^4$ is H or methyl and Y$^5$ is mono-N— or di-N,N—$(C_1-C_6)$alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of illustrative solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS Pharm Sci Tech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

Metabolic conjugates, such as glucuronides and sulfates which can undergo reversible conversion to the compounds of Formula I are contemplated in the present invention.

"Effective amount" or "therapeutically effective amount" is meant to describe an amount of compound or a composition of the present invention effective in producing the desired therapeutic, ameliorative, inhibitory or preventative effect.

The terms "purified", "in purified form" or "in isolated and purified form," as used herein, for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like), in sufficient purity to be characterizable by standard analytical techniques described herein or well known to the skilled artisan.

"Capsule" is meant to describe a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

"Tablet" is meant to describe a compressed or molded solid dosage form containing the active ingredients with suitable diluents. The tablet can be prepared by compression of mixtures or granulations obtained by wet granulation, dry granulation or by compaction.

"Oral gels" is meant to describe to the active ingredients dispersed or solubilized in a hydrophillic semi-solid matrix.

"Powders for constitution" refers to powder blends containing the active ingredients and suitable diluents which can be suspended in water or juices.

"Diluent" refers to substances that usually make up the major portion of the composition or dosage form. Suitable diluents include sugars such as lactose, sucrose, mannitol and sorbitol; starches derived from wheat, corn, rice and potato; and celluloses such as microcrystalline cellulose. The amount of diluent in the composition can range from about 10 to about 90% by weight of the total composition, preferably from about 25 to about 75%, more preferably from about 30 to about 60% by weight, even more preferably from about 12 to about 60%.

"Disintegrants" refers to materials added to the composition to help it break apart (disintegrate) and release the medicaments. Suitable disintegrants include starches; "cold water soluble" modified starches such as sodium carboxymethyl starch; natural and synthetic gums such as locust bean, karaya, guar, tragacanth and agar; cellulose derivatives such as methylcellulose and sodium carboxymethylcellulose; microcrystalline celluloses and cross-linked microcrystalline celluloses such as sodium croscarmellose; alginates such as alginic acid and sodium alginate; clays such as bentonites; and effervescent mixtures. The amount of disintegrant in the composition can range from about 2 to about 15% by weight of the composition, more preferably from about 4 to about 10% by weight.

"Binders" refers to substances that bind or "glue" powders together and make them cohesive by forming granules, thus serving as the "adhesive" in the formulation. Binders add cohesive strength already available in the diluent or bulking agent. Suitable binders include sugars such as sucrose; starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropylmethylcellulose; polyvinylpyrrolidone; and inorganics such as magnesium aluminum silicate. The amount of binder in the composition can range from about 2 to about 20% by weight of the composition, more preferably from about 3 to about 10% by weight, even more preferably from about 3 to about 6% by weight.

"Lubricant" is meant to describe a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and d'l-leucine. Lubricants are usually added at the very last step before compression, since they must be present on the surfaces of the granules and in between them and the parts of the tablet press. The amount of lubricant in the composition can range from about 0.2 to about 5% by weight of the composition, preferably from about 0.5 to about 2%, more preferably from about 0.3 to about 1.5% by weight.

"Glidents" means materials that prevent caking and improve the flow characteristics of granulations, so that flow is smooth and uniform. Suitable glidents include silicon dioxide and talc. The amount of glident in the composition can range from about 0.1% to about 5% by weight of the total composition, preferably from about 0.5 to about 2% by weight.

"Coloring agents" refers to excipients that provide coloration to the composition or the dosage form. Such excipients can include food grade dyes and food grade dyes adsorbed onto a suitable adsorbent such as clay or aluminum oxide. The amount of the coloring agent can vary from about 0.1 to about 5% by weight of the composition, preferably from about 0.1 to about 1%.

"Bioavailability" refers to the rate and extent to which the active drug ingredient or therapeutic moiety is absorbed into the systemic circulation from an administered dosage form as compared to a standard or control. Conventional methods for preparing tablets are known. Such methods include dry methods such as direct compression and compression of granulation produced by compaction, or wet methods or other special procedures. Conventional methods for making other forms for administration such as, for example, capsules, suppositories and the like are also well known.

The compounds of Formula I can form salts which are also within the scope of this invention. Reference to a compound of Formulae Ia and Ib herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a compound of Formulae Ia and Ib with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons or sulfurs on various substituents, including enantiomeric forms (which may exist even in the absence of asymmetric carbons), rotameric forms, atropisomers, and diastereomeric forms, are contemplated within the scope of this invention. For example, if a compound of Formula I incorporates a double bond or a fused ring, both the cis- and trans-forms, as well as mixtures, are embraced within the scope of the invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate" "prodrug" and the like, is intended to equally apply to the salt, solvate and prodrug of enantiomers, stereoisomers, rotamers, tautomers, racemates or prodrugs of the inventive compounds.

Diasteromeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diasteromeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formulae Ia and Ib may be atropisomers (e.g., substituted biaryls) and are considered as part of this invention. Enantiomers can also be separated by use of chiral HPLC column.

Polymorphic forms of the compounds of Formula I, and of the salts, solvates and prodrugs of the compounds of Formula I, are intended to be included in the present invention The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled compounds of Formula I (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labelled compounds of Formula I can generally be prepared by following procedures analogous to those disclosed in the Schemes and/or in the Examples hereinbelow, by substituting an appropriate isotopically labelled reagent for a non-isotopically labelled reagent.

The compounds according to the invention have pharmacological properties; in particular, the compounds of Formula I can be useful as α2C adrenoreceptor agonists.

A preferred dosage is about 0.001 to 500 mg/kg of body weight/day of the compound of Formulae Ia and Ib. An especially preferred dosage is about 0.01 to 25 mg/kg of body weight/day of a compound of Formula I, or a pharmaceutically acceptable salt or solvate of said compound.

The compounds of this invention may also be useful in combination (administered together or sequentially) with one or more therapeutic agents such as, for example, glucosteroids, PDE-4 inhibitors, anti-muscarinic agents, cromolyn sodium, $H_1$ receptor antagonists, 5-$HT_1$ agonists, NSAIDs, angiotensin-converting enzyme inhibitors, angiotensin II receptor agonists, β-blockers, β-agonists (including both long and short acting), leukotriene antagonists, diuretics, aldosterone antagonists, ionotropic agents, natriuretic peptides, pain management/analgesic agents, anti-anxiety agents, anti-migraine agents, and therapeutic agents suitable for treating heart conditions, psychotic disorders, and glaucoma.

Suitable steroids include prednisolone, fluticasone (including all ester such as the propionate or furoate esters), triamcinolone, beclomethasone, mometasone (including any ester form such as mometasone furoate), budasamine, ciclesonide betamethasone, dexamethasone, prednisone, flunisolide, and cortisone.

Suitable PDE-4 inhibitors include roflumilast, theophylline, rolipram, piclamilast, cilomilast and CDP-840.

Suitable antiimuscarinic agents include ipratropium bromide and tiatropium bromide.

Suitable $H_1$ antagonists include astemizole, azatadine, azelastine, acrivastine, brompheniramine, cetirizine, chlorpheniramine, clemastine, cyclizine, carebastine, cyproheptadine, carbinoxamine, descarboethoxyloratidine, diphenhydramine, doxylamine, dimethindene, ebastine, epinastine, efletirizeine, fexofenadine, hydroxyzine, ketotifen, loratidine, levocabastine, meclizine, fexofenadine, hydroxyzine, ketotifen, loratadine, levocabastine, meclizine, mizolastine, mequitazine, mianserin, noberastine, norastemizole, picumast, pyrilamine, promethazine, terfenadine, tripelennamine, temelastine, trimeprazine or triprolidine.

Suitable anti-inflammatory agents include aspirin, diclofenac, diflunisal, etodolac, flurbiprofen, ibuprofen, indomethacin, ketoprofen, ketorolac, nabumetone, naproxen, oxaprozin, piroxicam, sulindac, and tolmetin.

Suitable aldosterone antagonists include spironolactone.

Suitable ionotropic agents include digitalis.

Suitable angiotensin II receptor agonists include irbesartan and losartan.

Suitable diuretics include spironolactone, methyclothiazide, bumetanide, torsemide, hydroflumethiazide, trichlormethiazide, hydroclorothiazide, triamterene, ethacrynic acid, methyclothiazide, hydrochlorothiazide, benzthiazide, hydrochlorothiazide, quinethazone, hydrochlorothiazide, chlorthalidone, furosemide, indapamide, hydroclorothiazide, triamterene, trichlormethiazide, hydrochlorothiazide, amiloride HCl, amiloride HCl, metolazone, trichlormethiazide, bendroflumethiazide, hydrochlorothiazide, polythiazide, hydroflumethiazide, chlorthalidone, and metolazone.

Suitable pain management/analgesic agents include Celecoxib, amitriptyline, ibuprofen, naproxen, gabapentin, tramadol, rofecoxib, oxycodone HCl, acetaminophenoxycodone HCl, carbamazepine, amitriptyline, diclofenac, diclofenac, etodolac, fenoprofen calcium, flurbiprofen, ibuprofen, indomethacin, ketoprofen, ketorolac tromethamine, mefenamic acid, meloxicam, nabumetone, naproxen, oxaprozin, piroxicam, sulindac, tolmetin sodium, valdecoxib, diclofenac/misoprostol, oxycontin, vicodin, darvocet, percocet, morphine sulfate, dilaudid, stadol, stadol NS, acetaminophen with codeine, acetaminophen with codeine #4, Lidoderm® patches, ziconotide, duloxetine, roboxetine, gabapentin and pregabalin.

Suitable β-blockers include acebutolol, atenolol, atenolol/chlorthalidone, betaxolol, bisoprolol fumarate, bisoprolol/HCTZ, labetolol, metoprolol tartrate, nadolol, pindolol, propranolol, propranolol/HCTZ, sotalol, and timolol.

Suitable β-agonists include dobutamine, ritodrine, salbutamol, levalbuterol, metaproternol, formoterol, fenoterol, bambuterol, brocaterol, clenbuterol, terbutaline, tulobuterol, epinephrine, isoprenalin, and hexoprenalin.

Suitable leucotriene antagonists include levamisole.

Suitable anti-migraine agents include rovatriptan succinate, naratriptan HCl, rizatriptan benzoate, sumatriptan succinate, zolmitriptan, almotriptan malate, methysergide maleate, dihydroergotamine mesylate, ergotamine tartrate, ergotamine tartrate/caffeine, Fioricet®, Frominal®, Depakene®, and Depakote®.

Suitable anti-anxiety and anti-depressant agents include amitriptyline HCl, bupropion HCl, citalopram hydrobromide, clomipramine HCl, desipramine, fluoxetine, fluvoxamine maleate, maprotiline HCl, mirtazapine, nefazodone HCl, nortriptyline, paroxetine HCl, protriptyline HCl, sertraline HCl, doxepin, and trimipramine maleate.

Suitable angiotensin converting enzyme inhibitors include Captopril, enalapril, enalapril/HCTZ, lisinopril, lisinopril/HCTZ, and Aceon®.

The pharmacological properties of the compounds of this invention may be confirmed by a number of pharmacological assays. The exemplified pharmacological assays which are described later have been carried out with the compounds according to the invention and their salts.

This invention is also directed to pharmaceutical compositions which comprise at least one compound of Formula I or a pharmaceutically acceptable salt or solvate of said compound and at least one pharmaceutically acceptable carrier.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18th Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions or suspensions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 100 mg, preferably from about 1 mg to about 50 mg, more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 500 mg/day, preferably 1 mg/day to 200 mg/day, in two to four divided doses.

Another aspect of this invention is a kit comprising a therapeutically effective amount of at least one compound of Formula I or a pharmaceutically acceptable salt or solvate of said compound and a pharmaceutically acceptable carrier, vehicle or diluent.

Yet another aspect of this invention is a kit comprising an amount of at least one compound of Formula I, or a pharmaceutically acceptable salt or solvate of said compound and an amount of at least one therapeutic agent listed above, wherein the amounts of the two or more ingredients result in desired therapeutic effect.

In general, the compounds in the invention may be produced by a variety of processes know to those skilled in the art and by know processes analogous thereto. The invention disclosed herein is exemplified by the following preparations and examples which should not be construed to limit the scope of the disclosure. Alternative mechanistic pathways and analogous structures will be apparent to those skilled in the art. The practitioner is not limited to these methods.

One skilled in the art will recognize that one route will be optimized depending on the choice of appendage substituents. Additionally, one skilled in the art will recognize that in some cases the order of steps has to be controlled to avoid functional group incompatability.

The prepared compounds may be analyzed for their composition and purity as well as characterized by standard analytical techniques such as, for example, elemental analysis, NMR, mass spectroscopy and IR spectra.

One skilled in the art will recognize that reagents and solvents actually used may be selected from several reagents and solvents well known in the art to be effective equivalents. Hence, when a specific solvent or reagent is mentioned, it is meant to be an illustrative example of the conditions desirable for that particular reaction scheme and in the preparations and examples described below.

Where NMR data are presented, $^1$H spectra were obtained on either a Varian VXR-200 (200 MHz, $^1$H), Varian Gemini-300 (300 MHz), Varian Mercury VX-400 (400 MHz), or Bruker-Biospin AV-500 (500 MHz), and are reported as ppm with number of protons and multiplicities indicated parenthetically. Where LC/MS data are presented, analyses was performed using an Applied Biosystems API-100 mass spectrometer and C18 column, 10-95% $CH_3CN$—$H_2O$ (with 0.05% TFA) gradient. The observed parent ion is given.

The following solvents and reagents may be referred to by their abbreviations in parenthesis:

Me = methyl; Et = ethyl; Pr = propyl; Bu = butyl;
Ph = phenyl, and Ac = acetyl
μl = microliters
AcOEt or EtOAc = ethyl acetate
AcOH or HOAc = acetic acid
ACN = acetonitrile
atm = atmosphere
9-BBN = 9-borabicyclo[3.3.1]nonane
Bn = benzyl
Boc or BOC = tert-butoxycarbonyl
DBU = 1,8-Diaza-7-bicyclo[5.4.0]undecene
DCM or $CH_2Cl_2$: dichloromethane
DMF = dimethylformamide
DMS = dimethylsulfide
DMSO = dimethyl sulfoxide
dppf = 1,2'-bis(diphenylphosphino)ferrocene
EDCI = 1-(3-dimethylaminopropyl)-3-ethylcarbodiimide
g = grams
h = hour
LAH = lithium aluminum hydride
LCMS = liquid chromatography mass spectrometry
min = minute
mg = milligrams
mL = milliliters
mmol = millimoles
MeOH: methanol MS = mass spectrometry
NMR = nuclear magnetic resonance spectroscopy
RT or rt = room temperature (ambient, about 25° C.).
TEA or Et₃N = triethylamine
TFA = trifluoroacetic acid
THF = tetrahydrofuran
TLC = thin layer chromatography
TMS = trimethylsilyl
TosMIC = tosylmethyl isocyanide

EXAMPLES

The compounds of this invention can be prepared through the general approach outlined in the following schemes. These schemes are being provided to illustrate the present invention. Group A is defined in these schemes in accordance with the definition in the invention; i.e., as an optionally substituted 5-membered heteroaryl, heterocyclyl or heterocyclenyl ring containing 1-3 heteroatoms. The depiction of A as an unsubstituted imidazole is not in any way to be considered a limitation of the invention scope Scheme 1 shows an approach in which S1 (Z=halogen or activated alcohol) is converted to S2 ($Z^1$=substituted aryl or heteroaryl) via a metal catalyzed or metal-facilitated process (such as Stille coupling, Suzuki coupling, Negishi coupling or nucleophilic substitution reaction), with an appropriately substituted aryl or heteroaryl partner. Compound S2 is then reacted with an electrophilic compound S3. In various embodiments, R is a carboxaldehyde (leading to coupling by reductive amination), a carboxylic acid (leading to amide coupling) or methylene chloride (leading to coupling by alkylation). In the case where R is a carboxylic acid (S3b), the resulting amide product may be subsequently reduced to S4. Exemplary procedures employed in the synthesis of various S2 and S4 fragments are described in the examples below.

SCHEME 1:

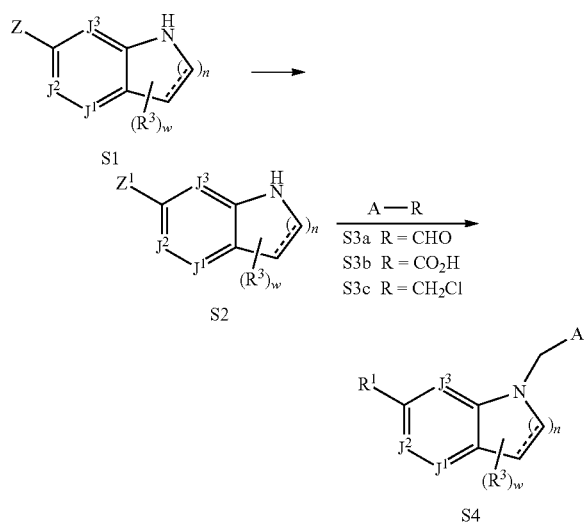

where A = optionally substituted (e.g. $R^5$ or a protecting group), heteroaryl (e.g. imidazole), heterocyclyl, or heteocyclenyl group According to another embodiment, compound S6 ($Z^1$=substituted aryl or heteroaryl; X=N, O, or S) is prepared by metal-catalyzed or metal facilitated coupling, such as one of those listed above, between S5 (Z=halogen or activated alcohol) and an appropriately substituted aryl or heteroaryl partner. Compound S3c, optionally protected with R'=BOC, trityl, Bn, —SO₂NMe₂ or another appropriate group, is then reacted with S6, under basic conditions when X=N and under Lewis acidic conditions when X=O or S), to provide S7.

SCHEME 2:

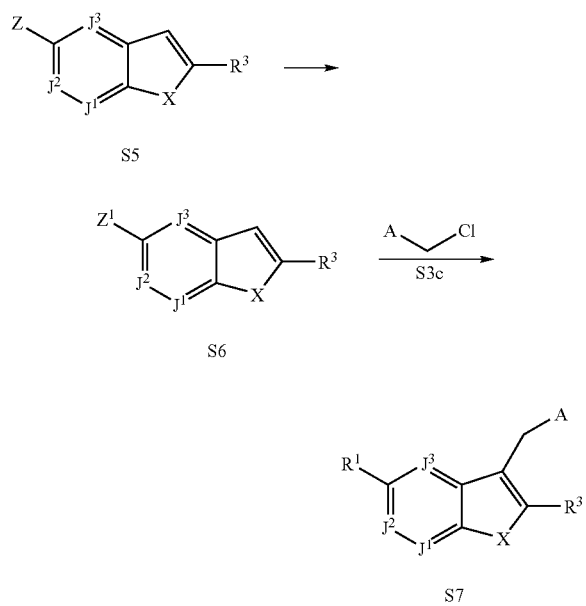

where A = optionally substituted (e.g., $R^5$ or a protecting group) heteroaryl (e.g. imidazole), heteocyclyl, or heterocyclenyl group According to another embodiment (Scheme 3), an appropriately substituted 4-phenol or 4-thiophenol (S8, X=O or S, Z=halogen or protected alcohol) is reacted with S9a or S9b wherein Y is an appropriate leaving group (such as Cl, Br, I, or activated alcohol) and R is a nitrile (—CN) or ester (—CO₂R'). Subsequent cyclization of S10 occurs under acidic or Lewis acidic conditions. The resulting ketone S11 is coupled with an appropriately substituted aryl or heteroaryl partner via a metal catalyzed or metal-facilitated process, such as Stille coupling, Suzuki coupling, or Negishi coupling to afford S12. Homologation to aldehyde S13 is accomplished by one of numerous methodologies including a Wittig/hydrolysis sequence, Horner-Emmons/hydrolysis or related approaches (see Synthesis, 1979, 633-664). Compound S14 (Y=Br, I, or other appropriate group; R'=BOC, trityl, Bn, —SO₂NMe₂ or other appropriate group) may be activated via Grignard or other metal-facilitated process, and reacted with S13. This step is followed by an elimination to provide alkene S16, which is further reduced to aniline S17 by hydrogenation or other appropriate method. Final deprotection by a method appropriate to the R' group provides S18. Alternatively, compound S15 is converted directly to S17 by a deoxygenation (for example, treatment with Et₃SiH/TFA, NaI/Me₂SiCl₂ or other appropriate method).

SCHEME 3

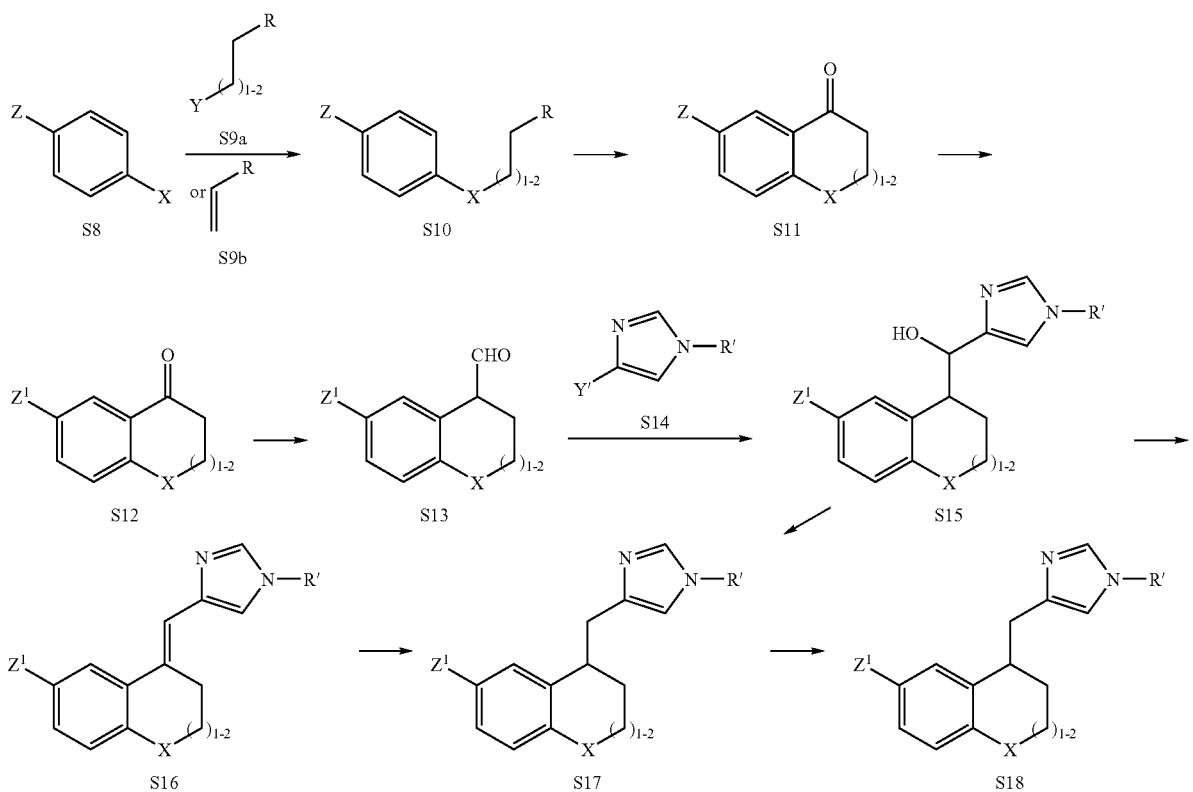

According to another embodiment, the biaryl compound S12 is converted to compound S16 by an alternative synthetic route as detailed in Scheme 4. Compound S12 is reduced to alcohol S19 by a known method such as treatment with LiAlH$_4$, borane, NaBH$_4$, or the like. This alcohol is then activated and displaced with an appropriate reagent, such as PPh$_3$HBr or P(OEt)$_3$, to afford a Wittig or Horner-Emmons type intermediate S20. Subsequent treatment with an appropriate base and a protected imidazole aldehyde S21 under standard Wittig or Horner-Emmons conditions provides S16, which may be further modified as detailed previously.

SCHEME 4

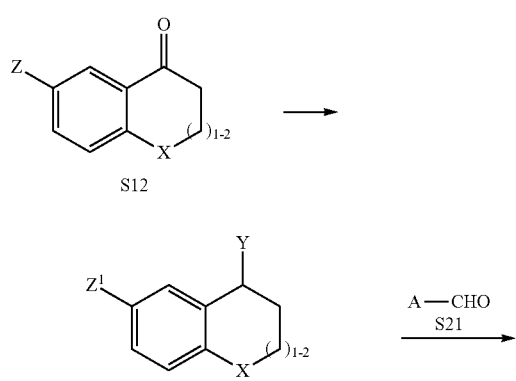

-continued

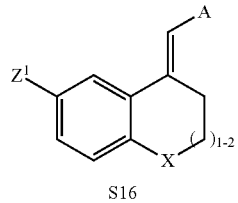

where A = optionally substituted (e.g., R$^5$ or a protecting group) heteroaryl (e.g., imidazole), heteocyclyl, or heterocyclenyl group According to another embodiment, the biaryl compound S12 is converted to compound S18 as detailed in Scheme 5. Compound S12 is subjected to a two-carbon homologation to yield S21 by one of a number of known methods (see Synthesis, 1979, 633-664, and U.S. Pat. No. 6,841,684). These methods include the sequence of a Wittig or Horner-Emmons (with an appropriate base and a reagent such as diethyl 2,2-diethoxyethylphosphonate or (1,3-dioxolan-2-ylmethyl)tripheneylphosphonium bromide) followed by hydrogenation (with a catalyst such as Pd/C in H$_2$) and hydrolysis. An alternative method is the sequence of a Wittig or Horner-Emmons (with an appropriate base and a reagent such trimethyl phosphonoacetate or (methoxycarbonylmethyl)triphenylphosphonium bromide) followed by hydrogenation (with a catalyst such as Pd/C in H$_2$) and transformation (reduction or reduction/oxidation) to the corresponding aldehyde S21. Other alternative methods also include Wittig (with methyl triphenylphosphonium bromide) and hydroboration protocols (with 9-BBN and CO). The compound S21 is then converted to S18 by the sequence of TosMIC/NaCN and then NH$_3$/MeOH.

SCHEME 5

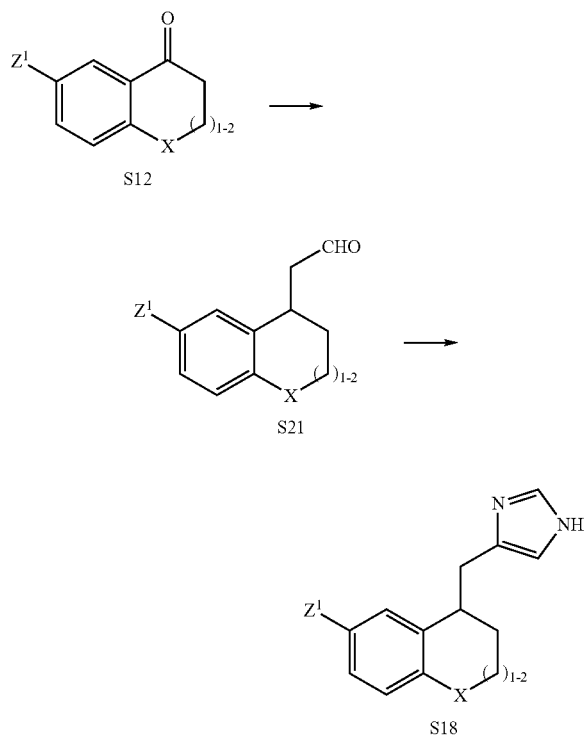

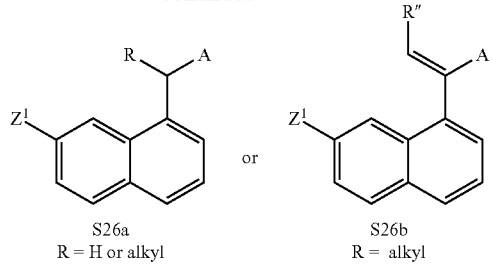

where A = optionally substituted (e.g. $R^5$ or a protecting group) heteroaryl (e.g., imidazole), heterocyclyl, or heterocyclenyl group The starting materials and reagents used in preparing compounds described are either available from commercial suppliers such as Aldrich Chemical Co. (Wisconsin, USA) and Acros Organics Co. (New Jersey, USA) or were prepared by literature methods known to those skilled in the art.

Compounds of formulae S4, S7, S16, S18, and S26 can be prepared by the general methods outlined above. Exemplary compounds were prepared as described in the examples below or from starting materials known in the art. These examples are being provided to further illustrate the present invention. They are for illustrative purposes only; the scope of the invention is not to be considered limited in any way thereby Preparative Example 1

According to another embodiment (Scheme 6), an appropriately substituted naphthalene (S22, Z=halogen or activated alcohol) is coupled with an appropriately substituted aryl or heteroaryl partner via a metal-catalyzed or metal-facilitated process, such as Stille coupling, Suzuki coupling, or Negishi coupling. The resulting compound, S23, is acylated via a Friedel-Crafts or other related methodology to provide S24. An appropriately protected compound S14 (Y'=Br, I, or other appropriate group) is then reacted with S24 via a Grignard or related metal-facilitated addition. The alcohol is then removed by deoxygenation (with conditions such as $Et_3SiH$/TFA or $NaI/Me_2SiCl_2$) or eliminated (to form an olefin when R=alkyl).

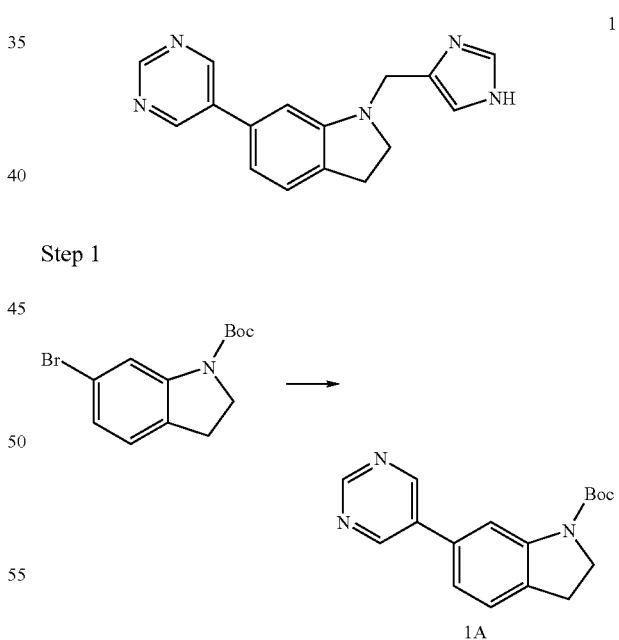

Step 1

SCHEME 6

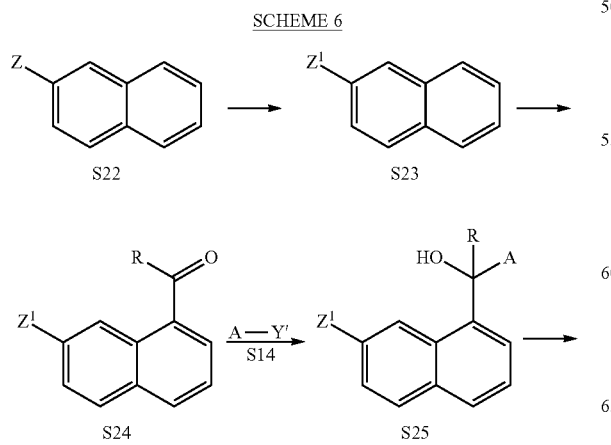

A mixture of N-Boc-6-bromoindoline (0.5 g, 1.68 mmol), pyrimidine 5-boronic acid (0.249 g, 2.01 mmol), $Na_2CO_3$ (0.355 g, 3.35 mmol), and $Pd(PPh_3)_4$ (0.194 g, 0.17 mmol) in $DMF-H_2O$ (1:1, 10 mL) was heated at 90° C. for 4 h in a 15 mL sealed tube. The reaction was cooled to RT and extracted with DCM. The organic extracts were dried over $MgSO_4$ and concentrated. Chromatography (0-10% of (9:1 $MeOH/NH_3$) in $CH_2Cl_2$) afforded 1A (346 mg).

Steps 2-3

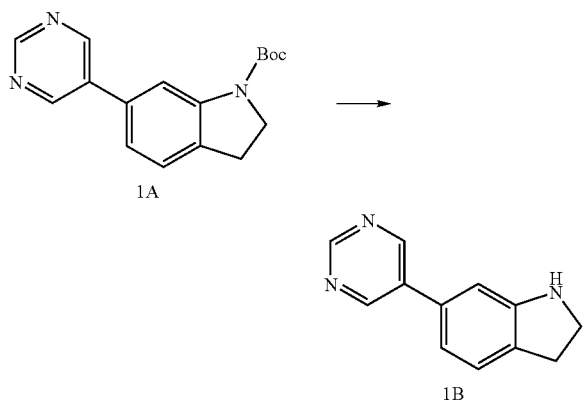

A solution of 1A (0.346 g, 1.2 mmol) in DCM (5 mL) was treated with TFA (1 mL) and stirred for 3 h. The reaction was then quenched with 25% aqueous NH₄OH and extracted with DCM The combined organic layer was dried (Na₂SO₄), filtered and concentrated to give 1B (250 mg).

A mixture of 1B (241 mg, 1.2 mmol) and 4-imidazolecarboxaldehyde (141 mg, 1.5 mmol) in DCM (5 mL) was treated with HOAc (3 drops). The mixture was stirred for 5 min, treated with NaBH(OAc)₃ (388 mg, 1.8 mmol) and then stirred overnight. The reaction was diluted with DCM, washed with aqueous K₂CO₃, dried (MgSO₄) and concentrated. Chromatography (0-10% of (9:1 MeOH/NH₃) in CH₂Cl₂) afforded the title compound 1 (176 mg). LCMS m/z 278 (MH+).

Preparative Example 2

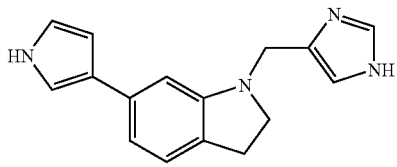

Steps 1-3

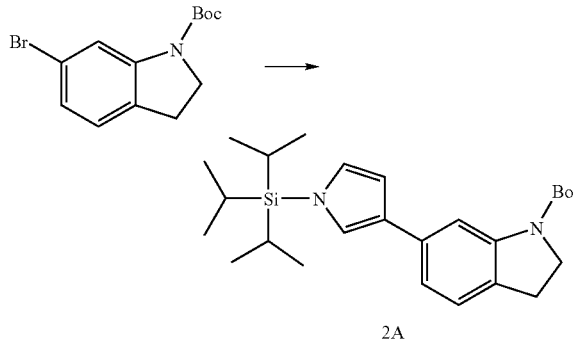

A mixture of N-Boc-6-bromoindoline (0.25 g, 0.84 mmol), 1-(triisopropylsilyl)-pyrrole-3-boronic acid (0.448 g, 1.67 mmol), aqueous K₂CO₃ (0.17M, 5 mL), and PdCl₂(dppf) (0.069 g, 0.08 mmol) in acetonitrile (5 mL) was heated at 80° C. overnight in a 15 mL sealed tube. The reaction was cooled to RT and extracted with DCM. The organic extracts were dried over MgSO₄ and concentrated. Chromatography (0-10% of (9:1 MeOH/NH₃) in CH₂Cl₂) afforded 2A (202 mg).

In a manner similar to that described in Example 1 (Steps 2-3), 2A was treated with TFA and then reacted with 4-imidazolecarboxaldehyde and NaBH(OAc)₃ to afford the title compound 2. LCMS m/z 265 (MH+).

Preparative Example 3

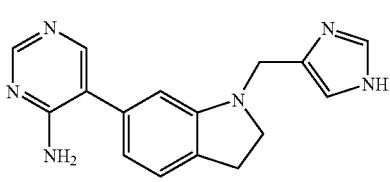

Steps 1-3

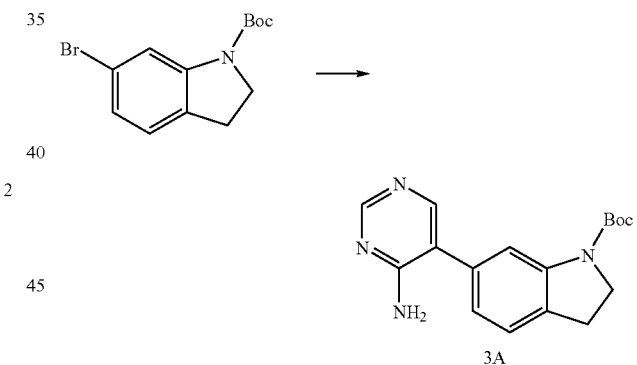

A mixture of N-Boc-6-bromoindoline (0.66 g, 2.2 mmol), bis(pinacolato)diboron (1.118 g, 4.4 mmol), KOAc (0.65 g, 6.6 mmoL), and PdCl₂(dppf) (0.069 g, 0.08 mmol) in dioxane (8 mL) was heated at 100° C. for 1.5 h in a 15 mL sealed tube and then cooled to RT. The reaction was treated with 4-amino-5-bromopyrimidine (0.76 g, 4.4 mmol) and aqueous K₂CO₃ (4 mL, 1M) and heated at 100° C. overnight. The mixture was diluted with aqueous K₂CO₃ and extracted with DCM. The organic extracts were dried over MgSO₄ and concentrated. Chromatography (0-10% of (9:1 MeOH/NH₃) in CH₂Cl₂) afforded 3A (657 mg) as a brown oil.

In a manner similar to that described in Example 1 (Steps 2-3), 3A was treated with TFA and then reacted with an 4-imidazolecarboxaldehyde and NaBH(OAc)₃ to afford the title compound 3. LCMS m/z 293 (MH+).

Preparative Example 4

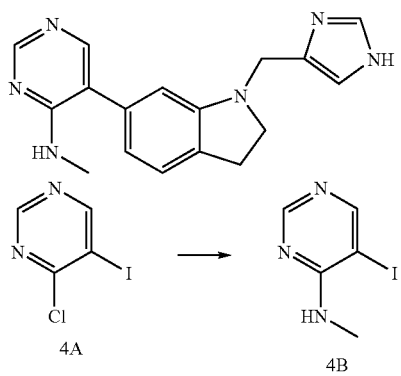

A solution of 4-chloro-5-iodopyrimidine 4A (2.03 g, 8.44 mmol) in 40% aqueous $MeNH_2$ solution was stirred at RT for 17 h. The mixture was then extracted with DCM (2×150 ml). The combined organic phase were dried concentrated to give 5-iodo-4-methylaminopyrimidine 4B (1.55 g, 78%) as an orange solid which was used for the next step without further purification.

In a manner similar to that described in Example 3, 4B was converted to the title compound 3. LCMS m/z 307 (MH+).

Preparative Example 5

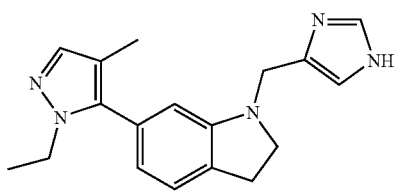

Steps 1-4

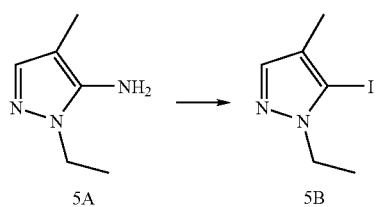

To a stirred mixture of 1-ethyl-4-methyl-1H-pyrazol-5-amine (5A, 2.50 g, 0.020 mol) in $CH_2I_2$ (45 mL) at −10° C., isoamyl nitrite (24.0 mL, 0.180 mol) was added slowly. The mixture was stirred at 80° C. for 2 h, cooled and concentrated under vacuum. The concentrated residue was redissolved in DCM and loaded onto pre-wetted silica pad. The pad was rinsed with hexanes (2 L). The desired product was then eluted with EOAct (1.5 L) and concentrated. Chromatography (0-50% EtOAc/hexanes) provided 5B (2.89 g).

In a manner similar to that described in Example 3 (Steps 1-3), 5B was converted to the title compound 5. LCMS m/z 308 (MH+).

Preparative Example 6

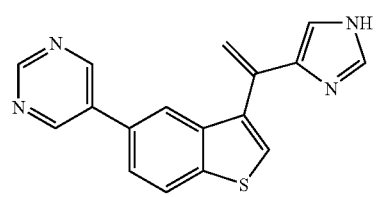

Step 1

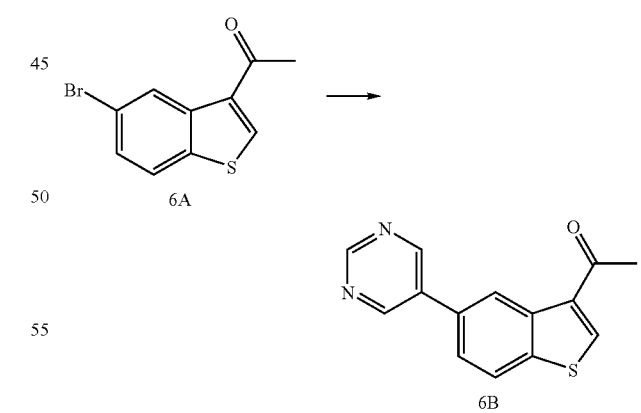

To a solution of 6-bromobenzothiophene (10.0 g, 0.047 mol) and AcCl (4.43 g, 4.0 ml, 0.056 mol) in 1,2-dichloroethane (200 mL) was added $SnCl_4$ (1.0 M/heptane, 56 mL) at 0° C. The mixture was allowed to reach RT and then stirred for 20 h. The mixture was poured onto ice/$H_2O$ and extracted with DCM. The organic layer was washed with sat. aqueous $NaHCO_3$, dried and concentrated. Flash chromatography (EtOAc/hexanes, 1:9 then 1:4) afforded 6A (5.6 g).

Step 2

To a stirred mixture of 6A (300 mg, 1.81 mmol) in dioxane (4 mL) and $H_2O$ (1 mL) was added 5-pyrimidinyl boronic acid (293 mg, 2.36 mmol), Pd(dppf)$C_{12}$-DCM (96 mg, 0.118 mmol) and $K_3PO_4$ (750 mg, 3.54 mmol). The mixture was stirred at 80° C. under $N_2$ for 12 h, diluted with EtOAc, washed with $H_2O$, dried and concentrated. Flash chromatography (EtOAc/hexanes, 4:1) afforded 6B (220 mg).

Steps 3-4

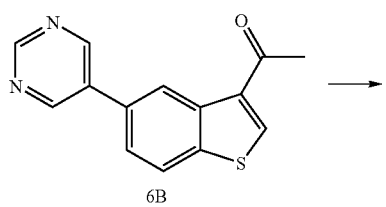

6B

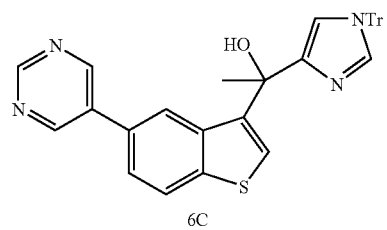

6C

To a solution of 4-iodo-1-tritylimidazole (10.0 g, 0.047 mol) in DCM (10 mL) was added EtMgBr (3.0 M in Et₂O, 0.39 mL) slowly at 0° C. The mixture was stirred for 30 min at RT and then was added to a solution of the 6B (270 mg, 1.06 mmol) in DCM (5 mL) dropwise via syringe at 0° C. After stirring for 30 min, the reaction mixture was quenched with sat. aqueous NH₄Cl, extracted with DCM, dried and concentrated. Flash chromatography (MeOH/DCM, 1:15) afforded 6C (200 mg).

Compound 6C (40 mg, 0.071 mmol) was stirred in DCM (5 mL) and TFA (5 mL) at RT for 18 h. The TFA and DCM were removed in vacuo. Preparative TLC (7N NH₃-MeOH in DCM, 1:10) afforded the title compound 6 (8 mg). MS m/z 305 (MH+).

Preparative Example 7

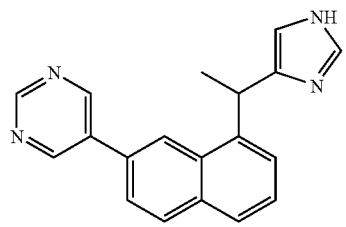

7

Step 1

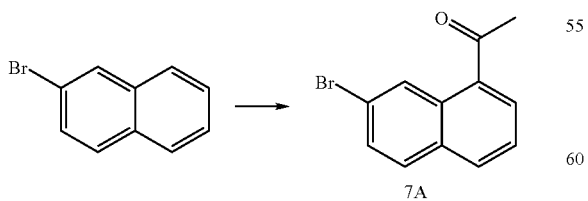

A solution of 2-bromonaphthalene (12.6 g, 61.3 mmol) in DCM (100 mL) was treated with AlCl₃ (25 g, 190 mmol) at −10° C. and stirred until a dark green mixture was observed. The reaction was cooled to −78° C. and treated slowly with AcCl (9.1 mL, 127 mmol). After 5 h, the reaction was warmed to 0° C. and treated slowly with aqueous HCl (1 M, 50 mL). After cessation of bubbling, the layers were separated. The aqueous layer was then extracted with DCM (2×). The combined organic layers were dried over Na₂SO₄, filtered and concentrated to a clear oil. Chromatography (2-10% EtOAc/hexanes) provided 7A as a white solid.

Step 2

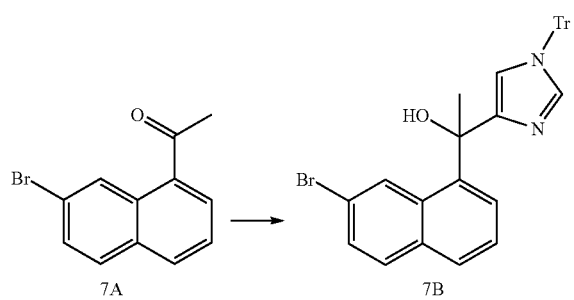

7A                                    7B

Ethyl magnesium bromide (3.0 M/Et₂O, 1.34 ml; 4.03 mmol) was added in small aliquots to a suspension of 1-trityl-4-iodo-imidazole in anhydrous DCM (12 ml) at RT under nitrogen. The clear solution was stirred for one hour and then treated with a solution of 7A (0.67 g, 2.69 mmol) in DCM (4.0 mL) in small aliquots via syringe. After stirring 19 h, the solution was cooled in ice bath, quenched with sat. aqueous NH₄Cl (25 mL), and extracted with DCM. The combined extracts were washed with brine and dried over anhydrous Na₂SO₄. The mixture was purified twice by flash chromatography (SiO₂, 0-10% MeOH/DCM gradient; then SiO₂, MeCN/DCM gradient) to provide 7B (0.53 g).

Step 3

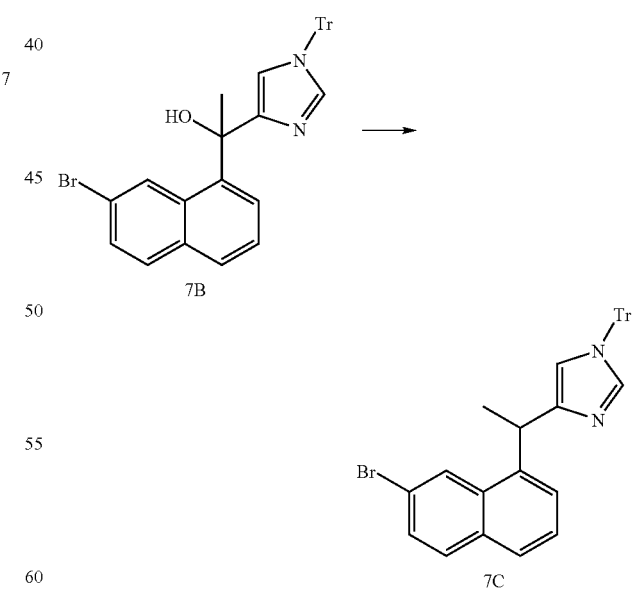

A solution of 7B (0.31 g, 0.55 mmol) and Et₃SiH (1.1 mmol) in anhydrous DCM (4.0 mL) was cooled in ice bath and treated dropwise with boron trifluoride etherate (0.7 mL; 6.6 mmol). After the addition, the ice bath was removed, and the solution was stirred at RT for 4 h. The reaction was quenched with sat. aqueous Na₂CO₃. The organic layer was separated. The aqueous layer was extracted with DCM. The combined extracts were dried over anhydrous Na₂SO₄ and purified by preparative TLC (SiO₂, DCM) to provide 7C (0.030 g).

Steps 4-5

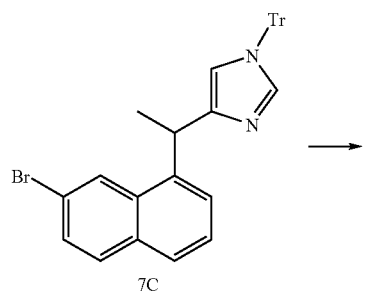

A mixture of 7C (30 mg, 0.055 mmol), pyrimidine-5-boronic acid (21 mg, 0.166 mmol), Pd(PPh₃)₄ (16 mg, 0.014 mmol), and Na₂CO₃ (53 mg, 0.498 mmol) in 4:1 dimethoxyethane:water (2.0 mL) were microwaved for 2700 seconds at 120° C. The mixture was extracted with DCM, washed with water and dried over anhydrous Na₂SO₄. The product was purified twice by preparative TLC (SiO₂, 5% MeOH (NH₃)/DCM) to give 7D (0.022 g).

A cooled (ice bath) solution of 7D (20 mg) in anhydrous DCM (3.0 mL) was treated with TFA (0.3 mL). After stirring for 7 h at RT, the solvent was removed using reduced pressure. The product was purified by preparative TLC (SiO₂, 15% MeOH (NH₃)/DCM) to provide the title compound 7 (5.7 mg). LCMS m/z 301 (MH⁺).

Preparative Example 8

8

Step 1

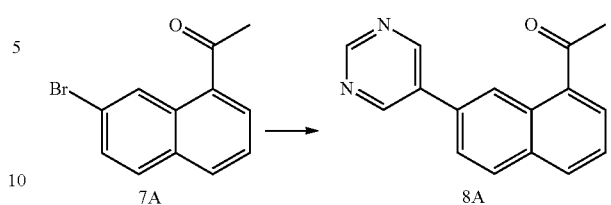

A mixture of 7A (0.71 g, 2.85 mmol), pyrimidine-5-boronic acid (0.42 g, 3.38 mmol), Pd(PPh₃)₄ (0.33 g, 0.285 mmol), and Na₂CO₃ (0.6 g, 5.7 mmol) in DMF (10 mL) and water (10 mL) were heated in a pressure tube at 90° C. for 2 h. After cooling to RT, the black mixture was extracted with DCM (4×30 mL). The combined extracts were washed with brine (3×30 mL) and dried over anhydrous Na₂SO₄. The product was purified by flash chromatography (SiO₂, 0-10% MeOH/DCM) to provide 8A (0.33 g).

Step 2

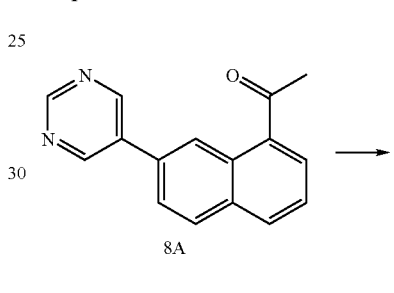

In a manner similar to that described in Example 7 (Step 2), compound 8A was treated with the Grignard reagent of 1-trityl-4-iodo-imidazole to provide 8B. LCMS m/z 559 (MH+)

Step 3

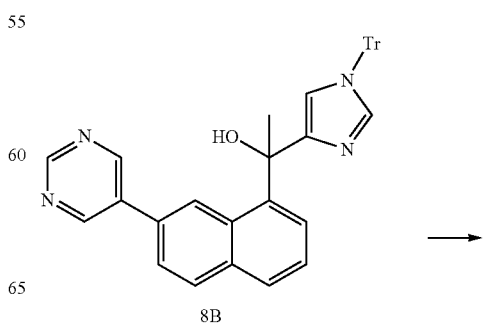

Step 2

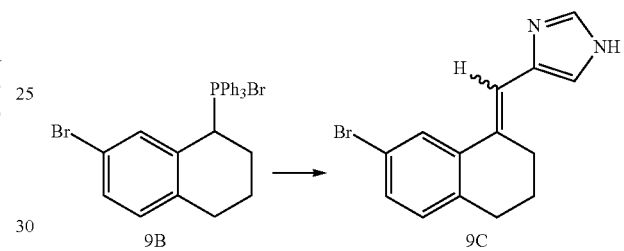

A mixture of 9A (2.89 g, 12.7 mmol) and Ph₃P—HBr (4.37 g, 12.73 mmol) in benzene (10 mL) was refluxed for 24 h. After cooling to RT, the solid was filtered, washed with benzene, and then stirred with diethyl ether for 30 minutes. The solid was the filtered, washed sequentially with Et₂O and acetone, and then vacuum dried. Yield of 9B: 2.99 g.

Steps 3-4

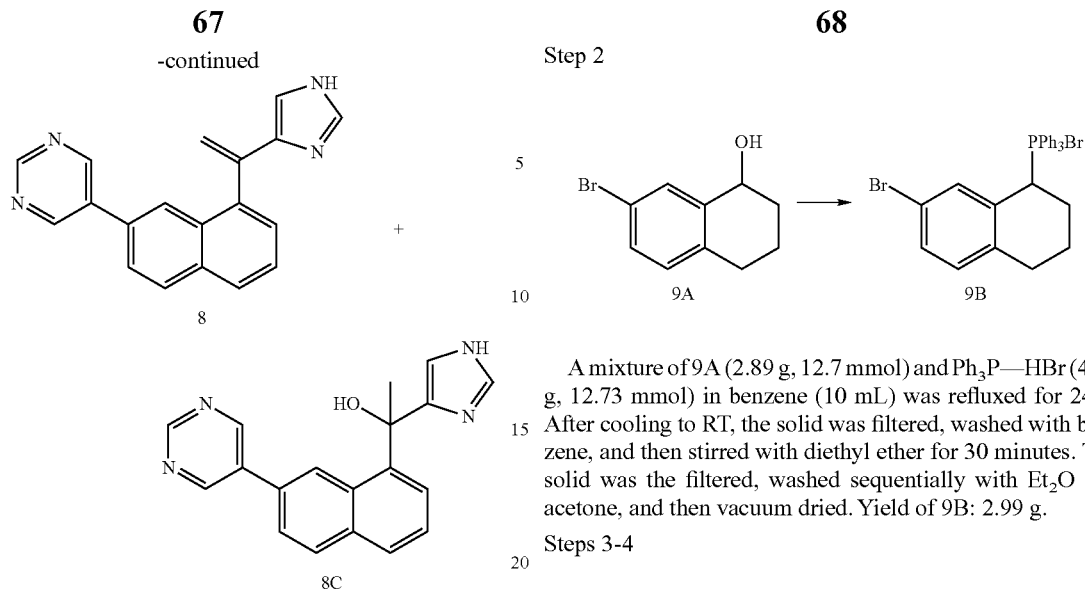

A suspension of imidazole-4-carboxyaldehyde (1.14 g, 11.85 mmol) in absolute ethanol (20 mL) in a two-necked flask was warmed to a bath temperature of 60° C. A solution of KOtBu (1.0 M/THF, 12.0 mL) was added dropwise. After the addition, the solution was stirred for 20 min and then cannulated into a mixture of 9B (5.95 g, 10.77 mmol) in absolute EtOH (30 mL) at 80° C. under nitrogen. The reaction was heated to reflux for 19 h. After cooling to RT, the solvents were removed using reduced pressure. The residue was treated with water and extracted with DCM. The combined extracts were washed with water and dried over anhydrous Na₂SO₄. The product was purified twice by flash chromatography (SiO₂, 0-10% MeOH/DCM). Yield of 9C: 0.63 g.

In a manner similar to that described in Example 7 (Step 4), a mixture of 9C, pyrimidine-5-boronic acid and Pd(dppf)C₁₂-DCM was microwaved (20 min, 120° C.) to afford the title compound 9. LCMS m/z 289 (MH+).

A mixture of compound 8B (30 mg), TFA (0.06 mL) and Et₃SiH (0.06 mL) was stirred at RT for 4 h. The reaction was concentrated and purified by preparative TLC (SiO₂, 10% MeOH(NH₃)/DCM) to provide 8C (0.009 g, LCMS m/z 317, MH+) and the title compound 8 (0.010 g, LCMS m/z 299, MH+).

Preparative Example 9

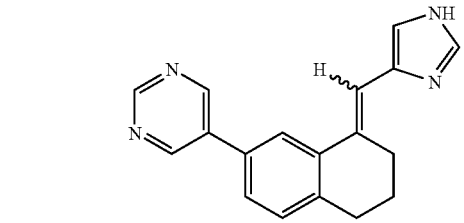

Step 1

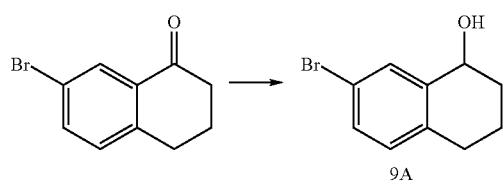 [SMILES: O=C1CCCc2ccc(Br)cc21 ; OC1CCCc2ccc(Br)cc21]

Sodium borohydride (0.53 g, 14 mmol) was added in small portions to a pre-cooled solution of 7-bromo-1-tetralone in DCM (15 mL) and MeOH (30 mL). After the addition, the mixture was stirred at RT for 90 min and then quenched with water (60 mL). The organic layer was separated. The aqueous layer was extracted with Et₂O (4×30 mL). The combined extracts were washed sequentially with 1.0 N aq. HCl (3×20 mL), sat. aq. Na₂CO₃ (3×20 mL), and brine (2×20 mL), and then dried over anhydrous Na₂SO₄. Removal of the solvent using reduced pressure yielded 9A as an oil (3.02 g).

Preparative Example 10

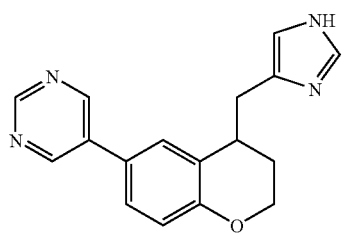

Steps 1-2

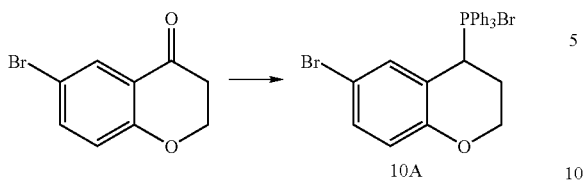

In a manner similar to that described in Example 9 (Steps 1-2), 6-bromochroman-4-one (10 g) was sequentially reduced with NaBH$_4$ and treated with Ph$_3$P—HBr to afford the phosphonium salt 10A as a white solid (39% overall yield).

Step 3

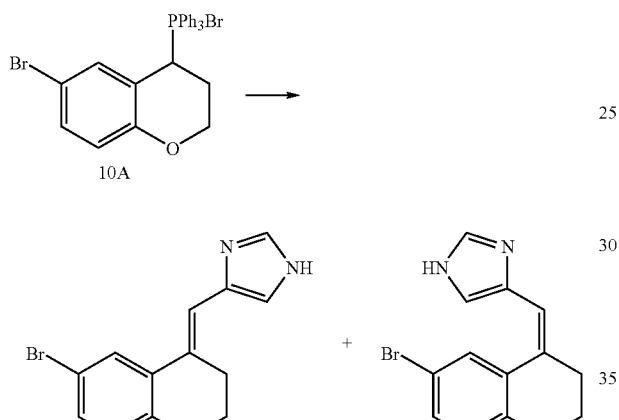

A suspension of imidazole-4-carboxyaldehyde (144 mg, 1.5 mmol) in absolute EtOH (3 mL) was treated with KOtBu (1N/THF, 1.5 mL) and warmed for several minutes until it became homogeneous. In a separate vessel, a suspension of the phosphonium salt 10A (750 mg, 1.35 mmol) in EtOH (5 mL) was refluxed briefly under N$_2$ and then treated dropwise with the first solution. The reaction was refluxed overnight, cooled to RT, and concentrated. The residue was diluted with EtOAc (50 mL) and water (25 mL). The organic layer was isolated, dried over Na$_2$SO$_4$, and concentrated in vacuo. The E-isomer 10B and Z-isomer 10C were purified by preparative TLC.

Steps 4-5

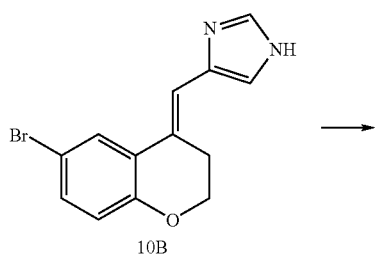

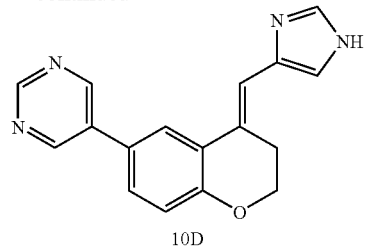

A mixture of 10B (29 mg, 0.1 mmol), pyrimidine-5-boronic acid (37 mg, 0.3 mmol), Pd(dppf)Cl$_2$ (16 mg, 0.014 mmol), and Na$_2$CO$_3$ (64 mg, 6 eq.) in 4:1 dimethoxyethane: water (2 mL) were microwaved for 12 min at 120° C. The mixture was partitioned between EtOAc and water. The organic layer was separated, dried over Na$_2$SO$_4$, and concentrated in vacuo. The product was purified twice by preparative TLC (14:1 DCM: 5% of 7N NH$_3$-MeOH) to provide 10D as a cream colored solid. LCMS m/z 291 (MH$^+$).

A mixture of 10D (30 mg, 0.1 mmol) in EtOH (10 mL) was treated with 10% Pd/C and hydrogenated (1 atm H$_2$) for 24 h and then at 30 psi H$_2$ for 3 h. The reaction was filtered, concentrated, and subjected to flash chromatography (7N NH$_3$-MeOH in DCM) to afford the title compound 10 as a pale yellow solid (10 mg, 33% yield). LCMS m/z 293 (MH$^+$).

In a similar manner, compound 10C was converted to 10E. LCMS m/z 291 (MH+).

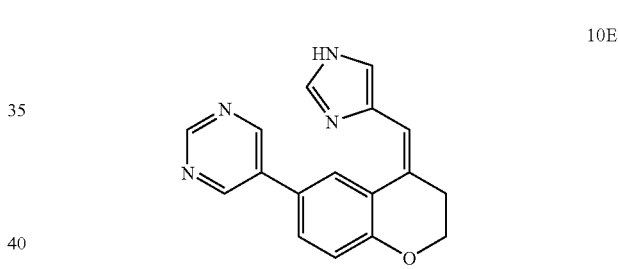

Preparative Example 11

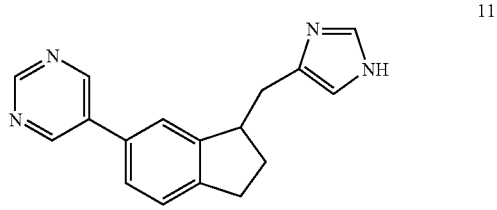 [SMILES: c1ncc(-c2ccc3c(c2)C(Cc2c[nH]cn2)CC3)cn1]

Steps 1-2

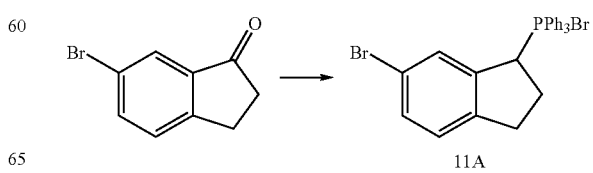

In a manner similar to that described in Example 9 (Steps 1-2), 6-bromo-1-indanone (11 g) was sequentially reduced with NaBH₄ and treated with Ph₃P—HBr to afford the phosphonium salt 11A (68% overall yield).

Steps 3-5

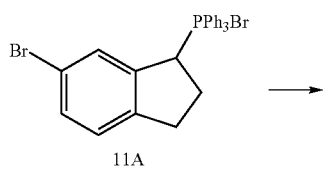

11A

→

11B

In a manner similar to that described in Example 10 (Steps 3-4), compound 11A was sequentially treated with KOtBu/imidazole-4-carboxyaldehyde and then pyrimidine-5-boronic acid/Pd(dppf)Cl₂ to afford compound 11B. LCMS m/z 275 (MH⁺).

In a manner similar to that described in Example 10 (Step 5), compound 11B was hydrogenated (45 psi H₂) to afford the title compound 11 as a brown solid (80% yield). LCMS m/z 277 (MH⁺).

Preparative Example 12

12

Steps 1-3

3A

12A

Compound 3A is treated with 2-chloroacetaldehyde and NaOAc at pH 6.2 using conditions described by Kluge (Journal of Heterocyclic Chemistry 1978, 15, 119-121) to afford compound 12A.

In a manner similar to that described in Step 1 (Steps 2-3), 12A is deprotected with TFA and then treated with 4-imidazolecarboxaldehyde and NaBH(OAc)₃ to afford the title compound 12.

An alternative approach to the title compound 12 is shown below.

Alternate Steps 1-2

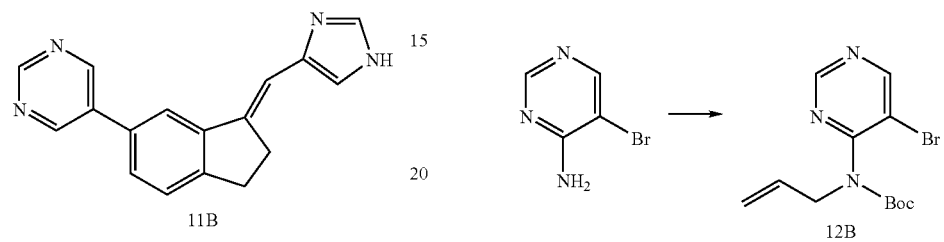

4-Amino-5-bromopyrimidine is sequentially treated with (BOC)₂O and 4-dimethylaminopyridine and then reacted with allyl bromide and an appropriate base to afford compound 12B.

Alternate Steps 3-4

12B → 12C

Compound 12B is reacted with ozone and dimethyl sulfide. The resulting aldehyde is then cyclized by treatment with AcOH to afford 8-bromo-imidazopyrimidine (12C).

Alternate Steps 5-7

12C +  →

12D

Compound 12C is coupled with N-Boc-6-bromoindoline in a manner similar to that previously described in Example 3 (Step 1). The resulting biaryl compound (12D) is deprotected with TFA and then reacted with 4-imidazolecarboxaldehyde and NaBH(OAc)₃ to afford the title compound 12.

Preparative Example 13

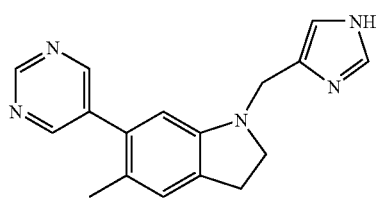

Steps 1-3

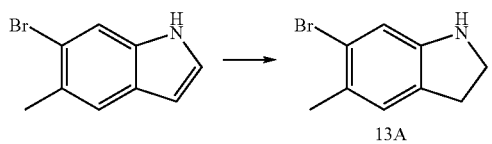

A solution of 6-bromo-5-methylindole (1.00 g, 4.75 mmol) in AcOH (150 mL) was treated with NaBH₃CN (0.897 g, 14.3 mmol) while maintaining a temperature of −10° C. The mixture was then stirred at RT overnight and concentrated. The resulting residue was treated with aqueous K₂CO₃, and extracted with DCM (3×100 mL). The combined organic layers were dried over MgSO₄, concentrated and purified by column chromatography (0-75% EtOAc/hexanes) to afford 6-bromo-5-methylindoline (13A, 716 mg).

In a manner similar to that described previous examples, 13A was coupled with pyrimidine 5-boronic acid and then treated with 4-imidazolecarboxaldehyde to afford the title compound 13. LCMS m/z 292 (MH⁺).

Preparative Examples 14-15

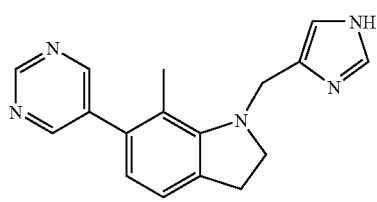

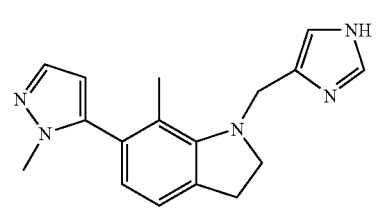

In a manner similar to that described in Example 13, compounds 14 and 15 are synthesized starting with commercially available 6-bromo-7-methylindole.

Preparative Example 16

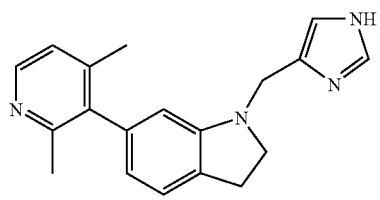

Step 1

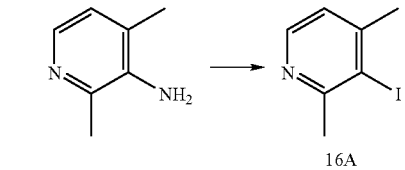

In a manner similar to that described in Example 5 (Step 1), commercially available 3-amino-2,4-dimethylpyridine was treated with isoamyl nitrite and CH₂I₂ to provide 3-iodo-2,4-dimethylpyridine (16A).

Step 2

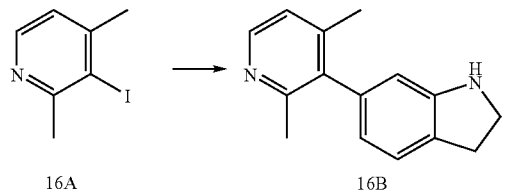

In a manner similar to that described in Example 3 (Step 1), 16A was coupled with 6-bromoindoline to afford 16B.

Step 3

In a manner similar to that described in Example 1 (Step 3), 16B is treated with 4-imidazolecarboxaldehyde to afford the title compound 16.

Preparative Example 17

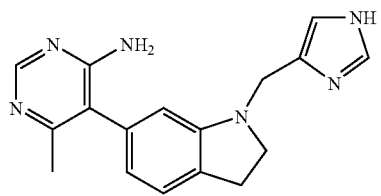

Steps 1-2

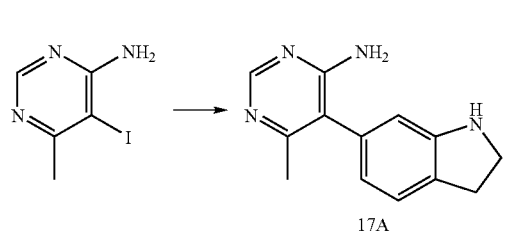

In a manner similar to that described in Example 3 (Step 1), commercially available 4-amino-5-iodo-6-methyl-pyrimidine is coupled with 6-bromoindoline to afford 17A.

In a manner similar to that described in Example 1 (Step 3), 17A is treated with 4-imidazolecarboxaldehyde to afford the title compound 17.

Preparative Example 18

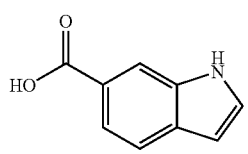

Step 1

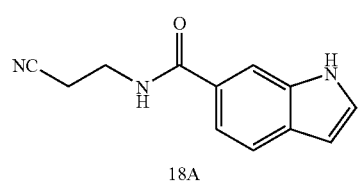

Indole-6-carboxylic acid is coupled with 3-aminopropionitrile using an amide coupling reagent such as EDCl to provide 18A.

Step 2

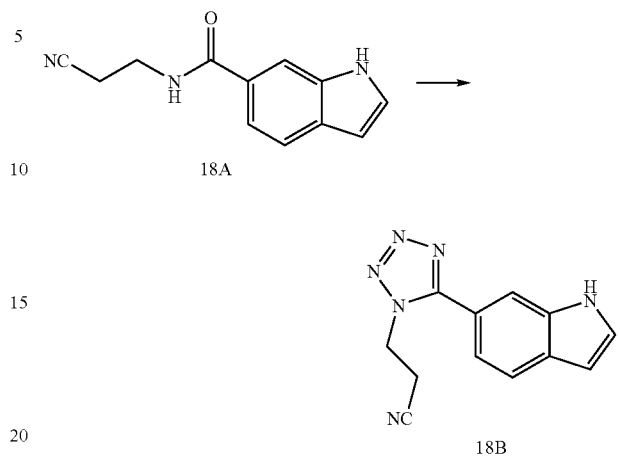

In a manner similar to that described in *J. Med. Chem.* 2006, 49(12), 3659, compound 18A is reacted with DIAD, Ph$_3$P and TMSN$_3$ to give tetrazole 18B.

Steps 3-5

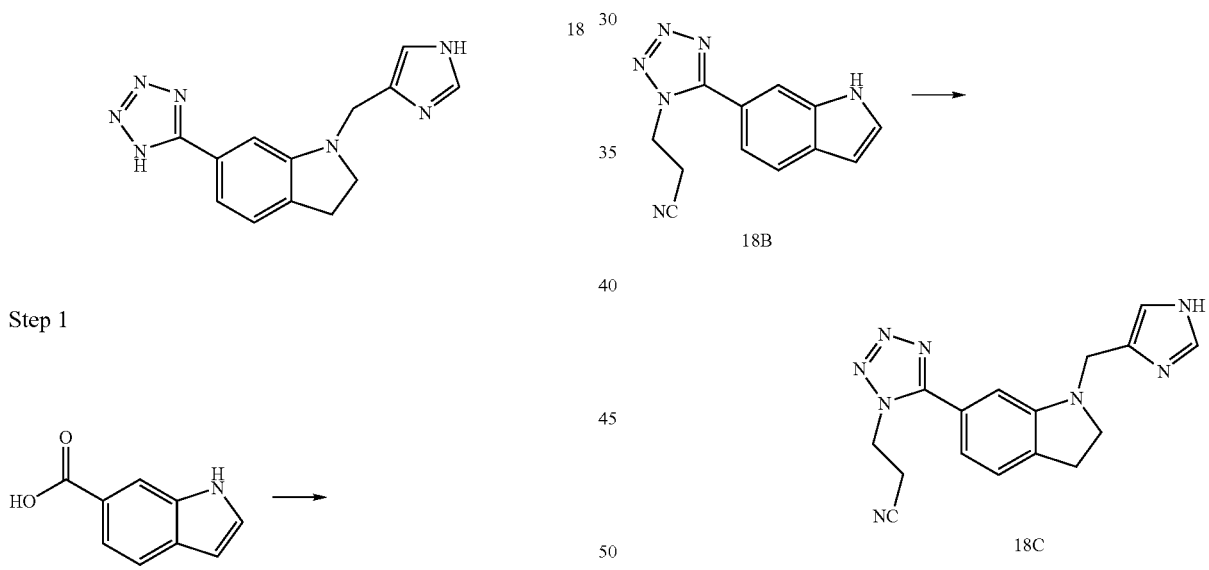

In a manner similar to that described in Example 13 (Step 1) and Example 1 (Step 3), 18B is reduced with NaBH$_3$CN in AcOH and then reacted with 4-imidazolecarboxaldehyde to afford 18C.

Final deprotection of 18C is accomplished by treatment with a base such as NaOH, DBU, or LiOH to afford the title compound 18.

In a manner similar to that described above (Steps 1-4), indole-6-carboxylic acid is coupled with various primary amines followed by cyclization with DIAD, Ph$_3$P and TMSN$_3$, reduction with NaBH$_3$CN in AcOH, and reaction with 4-imidazolecarboxaldehyde to provide the compounds indicated below:

| Amine starting material | Cpd | Structure |
|---|---|---|
| MeNH₂ | 18D | |
| EtNH₂ | 18E | |
| nPrNH₂ | 18F | |
| iPrNH₂ | 18G | |
| MeO(CH₂)₂NH₂ | 18H | |
| NC-CH₂-NH₂ | 18I | |
| NC-CH₂CH₂-NH₂ | 18J | |

Preparative Example 19

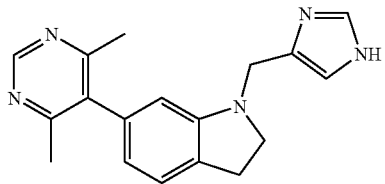

Steps 1-3

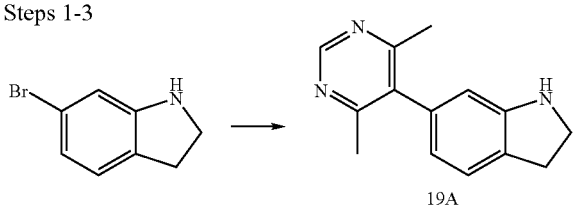

In a manner similar to that found in Example 3 (Step 1), a mixture of 6-bromoindoline, bis(pinacolato)diboron, KOAc, and $PdCl_2$(dppf) in dioxane was heated at 100° C. for 1.5 h in a sealed tube and then cooled to RT. The reaction was treated with 4,6-dimethyl-5-bromopyrimidine and aqueous $K_2CO_3$ and then heated at 100° C. overnight. Aqueous work-up and chromatography afforded 19A as a brown oil.

In a manner similar to that described in Example 1 (Steps 2-3), 19A was treated with TFA and then reacted with 4-imidazolecarboxaldehyde and $NaBH(OAc)_3$ to afford the title compound 19. LCMS m/z 306 ($MH^+$).

The following compounds were prepared following essentially the same procedures as in the examples above.

| Cpd | Structure | MS (MH+) |
|---|---|---|
| 100 | 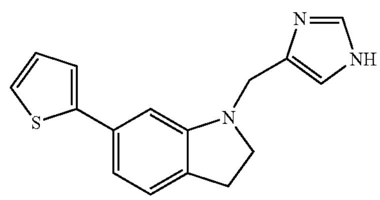 [SMILES: c1csc(-c2ccc3c(c2)N(Cc2c[nH]cn2)CC3)c1] | 282 |
| 101 | 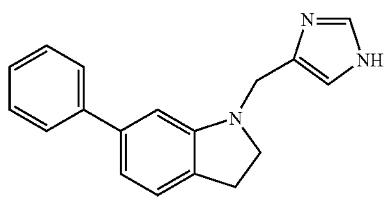 [SMILES: c1ccc(-c2ccc3c(c2)N(Cc2c[nH]cn2)CC3)cc1] | 276 |
| 102 | 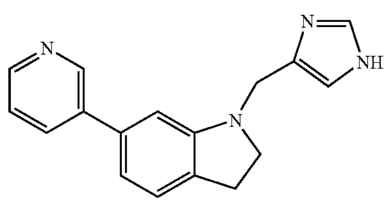 [SMILES: c1cncc(-c2ccc3c(c2)N(Cc2c[nH]cn2)CC3)c1] | 277 |
| 103 | 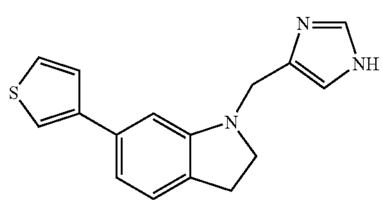 [SMILES: c1nc(CN2CCc3ccc(-c4ccsc4)cc32)c[nH]1] | 282 |
| 104 | 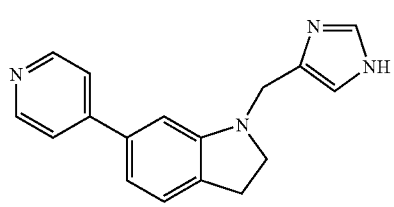 [SMILES: c1cc(-c2ccc3c(c2)N(Cc2c[nH]cn2)CC3)ccn1] | 277 |

-continued

| Cpd | Structure | MS (MH+) |
|---|---|---|
| 105 | 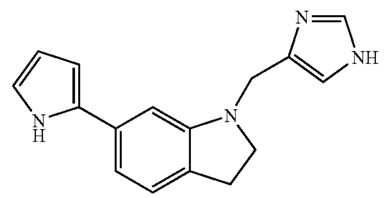 [SMILES: c1c[nH]c(-c2ccc3c(c2)N(Cc2c[nH]cn2)CC3)c1] | **1H NMR: 8.85(s, 1H), 7.52(s, 1H), 7.05(d, 1H), 6.95(d, 1H), 6.85(s, 1H), 6.75(d, 1H), 6.40(t, 1H), 6.15(d, 1H), 4.41(s, 2H), 3.36(t, 2H), 2.95(t, 2H). |
| 106 | 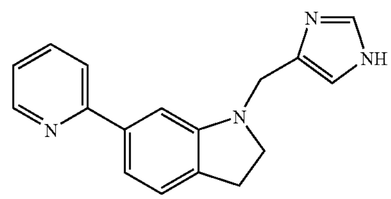 [SMILES: c1ccc(-c2ccc3c(c2)N(Cc2c[nH]cn2)CC3)nc1] | 277 |
| 107 | 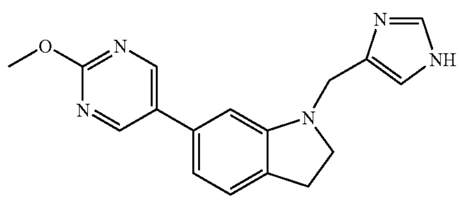 [SMILES: COc1ncc(-c2ccc3c(c2)N(Cc2c[nH]cn2)CC3)cn1] | 308 |
| 108 | 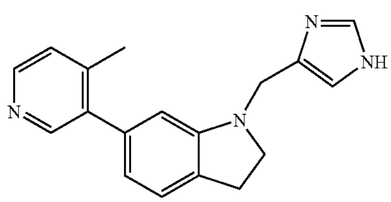 [SMILES: Cc1ccncc1-c1ccc2c(c1)N(Cc1c[nH]cn1)CC2] | 291 |
| 109 | 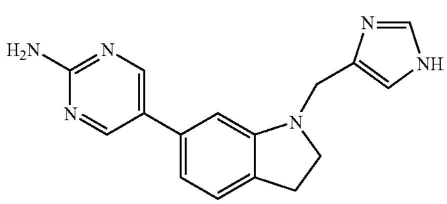 [SMILES: Nc1ncc(-c2ccc3c(c2)N(Cc2c[nH]cn2)CC3)cn1] | 293 |
| 110 | 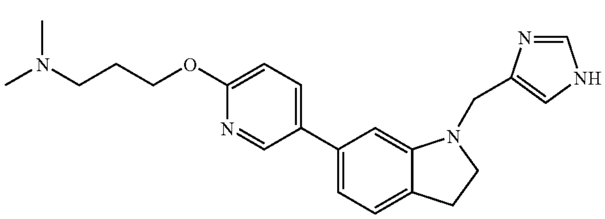 [SMILES: CN(C)CCCOc1ccc(-c2ccc3c(c2)N(Cc2c[nH]cn2)CC3)cn1] | 278 |
| 111 | 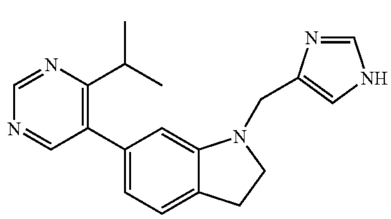 [SMILES: CC(C)c1ncncc1-c1ccc2c(c1)N(Cc1c[nH]cn1)CC2] | 320 |

-continued

| Cpd | Structure | MS (MH+) |
|---|---|---|
| 112 | 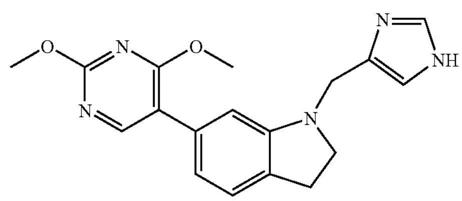 [SMILES: COc1ncc(-c2ccc3c(c2)N(Cc2c[nH]cn2)CC3)c(OC)n1] | 338 |
| 113 | 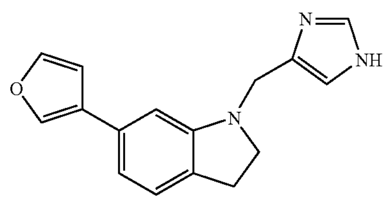 [SMILES: c1nc(CN2CCc3ccc(-c4ccoc4)cc32)c[nH]1] | 266 |
| 114 | 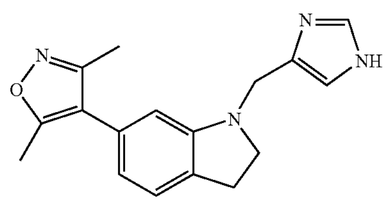 [SMILES: Cc1noc(C)c1-c1ccc2c(c1)N(Cc1c[nH]cn1)CC2] | 295 |
| 115 | 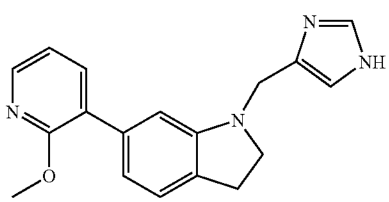 [SMILES: COc1ncccc1-c1ccc2c(c1)N(Cc1c[nH]cn1)CC2] | 307 |
| 116 | 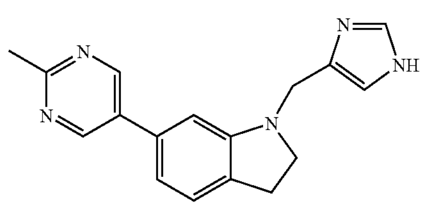 [SMILES: Cc1ncc(-c2ccc3c(c2)N(Cc2c[nH]cn2)CC3)cn1] | 292 |
| 117 | 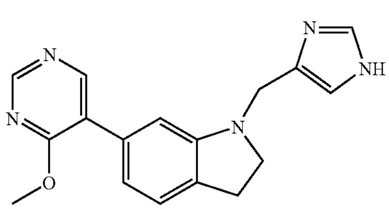 [SMILES: COc1ncncc1-c1ccc2c(c1)N(Cc1c[nH]cn1)CC2] | 308 |
| 118 | 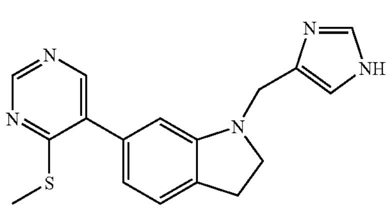 | 324 |

-continued

| Cpd | Structure | MS (MH+) |
|---|---|---|
| 119 | 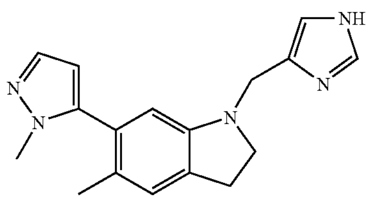 [SMILES: Cc1cc2c(cc1-c1ccnn1C)N(Cc1c[nH]cn1)CC2] | 294 |
| 120 | 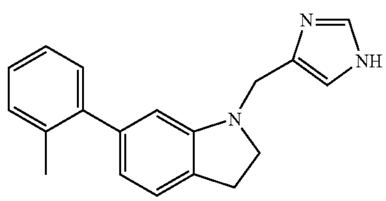 | 290 |
| 121 | 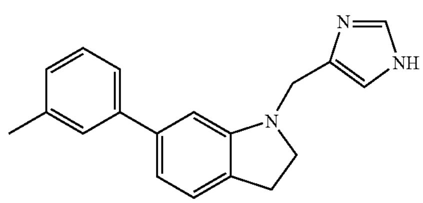 [SMILES: Cc1cccc(-c2ccc3c(c2)N(Cc2c[nH]cn2)CC3)c1] | 290 |
| 122 | 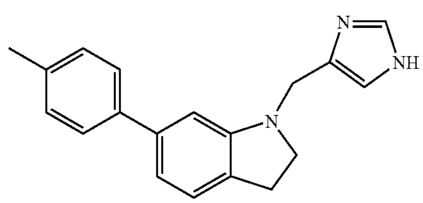 [SMILES: Cc1ccc(-c2ccc3c(c2)N(Cc2c[nH]cn2)CC3)cc1] | 290 |
| 123 | 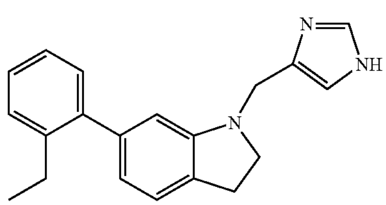 [SMILES: CCc1ccccc1-c1ccc2c(c1)N(Cc1c[nH]cn1)CC2] | 304 |
| 124 | 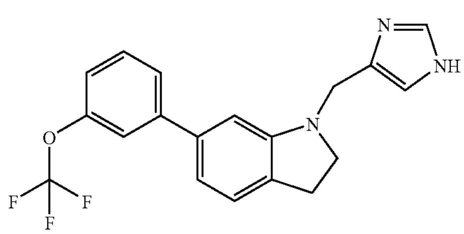 [SMILES: FC(F)(F)Oc1cccc(-c2ccc3c(c2)N(Cc2c[nH]cn2)CC3)c1] | 360 |
| 125 | 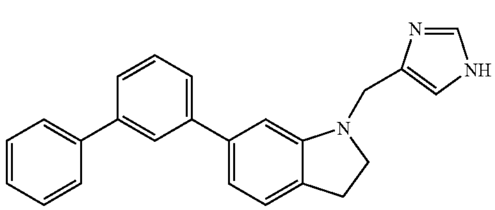 [SMILES: c1ccc(-c2cccc(-c3ccc4c(c3)N(Cc3c[nH]cn3)CC4)c2)cc1] | 352 |

| Cpd | Structure | MS (MH+) |
|---|---|---|
| 126 | 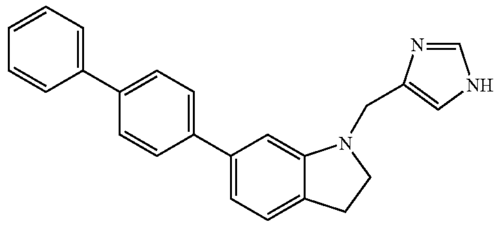 [SMILES: c1ccc(-c2ccc(-c3ccc4c(c3)N(Cc3c[nH]cn3)CC4)cc2)cc1] | 352 |
| 127 | 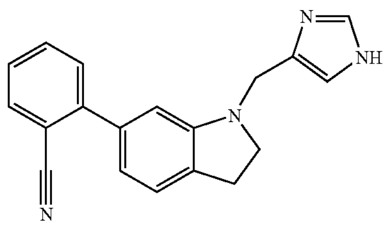 [SMILES: N#Cc1ccccc1-c1ccc2c(c1)N(Cc1c[nH]cn1)CC2] | 301 |
| 128 | 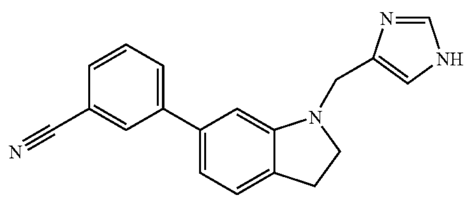 [SMILES: N#Cc1cccc(-c2ccc3c(c2)N(Cc2c[nH]cn2)CC3)c1] | 301 |
| 129 | 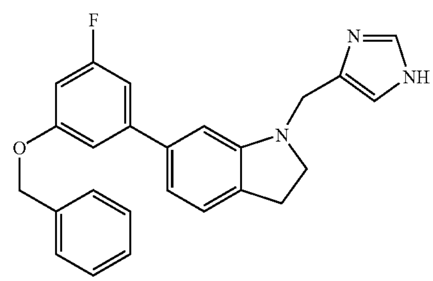 [SMILES: Fc1cc(OCc2ccccc2)cc(-c2ccc3c(c2)N(Cc2c[nH]cn2)CC3)c1] | 400 |
| 130 | 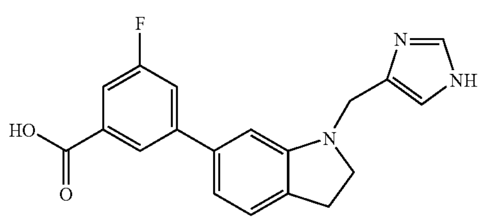 [SMILES: O=C(O)c1cc(F)cc(-c2ccc3c(c2)N(Cc2c[nH]cn2)CC3)c1] | 338 |
| 131 | 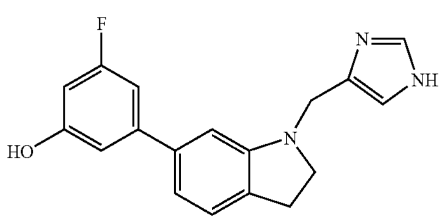 [SMILES: Oc1cc(F)cc(-c2ccc3c(c2)N(Cc2c[nH]cn2)CC3)c1] | 310 |
| 132 | 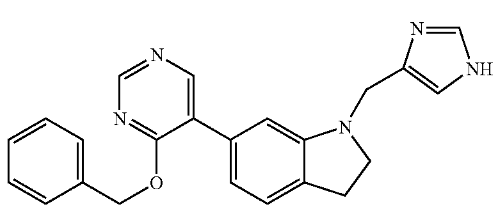 [SMILES: c1ccc(COc2ncncc2-c2ccc3c(c2)N(Cc2c[nH]cn2)CC3)cc1] | 384 |

-continued

| Cpd | Structure | MS (MH+) |
|---|---|---|
| 133 | 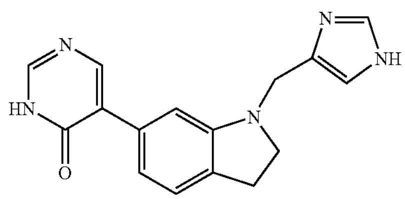 [SMILES: O=c1[nH]cncc1-c1ccc2c(c1)N(Cc1c[nH]cn1)CC2] | 294 |
| 134 | 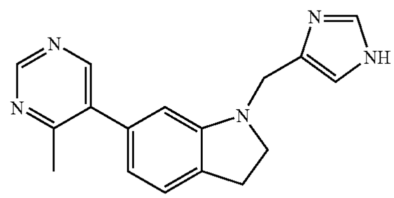 [SMILES: Cc1ncncc1-c1ccc2c(c1)N(Cc1c[nH]cn1)CC2] | 292 |
| 135 | 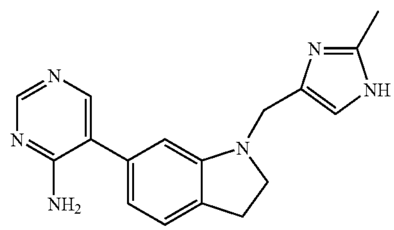 [SMILES: Cc1nc(CN2CCc3ccc(-c4cncnc4N)cc32)c[nH]1] | 307 |
| 136 | 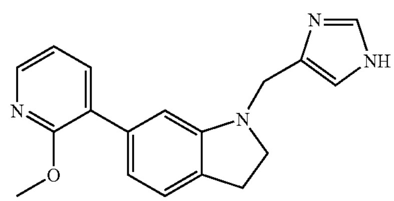 [SMILES: COc1ncccc1-c1ccc2c(c1)N(Cc1c[nH]cn1)CC2] | 307 |
| 137 | 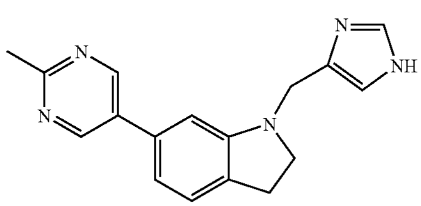 [SMILES: Cc1ncc(-c2ccc3c(c2)N(Cc2c[nH]cn2)CC3)cn1] | 292 |
| 138 | 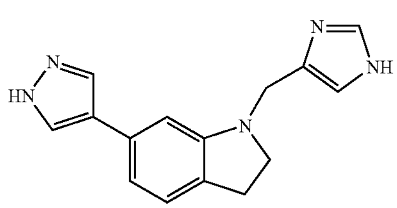 [SMILES: c1nc(CN2CCc3ccc(-c4cn[nH]c4)cc32)c[nH]1] | 266 |
| 139 | 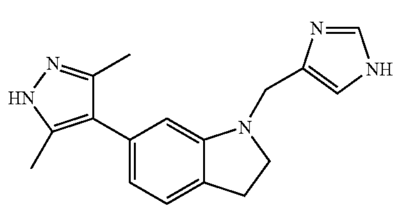 [SMILES: Cc1n[nH]c(C)c1-c1ccc2c(c1)N(Cc1c[nH]cn1)CC2] | 294 |

-continued
| Cpd | Structure | MS (MH+) |
|---|---|---|
| 140 | 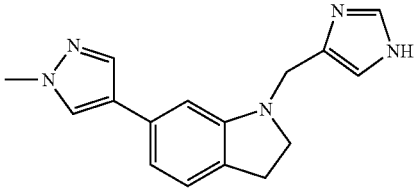 [SMILES: Cn1cc(-c2ccc3c(c2)N(Cc2c[nH]cn2)CC3)cn1] | 280 |
| 141 | 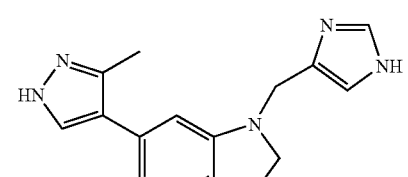 | 280 |
| 142 | 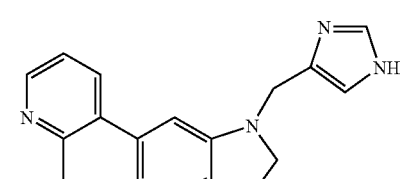 | 291 |
| 143 | 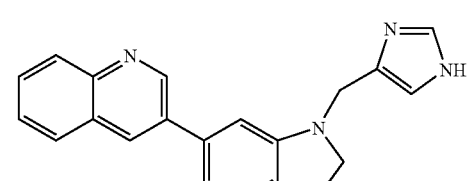 | 327 |
| 144 | 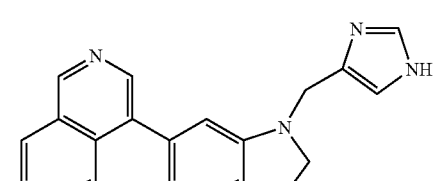 | 327 |
| 145 | 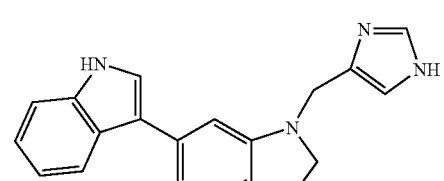 | 315 |
| 146 | 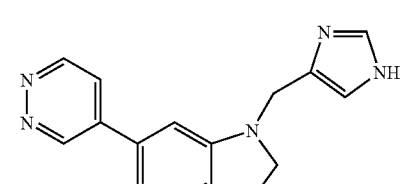 | 278 |

-continued
| Cpd | Structure | MS (MH+) |
|---|---|---|
| 147 | 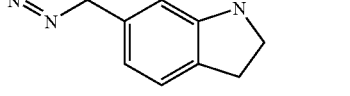 | 278 |
| 148 | 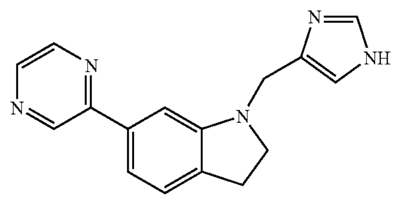 [SMILES: c1cnc(-c2ccc3c(c2)N(Cc2c[nH]cn2)CC3)cn1] | 278 |
| 149 | 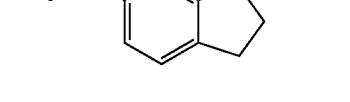 | 279 |
| 150 | 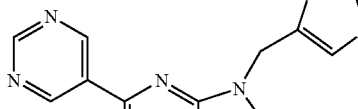 | 348 |
| 151 | 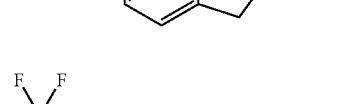 | 280 |
| 152 | 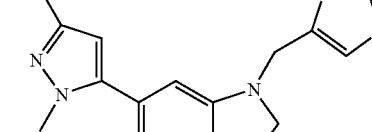 | 369 |
| 153 | 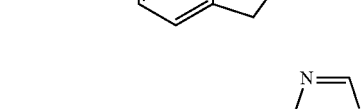 | 315 |

| Cpd | Structure | MS (MH+) |
|---|---|---|
| 154 | 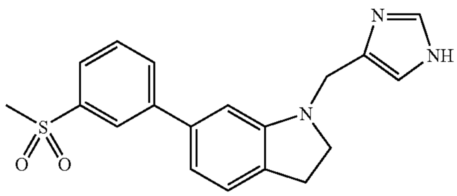 [SMILES: CS(=O)(=O)c1cccc(-c2ccc3c(c2)N(Cc2c[nH]cn2)CC3)c1] | 354 |
| 155 | 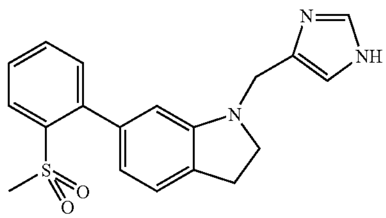 [SMILES: CS(=O)(=O)c1ccccc1-c1ccc2c(c1)N(Cc1c[nH]cn1)CC2] | 354 |
| 156 | 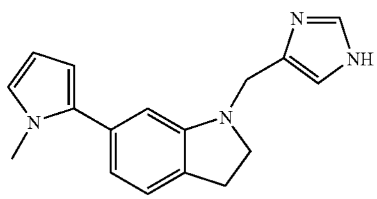 [SMILES: Cn1cccc1-c1ccc2c(c1)N(Cc1c[nH]cn1)CC2] | 279 |
| 157 | 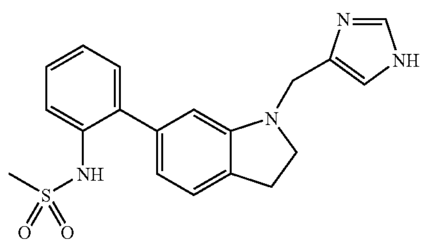 [SMILES: CS(=O)(=O)Nc1ccccc1-c1ccc2c(c1)N(Cc1c[nH]cn1)CC2] | 369 |
| 158 | 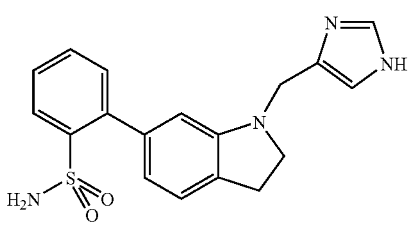 [SMILES: NS(=O)(=O)c1ccccc1-c1ccc2c(c1)N(Cc1c[nH]cn1)CC2] | 355 |
| 159 | 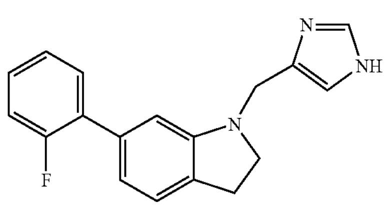 | 294 |
| 160 | 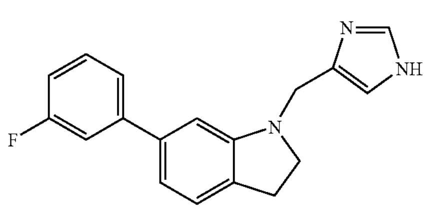 [SMILES: Fc1cccc(-c2ccc3c(c2)N(Cc2c[nH]cn2)CC3)c1] | 294 |

-continued

| Cpd | Structure | MS (MH+) |
|---|---|---|
| 161 | 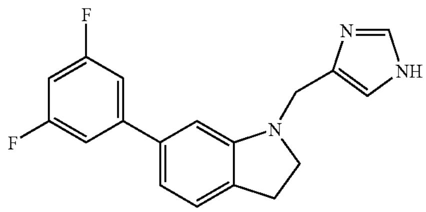 [SMILES: Fc1cc(F)cc(-c2ccc3c(c2)N(Cc2c[nH]cn2)CC3)c1] | 312 |
| 162 | 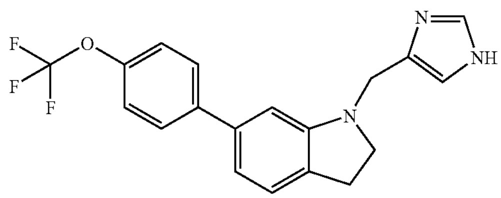 [SMILES: FC(F)(F)Oc1ccc(-c2ccc3c(c2)N(Cc2c[nH]cn2)CC3)cc1] | 360 |
| 163 | 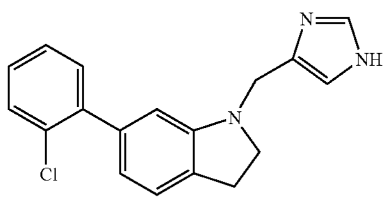 [SMILES: Clc1ccccc1-c1ccc2c(c1)N(Cc1c[nH]cn1)CC2] | 310 |
| 164 | 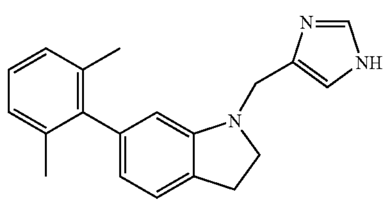 [SMILES: Cc1cccc(C)c1-c1ccc2c(c1)N(Cc1c[nH]cn1)CC2] | 304 |
| 165 | 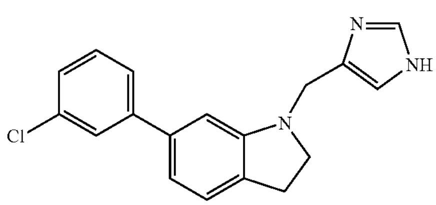 [SMILES: Clc1cccc(-c2ccc3c(c2)N(Cc2c[nH]cn2)CC3)c1] | 310 |
| 166 | 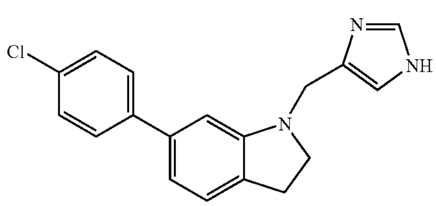 [SMILES: Clc1ccc(-c2ccc3c(c2)N(Cc2c[nH]cn2)CC3)cc1] | 310 |
| 167 | 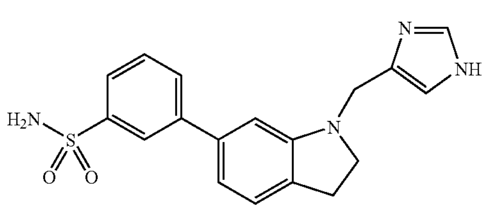 [SMILES: NS(=O)(=O)c1cccc(-c2ccc3c(c2)N(Cc2c[nH]cn2)CC3)c1] | 355 |

-continued

| Cpd | Structure | MS (MH+) |
|---|---|---|
| 168 | 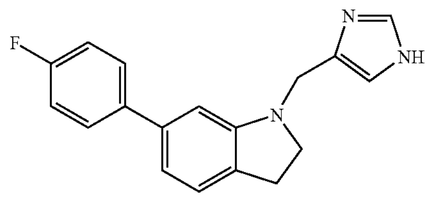 [SMILES: Fc1ccc(-c2ccc3c(c2)N(Cc2c[nH]cn2)CC3)cc1] | 294 |
| 169 | 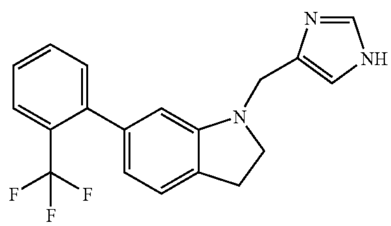 [SMILES: FC(F)(F)c1ccccc1-c1ccc2c(c1)N(Cc1c[nH]cn1)CC2] | 344 |
| 170 | 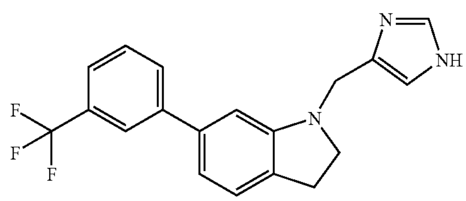 [SMILES: FC(F)(F)c1cccc(-c2ccc3c(c2)N(Cc2c[nH]cn2)CC3)c1] | 344 |
| 171 | 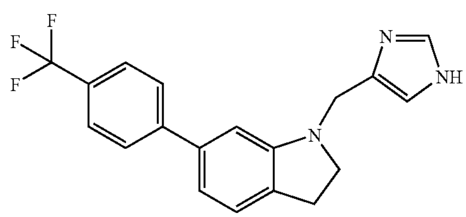 [SMILES: FC(F)(F)c1ccc(-c2ccc3c(c2)N(Cc2c[nH]cn2)CC3)cc1] | 344 |
| 172 | 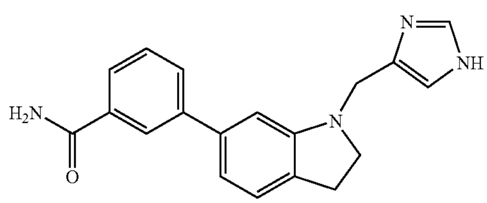 [SMILES: NC(=O)c1cccc(-c2ccc3c(c2)N(Cc2c[nH]cn2)CC3)c1] | 319 |
| 173 | 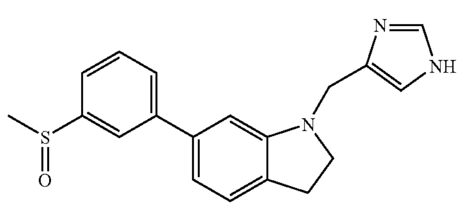 [SMILES: CS(=O)c1cccc(-c2ccc3c(c2)N(Cc2c[nH]cn2)CC3)c1] | 338 |
| 174 | 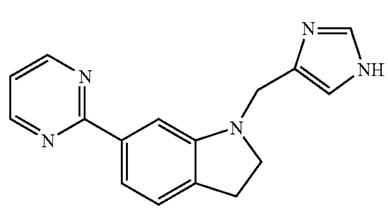 [SMILES: c1cnc(-c2ccc3c(c2)N(Cc2c[nH]cn2)CC3)nc1] | 278 |

-continued

| Cpd | Structure | MS (MH+) |
| --- | --- | --- |
| 175 | 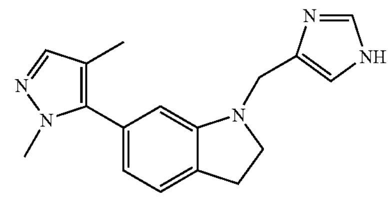 [SMILES: Cc1cnn(C)c1-c1ccc2c(c1)N(Cc1c[nH]cn1)CC2] | 294 |
| 176 | 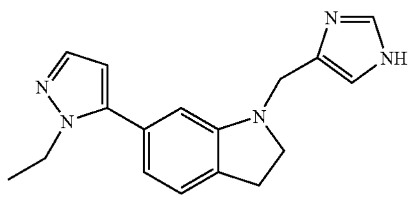 [SMILES: CCn1nccc1-c1ccc2c(c1)N(Cc1c[nH]cn1)CC2] | 294 |
| 177 | 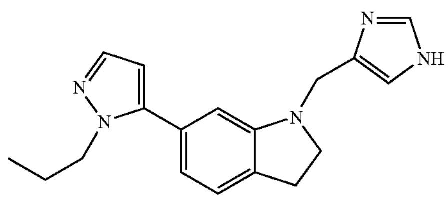 [SMILES: CCCn1nccc1-c1ccc2c(c1)N(Cc1c[nH]cn1)CC2] | 308 |
| 178 | 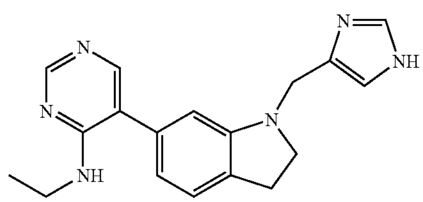 [SMILES: CCNc1ncncc1-c1ccc2c(c1)N(Cc1c[nH]cn1)CC2] | 321 |
| 179 | 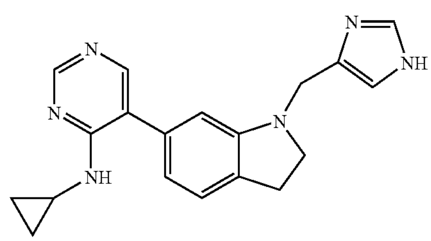 [SMILES: c1ncc(-c2ccc3c(c2)N(Cc2c[nH]cn2)CC3)c(NC2CC2)n1] | 333 |
| 180 | 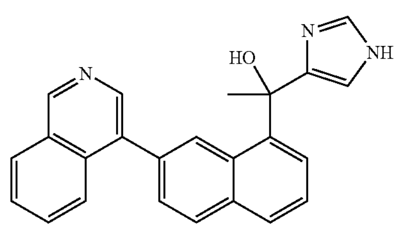 [SMILES: CC(O)(c1c[nH]cn1)c1cccc2ccc(-c3cncc4ccccc34)cc12] | 366 |
| 181 | 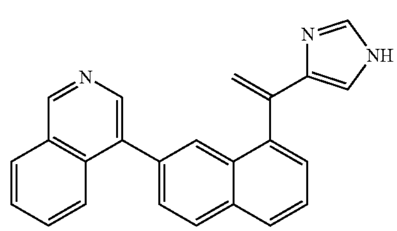 [SMILES: C=C(c1c[nH]cn1)c1cccc2ccc(-c3cncc4ccccc34)cc12] | 348 |

-continued

| Cpd | Structure | MS (MH+) |
|---|---|---|
| 182 | 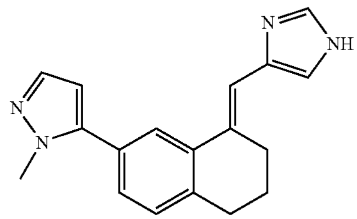 [SMILES: Cn1nccc1-c1ccc2c(c1)/C(=C/c1c[nH]cn1)CCC2] | 291 |
| 183 | 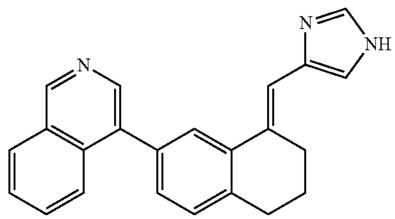 [SMILES: C(=C1/CCCc2ccc(-c3cncc4ccccc34)cc21)/c1c[nH]cn1] | 338 |
| 184 | 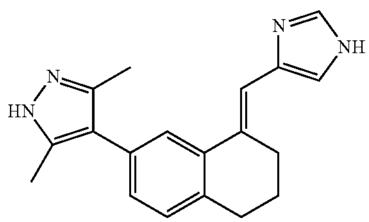 [SMILES: Cc1n[nH]c(C)c1-c1ccc2c(c1)/C(=C/c1c[nH]cn1)CCC2] | 305 |
| 185 | 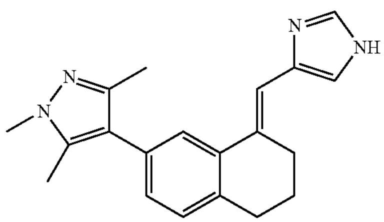 [SMILES: Cc1nn(C)c(C)c1-c1ccc2c(c1)/C(=C/c1c[nH]cn1)CCC2] | 319 |
| 186 | 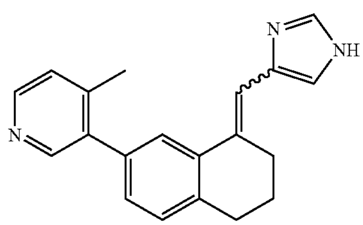 [SMILES: Cc1ccncc1-c1ccc2c(c1)C(=Cc1c[nH]cn1)CCC2] | 302 |
| 187 | 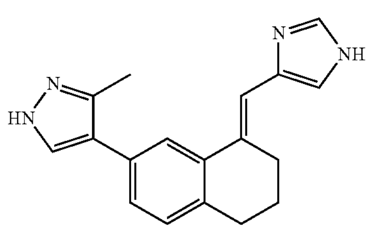 [SMILES: Cc1n[nH]cc1-c1ccc2c(c1)/C(=C/c1c[nH]cn1)CCC2] | 291 |
| 188 | 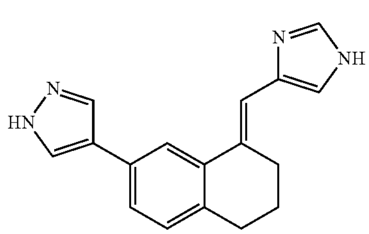 [SMILES: C(=C1/CCCc2ccc(-c3cn[nH]c3)cc21)/c1c[nH]cn1] | 277 |

-continued

| Cpd | Structure | MS (MH+) |
|---|---|---|
| 189 | 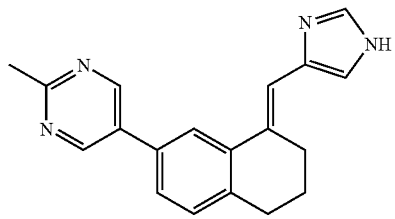 [SMILES: Cc1ncc(-c2ccc3c(c2)/C(=C/c2c[nH]cn2)CCC3)cn1] | 303 |
| 190 | 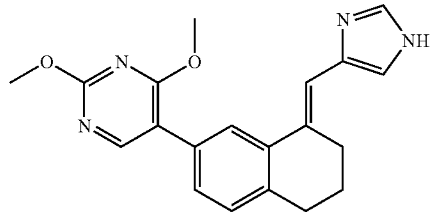 [SMILES: COc1ncc(-c2ccc3c(c2)/C(=C/c2c[nH]cn2)CCC3)c(OC)n1] | 349 |
| 191 | 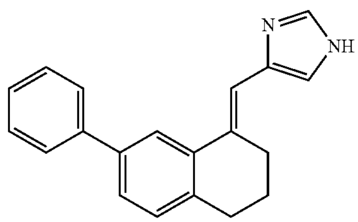 [SMILES: C(=C1/CCCc2ccc(-c3ccccc3)cc21)/c1c[nH]cn1] | 287 |
| 192 | 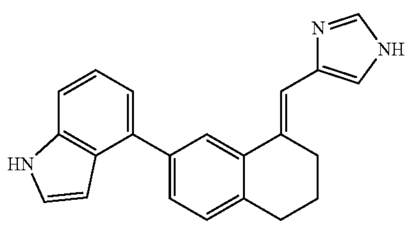 [SMILES: C(=C1/CCCc2ccc(-c3cccc4[nH]ccc34)cc21)/c1c[nH]cn1] | 326 |
| 193 | 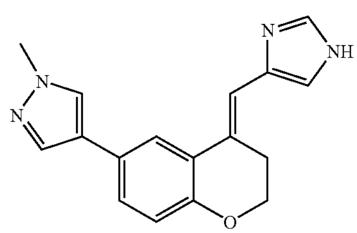 [SMILES: Cn1cc(-c2ccc3c(c2)/C(=C/c2c[nH]cn2)CCO3)cn1] | 293 |
| 194 | 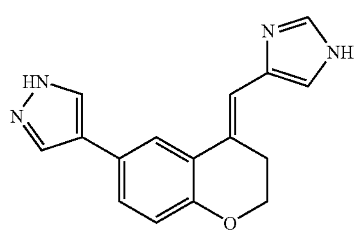 [SMILES: C(=C1/CCOc2ccc(-c3cn[nH]c3)cc21)/c1c[nH]cn1] | 279 |
| 195 | 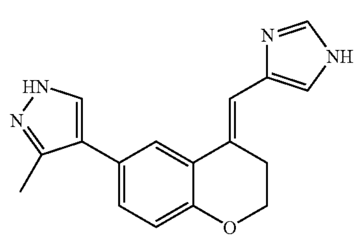 [SMILES: Cc1n[nH]cc1-c1ccc2c(c1)/C(=C/c1c[nH]cn1)CCO2] | 293 |

| Cpd | Structure | MS (MH+) |
|---|---|---|
| 196 | 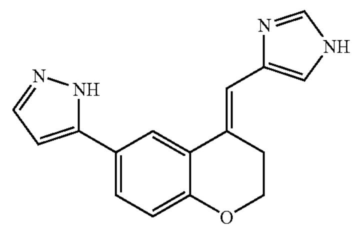 [SMILES: C(=C1/CCOc2ccc(-c3ccn[nH]3)cc21)/c1c[nH]cn1] | 279 |
| 197 | 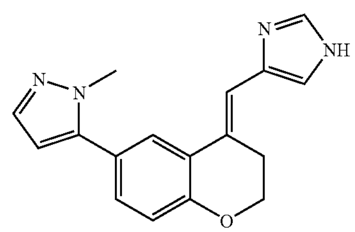 [SMILES: Cn1nccc1-c1ccc2c(c1)/C(=C/c1c[nH]cn1)CCO2] | 293 |
| 198 | 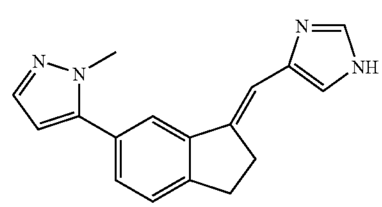 [SMILES: Cn1nccc1-c1ccc2c(c1)/C(=C/c1c[nH]cn1)CC2] | 277 |
| 199 | 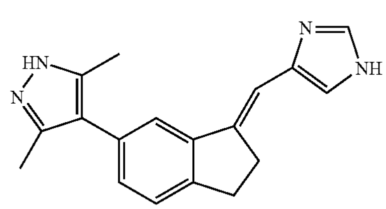 [SMILES: Cc1n[nH]c(C)c1-c1ccc2c(c1)/C(=C/c1c[nH]cn1)CC2] | 291 |
| 200 | 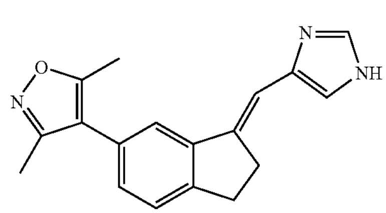 [SMILES: Cc1noc(C)c1-c1ccc2c(c1)/C(=C/c1c[nH]cn1)CC2] | 292 |

| Cpd | Structure | MS (MH+) |
|---|---|---|
| 201 | 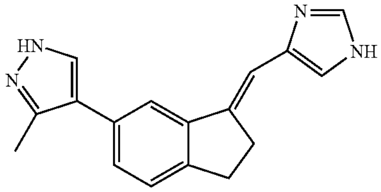 [SMILES: Cc1n[nH]cc1-c1ccc2c(c1)/C(=C/c1c[nH]cn1)CC2] | 277 |
| 202 | 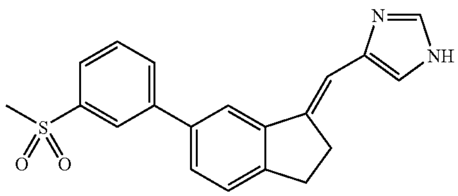 [SMILES: CS(=O)(=O)c1cccc(-c2ccc3c(c2)/C(=C/c2c[nH]cn2)CC3)c1] | 351 |
| 203 | 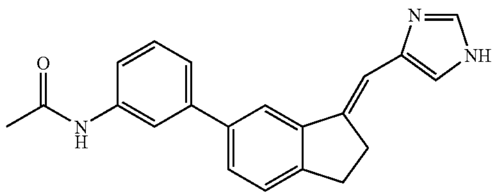 [SMILES: CC(=O)Nc1cccc(-c2ccc3c(c2)/C(=C/c2c[nH]cn2)CC3)c1] | 330 |
| 204 | 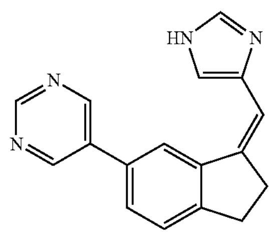 [SMILES: C(=C1\CCc2ccc(-c3cncnc3)cc21)/c1c[nH]cn1] | 275 |
| 205 | 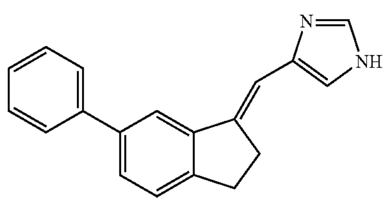 [SMILES: C(=C1/CCc2ccc(-c3ccccc3)cc21)/c1c[nH]cn1] | 273 |

Assay:

Efficacy agonist activity values (Emax, GTPγS assay) for α2A and α2C were determined by following the general procedure detailed by UmLand et al ("Receptor reserve analysis of the human $\alpha_{2c}$-adrenoceptor using [$^{35}$S]GTPγS and cAMP functional assays" European Journal of Pharmacology 2001, 411, 211-221). For the purposes of the present invention, a compound is defined to be a specific or at least selective agonist of the α2C receptor subtype if the compound's efficacy at the α2C receptor is ≧30% Emax (GTPγS assay) and its efficacy at the α2A receptor is ≦30% Emax (GTPγS assay).

The following compounds were evaluated to be specific or at least selective agonists of the α2C receptor subtype based on the previously defined definition: 1, 3, 4, 6, 9, 10D, 19, 102, 105, 108, 114, 139, 141, 142, 143, 144, 151, 175, 178, 182, 187, 195, and 197.

While the present invention has been described with in conjunction with the specific embodiments set forth above, many alternatives, modifications and other variations thereof will be apparent to those of ordinary skill in the art. All such alternatives, modifications and variations are intended to fall within the spirit and scope of the present invention.

What is claimed is:

1. The compound represented by the structural Formula Ia

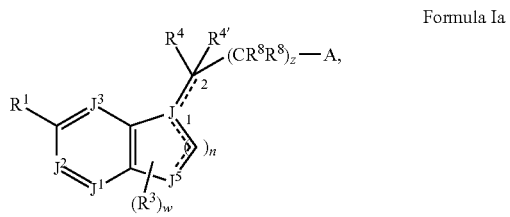

Formula Ia or a pharmaceutically acceptable salt thereof,
wherein:
(i) "w" and "z" are 0, "n" is 1, A is a compound of the formula:

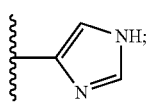

J¹ is CH, J², and J³ are —C(R²)—;
J is N;
J⁵ is CH;
R⁴ and R⁴' are —H;
providing a compound represented by the Formula:

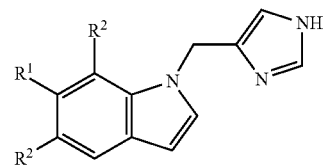

wherein R² is independently for each occurrence —H or —CH₃; and
R¹ is a ring which is:

(a)

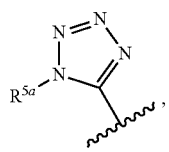

wherein $R^{5a}$ is —H, —CH₃, —(CH₂)—CH₃, —(CH₂)₂—CH₃, —CH—(CH₃)₂, —(CH₂)₂—O—CH₃, —CH₂—CN, or —(CH₂)₂—CN; or (b)

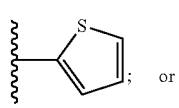; or (c)

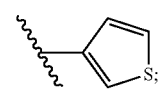;

or (d)

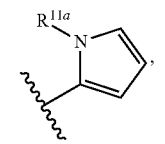, wherein $R^{11a}$ is independently —H or —CH₃, or (e)

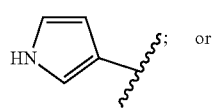; or (f)

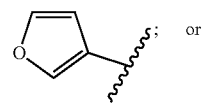; or (g)

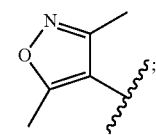;

or (h)

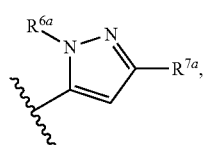, wherein $R^{6a}$ is independently —H, CH₃, —CH₂—CH₃, or —(CH₂)₂—CH₃ and $R^{7a}$ is independently, —H, —CH₃, —CF₃; or (i)

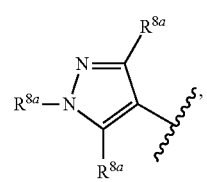, wherein $R^{8a}$ is independently for each occurrence: —H, or —CH₃; or (j)

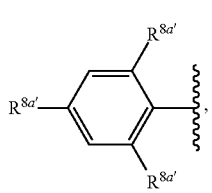, wherein $R^{8a'}$ is independently for each occurrence: —H; —NH₂; —CH₃; —(CH)—(CH₃)₂; —NH—CH₃; —NH—(CH₂)—CH₃; —NH-cyclopropyl-O—CH₃; or —O-benzyl; or (k)

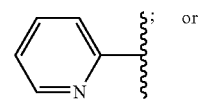; or (l)

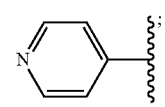;

or

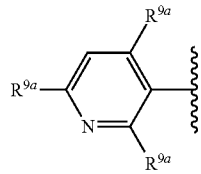 (l)

wherein R⁹ᵃ is independently for each occurrence: —H; —CH₃, —O—CH₃; —O—(CH₂)₃—N(CH₃)₂; or

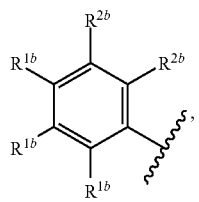 (m)

wherein: (i) each $R^{2b}$ is —H and $R^{1b}$ is independently —H, —CH₃, —CH₂—CH₃, —CF₃, —Cl; —F; (ii) (i) each $R^{2b}$ is —H, two of $R^{1b}$ are —H and one of $R^{1b}$ is -phenyl, —O—CF₃, —CN, —O-benzyl, —S(O)₂—CH₃, —NH—S(O)₂—CH₃, —S(O)₂—NH₂, —S(O)—CH₃, —C(O)—NH₂; or (iii) one of $R^{2b}$ is —F or —CH₃, one of $R^{1b}$ is —CH₃, —O-phenyl, —C(O)—OH, —OH, or —F, and the others of $R^{1b}$ and $R^{2b}$ are —H; or

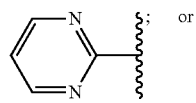 (n)

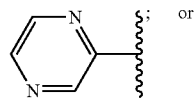 (o)

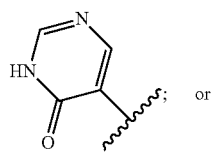 (p)

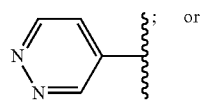 (q)

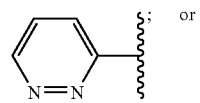 (r)

-continued

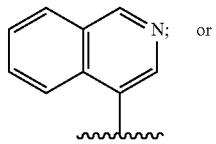 (s)

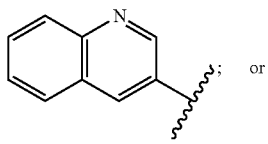 (t)

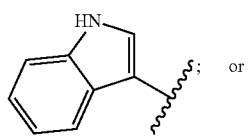 (u)

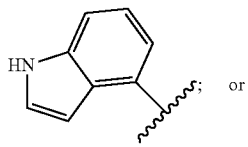 (v)

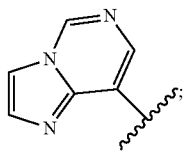 (w)

or (ii) "w" and "z" are 0, "n" is 2, A is a compound of the formula:

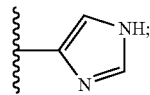

$J^1$, $J^2$, and $J^3$ are —CH—;

J is —CH₂—;

$J^5$ is —O—;

$R^4$ and $R^{4'}$ are —H;

$R^1$ is a compound of the Formula:

to yield a compound of the Formula:

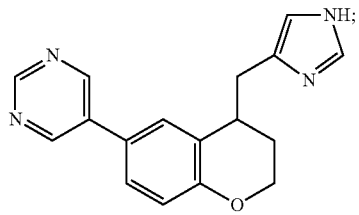 [SMILES: c1ncc(-c2ccc3c(c2)C(Cc2c[nH]cn2)CCO3)cn1]

or (iii) "w" and "z" are 0, "n" is 2, A is a compound of the formula:

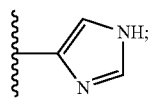

J, $J^1$, $J^2$, and $J^3$ are —CH—;
$R^4$ is —H, $R^{4'}$ is not there; and
atoms 1 and 2 form a double bond;
to yield a compound of the Formula:

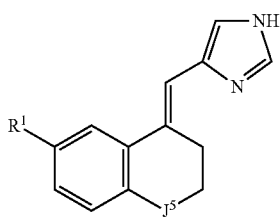

wherein:
$J^5$ is —CH$_2$— or —O—; and
$R^1$ is:
(a) -phenyl;

(b)
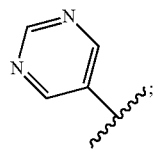

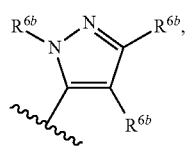

wherein, for each occurrence, $R^{6b}$ is independently —H or —CH$_3$;

(d)
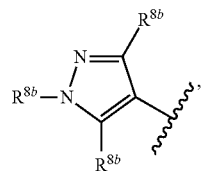

wherein $R^{8b}$ is independently for each occurrence: —H, or —CH$_3$; or (e)
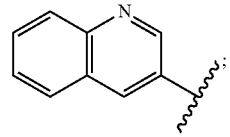

(f)
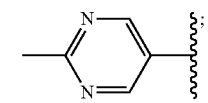

(g)
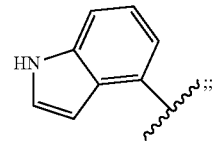

(h)
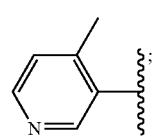

(i)
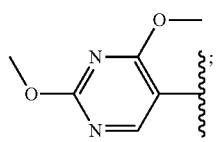

or
(iv) "w" and "z" are 0, "n" is 1, A is a compound of the formula:

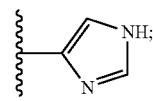

J, $J^1$, $J^2$, and $J^3$ are —CH—;
$J^5$ is CH$_2$;
$R^4$ is —H, $R^{4'}$ is not there; and
atoms 1 and 2 form a double bond;

thereby providing a compound of the Formula:

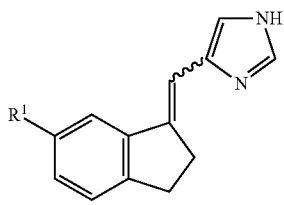

wherein:

R¹ is:

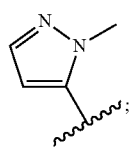

(a)

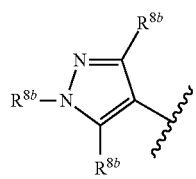

(b)

wherein, for each occurrence, $R^{8b}$ is independently —H or —CH₃;

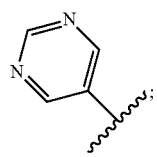

(c)

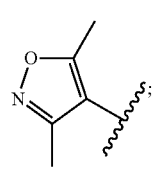

(d)

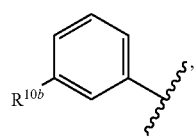

(e)

wherein $R^{10b}$ is independently, —H, —CH₃, —CH₂—CH₃, —CF₃, —S(O)₂—CH₃, or —NH—C(O)—CH₃.

2. A compound which has the formula:

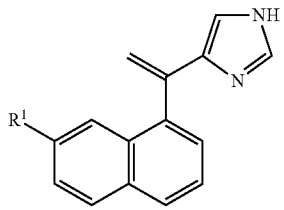

wherein R¹ is

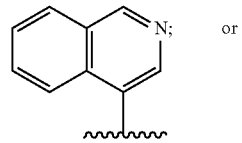 or (a)

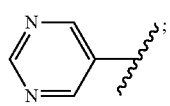

(b)

or a pharmaceutically acceptable salt thereof.

3. The compound of Structure XI

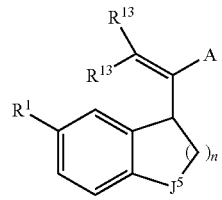

XI or a pharmaceutically acceptable ester or salt thereof
wherein
A is imidazole;
R¹ is selected from the group consisting of optionally substituted aryl, optionally substituted arylalkyl, optionally substituted arylalkoxy, optionally substituted pyridyl, optionally substituted pyrimidyl, optionally substituted furanyl, optionally substituted thiophenyl, optionally substituted quinolinyl, optionally substituted indolyl, optionally substituted pyrrolyl, and optionally substituted pyrrolidinyl, wherein said groups may be optionally substituted 1 to 3 times with substitutents selected from the group consisting of alkyl, haloalkyl, nitro, cyano, halo, hydroxyl, amino, alkylamino, dialkylamino, —C(O)-amino; —C(O)-alkylamino, —C(O)-dialkylamino, —C(O)—OH, —C(O)—Oalkyl, alkoxy, haloalkoxy, aryl, and heteroaryl, wherein said aryl and heteroaryl are optionally substituted 1 to 3 times by alkyl, haloalkyl, nitro, cyano, halo, hydroxyl, amino, alkylamino, dialkylamino, alkoxy, and haloalkoxy;
$R^{13}$ is independently selected from the group consisting of H and alkyl, alkoxy, alkenyl, alkenyloxy, alkynyl, cycloalkyl, cycloalkoxy, aryl, aryloxy, arylalky, heteroaryl, heteroarylalkyl, heterocyclyl, and heterocyclylalkyl groups optionally substituted with at least one R⁵;

n is 1 or 2; and

J⁵ is —(CH₂)—, —O—, or —S—.

4. A compound selected from the group consisting of:

-continued

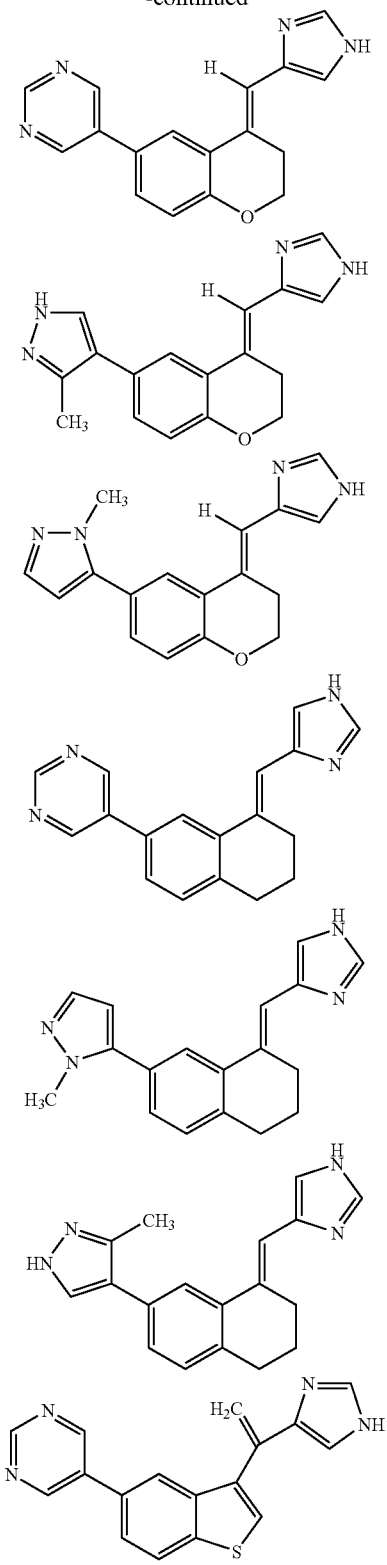

or a pharmaceutically acceptable salt thereof.

5. A pharmaceutical composition comprising at least one compound of claim 1, or a pharmaceutically acceptable salt thereof and at least one pharmaceutically acceptable carrier, adjuvant or vehicle.

6. A pharmaceutical composition of claim 5 which comprises additionally one or more therapeutic agents which are glucosteroids, PDE-4 inhibitors, anti-muscarinic agents, cromolyn sodium, $H_1$ receptor antagonists, 5-$HT_1$ agonists, NSAIDs, angiotensin-converting enzyme inhibitors, angiotensin II receptor agonists, β-blockers, β-agonists, leukotriene antagonists, diuretics, aldosterone antagonists, ionotropic agents, natriuretic peptides, pain management agents, anti-anxiety agents, anti-migraine agents, or therapeutic agents suitable for treating heart conditions, psychotic disorders, or glaucoma.

7. A compound of the following formula

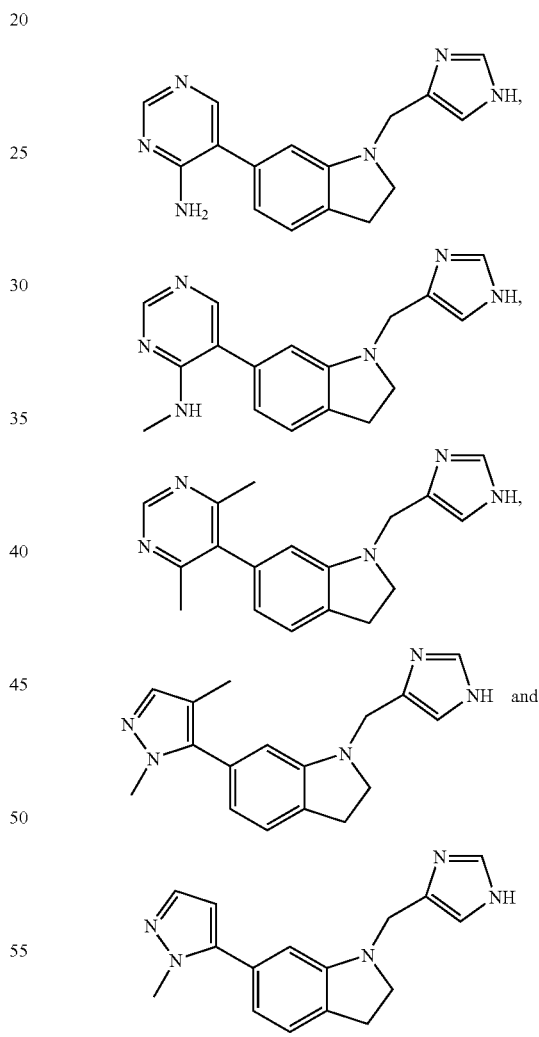

or a pharmaceutically acceptable salt thereof.

* * * * *